(12) United States Patent
Tangy et al.

(10) Patent No.: US 8,586,364 B2
(45) Date of Patent: Nov. 19, 2013

(54) CELLS AND METHODOLOGY TO GENERATE NON-SEGMENTED NEGATIVE-STRAND RNA VIRUSES

(75) Inventors: Frédéric Tangy, Les Lilas (FR); Pierre Charneau, Paris (FR); Yves Jacob, Maintenon (FR)

(73) Assignee: Institut Pasteur, Paris (FR)

( * ) Notice: Subject to any disclaimer, the term of this patent is extended or adjusted under 35 U.S.C. 154(b) by 712 days.

(21) Appl. No.: 12/448,468

(22) PCT Filed: Dec. 21, 2007

(86) PCT No.: PCT/IB2007/004444
§ 371 (c)(1),
(2), (4) Date: Dec. 18, 2009

(87) PCT Pub. No.: WO2008/078198
PCT Pub. Date: Jul. 3, 2008

(65) Prior Publication Data
US 2010/0144040 A1 Jun. 10, 2010

(30) Foreign Application Priority Data

Dec. 22, 2006 (EP) .................................... 06292025

(51) Int. Cl.
*C12N 7/01* (2006.01)
*C12N 7/02* (2006.01)
*C12N 7/04* (2006.01)
*A61K 39/165* (2006.01)

(52) U.S. Cl.
USPC ........ 435/455; 435/239; 435/320.1; 435/366; 424/204.1; 424/212.1

(58) Field of Classification Search
None
See application file for complete search history.

(56) References Cited

FOREIGN PATENT DOCUMENTS

| WO | WO 97/06270 | 2/1997 |
|---|---|---|
| WO | WO 04/001051 A2 | 12/2003 |
| WO | 2004/113517 A2 | 12/2004 |

OTHER PUBLICATIONS

Tangy et al. Live Attenuated Measles Vaccine as a Potential Multivalent Pediatric Vaccination Vector. Viral Immunology 2005, vol. 18, No. 2, pp. 317-326.*
Dardalhon et al. Lentivirus-mediated gene transfer in primary T cells in enhanced by a central DNA flap. Gene Therapy 2001, vol. 8, pp. 190-198.*
Arhel, N. et al., "Nuclear import defect of human immunodeficiency virus type 1 DNA flap mutants is not dependent on the viral strain or target cell type," Journal of Virology, vol. 80, No. 20, pp. 10262-10269 (2006).
Barry, S. C., et al., "Lentivirus vectors encoding both central polypurine tract and posttranscriptional regulatory element provide enhanced transduction and transgene expression," Human Gene Therapy, vol. 12, No. 9, pp. 1103-1108 (2001).
Breckpot, K., et al., "Lentivirally transduced dendritic cells as a tool for cancer immunotherapy," The Journal of Gene Medicine, vol. 5, No. 8, pp. 654-667 (2003).
Combredet, C, et al., "A Molecularly Cloned Schwarz Strain of Measles Virus Vaccine Induces Strong Immune Responses in Macaques and Transgenic Mice," Journal of Virology, vol. 77, No. 21, pp. 11546-11554 (2003).
Radecke, F., et al., "Rescue of Measles Viruses From Cloned DNA," EMBO Journal, vol. 14, No. 23, pp. 5773-5784 (1995).
Whitwam, T., et al., "Identification of a central DNA flap in feline immunodeficiency virus," Journal of Virology, vol. 75, No. 19, pp. 9407-9414 (2001).
Sirven, A., et al., Molecular Therapy, Apr. 2001, vol. 3, No. 4, pp. 438-448.
Moll, M. et al., Polarized Glycoprotein Targeting Affects the Spread of Measles virus in vitro and in vivo, Journal of General Virology (2004) 85: 1019-1027.
Takeuchi, Kaoru et al., "Toward Understanding the Pathogenicity of Wild-Type Measles Virus by Reverse Genetics," Jpn. J. Infect. Dis., (2002) 55:143-149.
Neumann, G. et al., A Decade after the Generation of a Negative-Sense RNA Virus from cloned cDNA—What have we learned?, Journal of General Virology (2002) 83:2635-2662.

* cited by examiner

*Primary Examiner* — Louise Humphrey
(74) *Attorney, Agent, or Firm* — Law Office of Salvatore Arrigo and Scott Lee, LLP

(57) ABSTRACT

The present invention relates to recombinant cells as well as to methods for the generation of non-segmented negative-sense single-stranded RNA viruses (NNV or mononegavirales) from cloned deoxyribonucleic acid (cDNA), especially from measles virus and in particular from attenuated strains such as those approved for vaccination, in particular from the attenuated Schwarz measles virus and various recombinant Schwarz measles-based viruses expressing heterologous sequences. Such rescued viruses can be used, after amplification, as vaccines for immunization against measles and/or against the heterologous peptides or proteins expressed.

16 Claims, 2 Drawing Sheets

CELLS AND METHODOLOGY TO GENERATE NON-SEGMENTED NEGATIVE-STRAND RNA VIRUSES

The present invention relates to recombinant cells as well as to methods for the generation of non-segmented negative-sense single-stranded RNA viruses (NNV or mononegavirales) from cloned deoxyribonucleic acid (cDNA), especially from measles virus and in particular from attenuated strains such as those approved for vaccination, in particular from the attenuated Schwarz measles virus and various recombinant Schwarz measles-based viruses expressing heterologous sequences. Such rescued viruses can be used, after amplification, as vaccines for immunization against measles and/or against the heterologous peptides or proteins expressed.

Live attenuated RNA viruses make very efficient vaccines. Among these, measles vaccine has been used in hundreds of millions of children and has been proven to be effective and safe. This vaccine induces life-long immunity after one or two injections. It is easily produced on a large scale at low cost in most countries. These advantages make measles virus, especially attenuated vaccine strains, a good candidate vector to immunize children but even in some circumstances adult populations, against both measles and/or other infectious pathologies, especially viral pathologies such as AIDS (retroviruses), flavivirus or coronavirus (SARS) diseases.

Live attenuated measles virus has been used as vaccine since the 1960s and is one of the most effective and safest human vaccines. Vaccination campaigns have been very effective to control measles in developed countries. However, due to inadequate distribution of the vaccine in developing countries, measles still infects approximately 45 million individuals and is responsible for the death of 700,000 children per year. The WHO has therefore stepped up its global vaccination program for the next 10-20 years (C.D.C., 2005). Taking advantage of the WHO campaigns, the use of vaccine vectors derived from measles vaccine would allow in certain regions of the world the simultaneous immunization of children against measles and other infectious diseases with new multivalent, especially bivalent pediatric vaccines that are both safe and effective.

Measles virus (MV) belongs to the genus *Morbillivirus* in the family Paramyxoviridae. It is an enveloped virus with a non-segmented RNA genome of negative polarity (15,894 bp). Measles can only be contracted once as the immune system mounts a strong specific response and establishes life-long memory protecting against re-infection. Such protection is based on both the production of antibodies and memory cytotoxic $CD8^+$ T lymphocytes (CTL). Pathogenic strains strongly disrupt hematopoiesis (Ameborn et al., 1983; Kim et al., 2002; Okada et al., 2000) thus resulting in transitory immunosuppression responsible for most deaths due to measles infection in developing countries. In contrast to primary strains, attenuated strains do not induce immunosuppression (Okada et al., 2001).

The Edmonston strain of measles virus was isolated in 1954 by culture in primary human cells (Enders et al., 1954). Adaptation to chicken embryonic fibroblasts produced vaccine seeds that were furthermore attenuated by subsequent passages in chicken embryonic fibroblasts (Schwarz et al., 1962). The Schwarz and Moraten strains that possess identical nucleotide sequences (Parks et al., 2001a; Parks et al., 2001 b) constitute the most frequently used measles vaccine. Vaccination with one or two injections induces life-long immunity (Griffin et al., 2001; Hilleman et al., 2002). Persistence of CD8 cells and antibodies has been demonstrated up to 25 years after vaccination (Ovsyannikova et al., 2003). The measles vaccine is easily produced on a large scale in most countries and may be made available at low cost. Attenuation of the viral genome results from an advantageous combination of multiple mutations. Thus, the vaccine is very stable and reversion of vaccine strains has never been observed to date (Hilleman et al., 2002). In addition, the virus replicates only in the cytoplasm, eliminating any risk of integrating into chromosomes of the host genome. These features make live attenuated measles vaccine an excellent candidate for the development of a multivalent vaccine vector. To this end, an infectious cDNA corresponding to the Edmonston B MV strain antigenome has been cloned and a reverse genetics technique enabling the production of the corresponding virus was established (Radecke et al., 1995).

The inventors have previously developed a vector using the Schwarz MV, the most commonly used measles vaccine in the world (Combredet et al., 2003). This vector can stably express a variety of genes or combination of large genes for more than 12 passages. Recombinant MV vectors containing 4,000-5,000 additional nucleotides were produced, representing an additional 30% of genome. These viruses were produced in cell culture at titers comparable to standard MV. After 12 passages and an amplification factor of $10^{20}$, more than 96% of the infected cells continued to express the additional genes. This remarkably stable expression, also observed for other members of the *Mononegavirales* (Schnell et al., 1996) is likely due to the absence of geometric constraints on the size of the genome by these helicoid nucleocapsid viruses, in contrast to viruses with icosahedral capsids. Moreover, MV infects cells of the immune system (macrophages and dendritic cells), thus delivering the cargo antigens directly to the most effective antigen presenting cells, a major advantage for a vaccine vector. Finally, the MV genome is small, thus avoiding the response to the vector overwhelming the response to transgenes.

Based on the assumption that the safety and efficacy of an attenuated strain ultimately depends on its genome sequence, the inventors cloned the infectious cDNA corresponding to the antigenome of the Schwarz/Moraten measles virus from virus particles purified from an industrial preparation of the Schwarz vaccine with optimal procedures to maintain fidelity (Combredet et al., 2003). To optimize the output of the reverse genetics system, the antigenomic viral cDNA was placed under the control of the T7 phage RNA polymerase promoter with an additional GGG motif required for optimal efficacy. To allow exact cleavage of the viral RNA, a hammerhead ribozyme was inserted between the GGG motif and the first viral nucleotide, and the ribozyme from hepatitis delta virus was placed downstream of the last viral nucleotide. The resulting pTM-MVSchw plasmid enabled the production of the corresponding virus using a previously described reverse genetics system based on the transfection of human helper cells (Radecke et al., 1995). To prevent adaptation of the recombinant vaccine to non-certified cells, the helper cells transfected with cDNA were co-cultivated with chicken embryonic fibroblasts, the cells in which the virus was originally selected and in which it is currently produced. After several passages of recombinant virus the sequence of its entire genome was found identical to the original sequence (Combredet et al., 2003). The immunogenicity of the virus rescued from pTM-MVSchw plasmid was evaluated in transgenic mice and macaques and compared with the industrially manufactured Schwarz vaccine. All vaccinated macaques developed anti-MV antibodies and specific cellular responses. No differences were observed between the Schwarz virus produced from the cDNA and the original vaccine, indicating that the cloned virus had the same immunogenicity as the parental vaccine (Combredet et al., 2003). This molecular clone allows the production of the Schwarz measles vaccine without depending on the seeding stocks.

The pTM-MVSchw plasmid was modified for the expression of foreign genes by the introduction of additional transcriptional units (ATU) at different positions of the genome. These ATUs are multi-cloning site cassettes inserted for example in a copy of the intergenic N-P region of the viral genome (containing the cis acting sequences required for transcription). The enhanced green fluorescent protein (eGFP) gene was inserted into this cassette. The ATU was introduced into the pTM-MVSchw plasmid in two positions (between the P and M genes and between the H and L genes). Irrespective of the additional sequence, the total number of antigenomic nucleotides must be maintained as a multiple of six to fulfill the "rule of 6 nucleotides" that optimizes viral replication (Calain et al., 1993). The GFP transgene was expressed in all infected cell types, confirming that the recombinant Schwarz measles virus works as a vector. This vector allows the design of combined vaccines based on a live attenuated approved vaccine strain that is currently globally in use. This work is the object of international application WO 2004/000876 which is incorporated herewith by reference.

The use of such MV-based live recombinant vaccines at large scale depends on the possibility of growing them stably and at good titers on certified cells (such as primary chicken embryonic fibroblasts (CEF) or human diploid MRC5). These cells usually produce MV at moderate titers as compared to laboratory cell lines, such as African green monkey Vero cells, that produce at high titers. Thus, the initial seed must be obtained at a relatively high titer. This initial seed is produced from cDNA by reverse genetics.

While positive-strand RNA or DNA viruses can be easily obtained in vitro after transfection of their engineered infectious cDNA or DNA in appropriate cells, the negative-strand RNA viruses cannot be rescued directly by reverse genetics from their cDNA. The genome of negative-strand RNA viruses is not able to initiate in vitro an infectious cycle because it does not code directly for proteins. Both transcription and replication require a transcriptase-polymerase enzymatic complex contained in the nucleoproteins encapsidating the viral genome (RNP complex). Thus, the generation of recombinant negative-strand RNA viruses from cDNA involves reconstitution of active RNPs from individual components: RNA and proteins (Fields B. N. et al—Lippincott Raven publishers 1996, p. 1953-1977).

For the last 15 years, a remarkable set of work from numerous laboratories has allowed the establishment of different systems for rescuing almost all negative-strand RNA viruses from their cDNA (for review see Conzelmann). In contrast to the viruses with segmented genomes, the RNPs of non-segmented negative-strand RNA viruses (*Mononegavirales*) are tightly structured and contain, in addition to the nucleoprotein (N), the assembly and polymerase cofactor phosphoprotein (P) and the viral RNA polymerase large protein (L), The first infectious *Mononegavirales*, the rabies rhabdovirus, was recovered from cDNA in 1994 (Schnell et al. 1994). The approach involved intracellular expression of rabies virus N, P, and L protein, along with a full-length RNA whose correct 3' end was generated by the hepatitis delta virus (HDV) ribozyme. A transcript corresponding to the viral antigenome (positive strand) rather than to the genome (negative strand) was used to avoid an antisense problem raised by the presence of N, P, and L sequences in full-length RNAs. In this system, the essential helper proteins were provided by a replication-competent vaccinia vector encoding the phage T7 RNA polymerase to drive T7-specific transcription of plasmids encoding the required N, P and L proteins. Similar systems allowed recovery of infectious rabies viruses (Schnell et al. 1994; Ito et al. 2001), VSV (Lawson et al. 1995; Whelan et al. 1995), as well as the Paramyxoviridae Sendai virus (Garcin et al. 1995; Kato et al. 1996; Leyrer et al. 1998; Fujii et al. 2002), HP1V-3 (Hoffman and Banerjee 1997) and measles virus (Takeda et al. 2000; Fujii et al. 2002).

To avoid the use of replication-competent vaccinia, which requires that the rescued virus be separated from helper virus, several non-replicative helper viruses have been adapted to provide helper proteins to rescue non-segmented negative-strand RNA viruses. The highly attenuated modified vaccinia virus Ankara (MVA) expressing T7 RNA polymerase has been used for recovery of the Pneumovirus RSV (Collins et al. 1995), the Rubulavirus, SV5 (He et al. 1997), HPIV-3 (Durbin et al. 1997), rinderpest virus (Baron and Barrett 1997), and measles virus (Schneider et al. 1997), mumps virus (Clarke et al. 2000), CDV (Gassen et al. 2000), HPIV-2 (Kawano et al. 2001), and BPIV-3 (Schmidt et al. 2000). A recombinant fowlpox virus expressing the T7 RNA polymerase has been used for the recovery of the avian Paramyxoviridae NDV (Peeters et al. 1999) and of a chimeric rinderpest virus (Das et al. 2000).

To rescue *Mononegavirales* without contamination by any infectious or defective viral vector, cell lines expressing T3 or T7 RNA polymerase have been generated. In this case, in the absence of RNA-capping activity in the cytoplasm, protein expression was achieved using the IRES from encephalomyocarditis virus (EMCV) located upstream of the coding regions. A human embryo kidney cell line (293-3-46) expressing T7 RNA polymerase and measles virus proteins N and P was established to recover the Edmonston vaccine strain of measles virus (Radecke et al. 1995). The virus was rescued after transfection of plasmids specifying MV antigenomic RNA and L mRNA. It was shown that rescue efficiency in these cells, which was very low initially, was increased by heat shock treatment of the transfected cultures and additional cocultivation of transfected cells on Vero cells (Parks et al., 1999). Another cell line expressing T7 RNA polymerase (BSR T7/5) and based on baby hamster kidney cells (BHK) was used for recovery of BRSV (Buchholz et al. 2000), rabies viruses (Finke and Conzelmann 1999), VSV (Harty et al. 2001), NDV (Romer-Oberdorfer et al. 1999), and Ebola virus (Volchkov et al. 2001).

The inventors have used the 293-3-46 cell line to rescue the Schwarz vaccine MV vector (Combredet et al., 2003). However, they have experienced that, even using the heat shock method on transfected cells (Parks et al., 1999) and their cocultivation on Vero or CEF cells, the rescue was rather irreproducible and still at very low yield, or even impossible for some recombinants containing large additional sequences. This was due to the instability of helper cells since it was observed that the efficiency depends on the number of their passages. These cells have been generated by selecting geneticin-resistant clones of 293 cells transfected with pSC6-N, pSC6-P and pSC6-T7-NEO encoding respectively the MV N and P genes and the T7 RNA polymerase gene under control of the CMV promoter and a neomycin resistance gene (Radecke et al., 1995). The stability of their activity depends on their continuous selection under geneticin (G-418), and the removing of antibiotic during transfection and rescue experiments. During the illicit plasmid-based recombination of foreign DNA into chromosomic DNA, the concatemeres formed by plasmids are recombined and the geneticin selection maintains only the individual copies, which are very few. This might explain the reduction of efficiency observed with 293-3-46 cells after a few passages.

Therefore, there exists a need in the art for a new method for generating helper cell lines able to rescue, reproducibly and with high efficiency, recombinant, non-segmented negative-strand RNA viruses from cDNA, optionally modified, and without contamination by any other helper virus such as vaccinia virus.

BRIEF DESCRIPTION OF THE SEQUENCES

Figure 1:
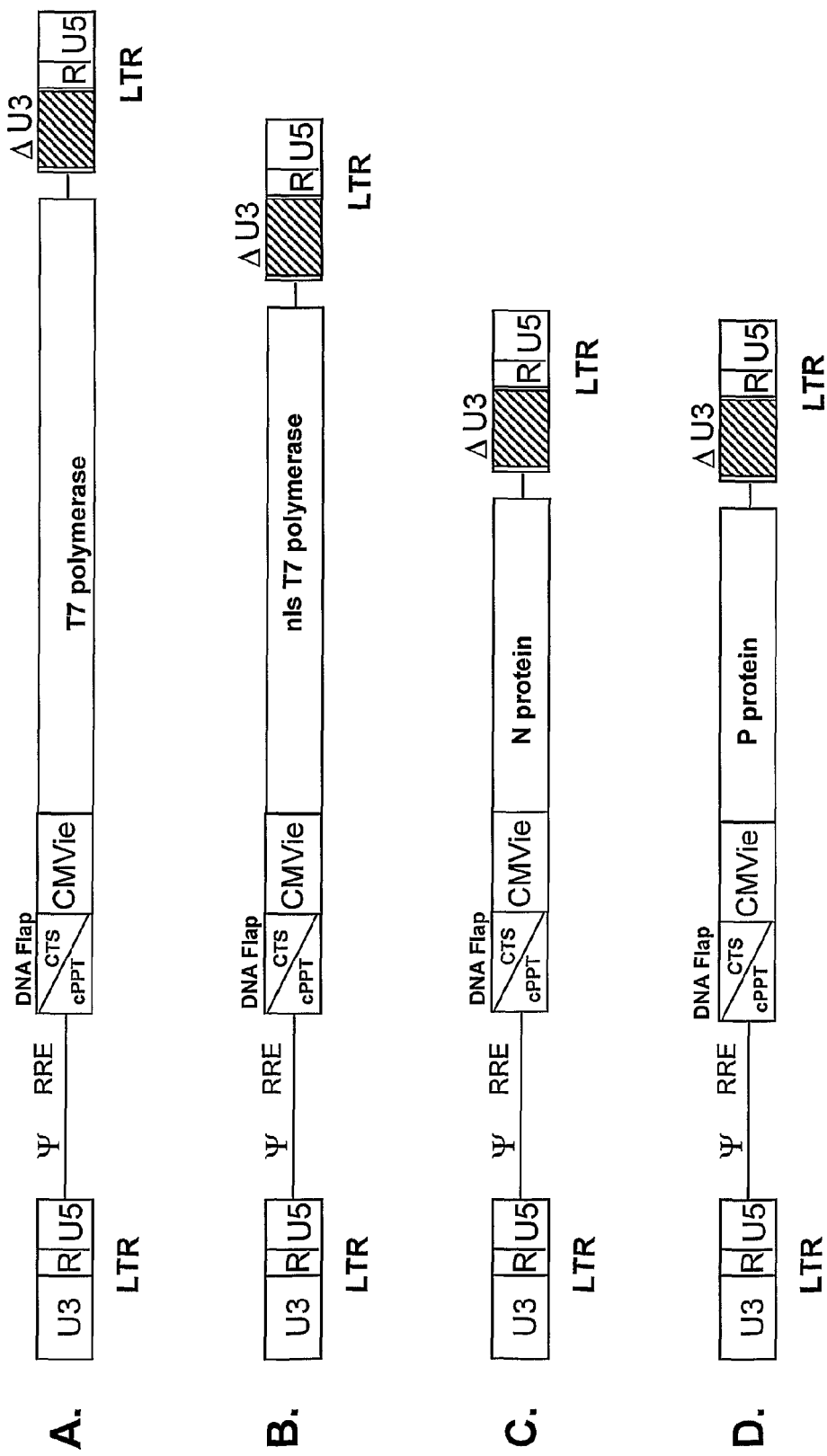
FIG. 1: schematic representation of the plasmids HIV-1-TRIPΔU3.CMV-T7 (A), HIV-1-TRIPΔU3.CMV-nlsT7 (B), HIV-1-TRIPΔU3.CMV-N (C) and HIV-1-TRIPΔU3.CMV-P (D). ψ: packaging psi motif: RRE: Rev-responsive element; cPPT: central polypurine tract, CTS: central termination sequence, CMVie: cytomegalovirus immediate-early promoter; ΔU3: deletion of parts of U3.

Nucleotide sequences of various retrovirus DNA FLAP are defined in different viruses: CAEV (SEQ ID NO:1), EIAV (SEQ ID NO:2), VISNA (SEQ ID NO:3), SIV AGM (SEQ ID NO:4), HIV-2 ROD (SEQ ID NO:5), HIV-1 LAI (SEQ ID NO:6) and HIV-1 (SEQ ID NO:7). The nucleotide sequences of the T7 RNA polymerase, the nls T7 RNA polymerase and the N, P and L proteins of the MV virus are defined respectively in SEQ ID NO: 8, 10, 12, 14 and 16, as well as their respective corresponding protein sequences in SEQ ID NO: 9, 11, 13, 15 and 17. The complete nucleotide sequence of the pTM-MVSchw plasmid (CNCM 1-2889) is defined in SEQ ID NO: 18. The complete nucleotide sequence of the pEMC-LSchw plasmid (CNCM 1-3881) is defined in SEQ ID NO: 19.

DETAILED DESCRIPTION

The present invention relates to a cell stably producing at least a RNA polymerase, a nucleoprotein (N) of a non-segmented negative-strand RNA virus and a phosphoprotein (P) of a non-segmented negative-strand RNA virus, or functional derivatives thereof. In a particular embodiment, the cell of the invention stably produces a RNA polymerase, a nucleoprotein (N) of a non-segmented negative-strand RNA virus and a phosphoprotein (P) of a non-segmented negative-strand RNA virus, or functional derivatives thereof.

The cells of the present invention are recombinant cells meaning that these cells are the results of in vitro purposive genetic manipulation resulting in recombination of genomic sequences of the cells with heterologous sequences, i.e., sequences originating from a different cell or organism. Starting from isolated cells, recombinant cells are prepared, have genetic and/or phenotypic features different from those of the starting cells, and also provide for the stable expression or production of at least a RNA polymerase, the N protein and the P protein of one or several non-segmented negative-strand RNA viruses. Cells of the invention are claimed as product, external to the body of a human being.

The expression "stably producing" means that cells express or produce at least the RNA polymerase, the N protein and the P protein over a number of cell divisions equals to or higher than about 65, advantageously as long as the cell survives. According to a particular embodiment of the invention, the recombinant cells express or produce the at least three proteins, i.e., at least the RNA polymerase, the N protein and the P protein, continually in time. According to a particular embodiment of the invention, the integrity, i.e., the primary amino acid sequence, of these three proteins is maintained, ensuring that the proteins expressed or produced are always the same.

The stable production of the RNA polymerase, the N protein and the P protein is independent of the presence in the cell, of plasmid(s) carrying the coding sequence of these proteins. Therefore, even though plasmids may be used at a particular step of the in vitro or ex vivo cell manipulation, the resulting recombinant cells, which stably produce the three or the at least three proteins, do not contain plasmids anymore. In that way, the expression is said plasmid-independent, in contrast to recombinant cells in which protein expression is driven by plasmid(s).

In a particular embodiment of the invention, the stable expression of the RNA polymerase, of the N protein and of the P protein, does not require the presence of a drug, such as an antibiotic, i.e., the stable expression does not require a selection pressure. Therefore, the stable production does not require the mandatory presence of plasmid(s) for survival, said plasmid bearing the coding sequence of the protein(s) to express.

Another feature of the invention is that each of the at least three proteins, i.e., at least the RNA polymerase, the N protein and the P proteins are produced or expressed at similar level over time. "Similar lever" as used herein means that the expression of each of the three proteins is steady during the cell life, even after cell division, with a variation in expression level which is not more than about 30%, particularly not more than about 20% and preferably not more than about 10%, as compared to mean expression calculated at different times of the cell life.

The RNA polymerase expressed or produced by the cells of the invention is any polymerase suitable for synthesizing non-segmented negative-sense single-stranded viral RNA (vRNA) derived from a cDNA clone, in a rescue system. The nature of the polymerase depends essentially on the nature of the RNA promoter polymerase sequence located in the cDNA clone of the non-segmented negative-strand single-stranded RNA virus, used for the rescue system (also called reverse genetics, or de novo synthesis of negative-sense RNA viruses from cloned cDNA). As an example, the RNA polymerase is the T7 phage RNA polymerase, or its nuclear form (nlsT7).

The expressions "N protein" and "P protein" refer respectively to the nucleoprotein (N) of a non-segmented negative-strand single-stranded RNA virus and the phosphoprotein (P) of a non-segmented negative-strand single-stranded RNA virus. Examples of families subfamilies, genius or species of non-segmented negative-strand single-stranded RNA viruses from which the N and/or P protein can be derived are listed in Table 1.

In a particular embodiment, the N and P proteins of a non-segmented negative-strand RNA virus are from the same virus, either from the same virus strain or from different virus strains. In another embodiment, the N and P proteins of a non-segmented negative-strand RNA virus are from different non-segmented negative-strand RNA virus.

TABLE 1

Family, subfamily, genus and species of several non-segmented negative-strand RNA viruses (NNV) of the order Mononegavirale.

| Family | Subfamily | Genus | Species | Abbreviation |
|---|---|---|---|---|
| Rhabdoviridae | / | Vesiculovirus | Vesicular stomatitis virus | VSV |
| | | Lyssavirus | Rabies virus | RV |
| Paramyxoviridae | Paramyxovirinae | Morbillivirus | Measles virus | MV |
| | | | Rinderpest virus | RPV |
| | | | Canine distemper virus | CDV |
| | | Respirovirus | Sendai virus | SeV |
| | | | Human parainfluenza virus type 3 | hPIV3 |
| | | | Bovine parainfluenza virus type 3 | bPIV3 |
| | | Rubulavirus | Simian virus type 5 | SV5 |
| | | | Mumps virus | |
| | | | Human parainfluenza virus type 2 | hPIV2 |
| | | | Newcastle disease virus | NDV |
| | Pneumovirinae | Pneumovirus | Human respiratory syncytial virus | hRSV |
| | | | Bovine respiratory syncytial virus | bRSV |
| Filoviridae | / | Ebola-like viruses | Ebola virus | / |

In particular embodiment, the N and P proteins are derived from a *Mononegavirus*, preferably a Paramyxoviridae virus, preferably a Paramyxovirinae virus, and most preferably a *Morbillivirus* virus. As an example of *Morbillivirus* is the Measles virus (MV), in particular an attenuated non immunosuppressive strain, e.g. an approved strain for a vaccine, and especially the Schwarz MV strain or the Edmonston (Ed) strain or a derivative from these strains. An approved strain for a vaccine is defined by the FDA (US Food and drug administration) as having the following provisions: safety, efficacy, quality and reproducibility, after rigorous reviews of laboratory and clinical data (www.fda.gov/cber/vaccine/vacappr.htm).

Each time reference is made in the present application, to non-segmented negative strand RNA virus, it possibly applies in particular to the specific viruses listed herein, and especially to a measles virus, in particular to the Schwarz strain.

The expression "functional derivatives thereof" refers to any functional variants including fragments of the RNA polymerase and/or the N protein and/or the P protein, provided that the functional derivatives keep the activity of the protein they are derived from, at least as a ribonucleoprotein complex (RNP complex), functional in transcription and replication in a virus genome, in a rescue system enabling the production of non-segmented negative-sense RNA viruses from cloned cDNA.

A functional variant is defined by a nucleic acid encoding said functional variant proteins, having at least one of the following features:

the nucleic acid encoding the functional variant hybridizes in high stringency conditions with a nucleic acid encoding the wild-type (reference) RNA polymerase or with the N protein and the P protein of an identified non-segmented negative-strand RNA strain or virus. High stringency conditions are defined by Sambrook et al. in Molecular Cloning: a laboratory manual (1989). These conditions of high stringency encompass: use a pre-washing solution for the nitrocellulose filters 5×SSC, 0.5% SDS, 1.0 mM EDTA (pH 8.0), hybridisation conditions of 50% formamide, 6×SSC at 42° C. and washing conditions at 68° C., 0.2×SSC and 0.1% SDS. Protocols are known to those having ordinary skill in the art. Moreover, the skilled artisan will recognize that the temperature and wash solution salt concentration can be adjusted as necessary according to experimental constraints;

the nucleic acid encoding the functional variant presents at least 80%, preferably 90%, more preferably 95% or even 99% similarity with a native nucleic acid encoding the RNA polymerase, the N protein or the P protein, said similarity being calculated over the entire length of both sequences;

the nucleic acid encoding the functional variant differs from a native nucleic acid encoding the RNA polymerase, the N protein or the P protein by at least one nucleotide substitution, preferably 1, 2, 3, 4 or 5 substitution(s), optionally conservative substitutions (nucleotide substitution(s) not altering the amino acid sequence), by at least one nucleotide deletion or addition, preferably 1, 2, 3, 4 or 5 nucleotide(s) deletion or addition.

A fragment is defined in the present application as a part of the full-length RNA polymerase, of the N protein or of the P protein, as long as the fragment has the same activity as the entire protein from which it is derived, at least as a ribonucleoprotein complex (RNP complex) as disclosed herein. In a particular embodiment, the fragment represents at least 70%, particularly 80%, and more particularly 90% or even 95% of the full-length protein.

Accordingly, where reference is made herewith to RNA polymerase, N or P proteins or to their coding sequences, the description similarly applies to their functional derivatives as defined herein.

According to a particular embodiment a recombinant cell of the invention comprises, integrated in its genome, at least one copy of a nucleic acid encoding a RNA polymerase, at least one copy of a nucleic acid encoding a N protein of a non-segmented negative-strand RNA virus, and at least one copy of a nucleic acid encoding a P protein of a non-segmented negative-strand RNA virus. Optionally, the nucleic acids encoding the three proteins above are, each or at least one of these, under the control of transcription regulatory element(s) The expression "integrated in the genome" means that the at least one copy of a nucleic acid under the control of transcription regulatory element(s) is located within the genome of the recombinant cells, under conditions enabling said cells to stably express the protein encoded by the nucleic acid. In a particular embodiment, the recombinant cell of the invention comprises further, integrated in its genome, at least one copy of a nucleic acid encoding a L protein of a non-segmented negative-strand RNA virus.

"at least one copy" means that the nucleic acid encoding the RNA polymerase and/or the N protein and/or the P protein and/or the L protein may be present in one or several copies, preferably exactly or at least 2, 3, 4, 5, 6, 7, 8, 9, 10 copies, or more, depending on the expression level required for each of these proteins.

In a particular embodiment of the invention, the cells of the invention also contain at least one copy of a DNA flap integrated into the cell genome. A DNA flap is a nucleotide sequence of retroviral especially lentiviral, or retroviral-like origin comprising two essential regions, i.e., the cPPT (central polypurine tract) and the CTS (cis-acting termination region) regions, wherein the cPPT and CTS regions induce a three-stranded DNA structure during replication of DNA containing them (previously defined in Zennou et al., 2000; and in applications WO99/55892 and WO01/27300). In a particular embodiment, the DNA flap is inserted immediately upstream of the internal promoter enabling transcription of the nucleic acids encoding the RNA polymerase, the N protein, the P protein and possibly the L protein. The DNA flap (cPPT-CTS) is inserted into the retroviral-derived vectors of the invention in a functional orientation i.e., the cPPT region is in 5' with respect to the CTS region (the 5' part of the vector corresponding to the LTR containing the primer binding site (PBS), and the 3' part of the vector corresponding to the region containing the 3'PPT).

A DNA flap suitable for the invention may be obtained from a retrovirus especially from a lentivirus or retrovirus-like organism such as retrotransposon, prepared synthetically (chemical synthesis) or by amplification of the DNA flap from any retrovirus especially from a lentivirus nucleic acid such as by Polymerase chain reaction (PCR). The DNA flap may be obtained from a retrovirus, especially a lentivirus, especially a human retrovirus or lentivirus and in particular a HIV retrovirus, the CAEV (Caprine Arthritis Encephalitis Virus) virus, the EIAV (Equine Infectious Anaemia Virus) virus, the VISNA virus, the SIV (Simian Immunodeficiency Virus) virus or the FIV (Feline Immunodeficiency Virus) virus. In a more preferred embodiment, the DNA flap is obtained from an HIV retrovirus, for example HIV-1 or HIV-2 virus or any different isolate of these two types.

Preferred DNA flap comprises or consists in the sequences as defined in SEQ ID NO: 1 to 7. It is noteworthy that the DNA flap is used isolated from its natural (viral genome) nucleotide context i.e., isolated from the pol gene in which it is naturally contained in a lentivirus. Therefore, the DNA flap is used, in the present invention, deleted from the unnecessary 5' and 3' parts of the pot gene and is recombined with sequences of different origin. According to a particular embodiment, a DNA flap has a nucleotide sequence of about 90 to about 150 nucleotides, in particular from about 100 to about 140 nucleotides.

The invention also concerns a cell obtainable by recombination of its genome with (1) an expression vector comprising a DNA flap, and at least one copy of a nucleic acid encoding a RNA polymerase, (2) an expression vector comprising a DNA flap, and at least one copy of a nucleic acid encoding a N protein of a non-segmented negative-strand RNA virus, and (3) an expression vector comprising a DNA flap, and at least one copy of a nucleic acid encoding a P protein of a non-segmented negative-strand RNA virus. Definitions given above apply to these cells.

The invention is also directed to a cell obtainable by recombination of its genome with (1) an expression vector comprising a DNA flap, and at least one copy of a nucleic acid encoding a RNA polymerase, (2) an expression vector comprising a DNA flap, and at least one copy of a nucleic acid encoding a N protein of a non-segmented negative-strand RNA virus, (3) an expression vector comprising a DNA flap, and at least one copy of a nucleic acid encoding a P protein of a non-segmented negative-strand RNA virus and (4) an expression vector comprising a DNA flap, and at least one copy of a nucleic acid encoding a L protein of a non-segmented negative-strand RNA virus. Definitions given above apply to these cells. Definitions given above apply to these cells.

The invention encompasses a cell obtainable by recombination of its genome with an expression vector comprising at least one copy of a nucleic acid encoding a RNA polymerase, at least one copy of a nucleic acid encoding a N protein of a non-segmented negative-strand RNA virus, at least one copy of a nucleic acid encoding a P protein of a non-segmented negative-strand RNA virus and a DNA flap. Definitions given above apply to these cells. In a particular embodiment, the expression vector comprises further at least one copy of a nucleic acid encoding a L protein of a non-segmented negative-strand RNA virus.

The invention is also directed to an expression retroviral-derived vector comprising a DNA flap as described above and at least one nucleic acid encoding a protein necessary for the rescue of a non-segmented negative-strand RNA virus. In a particular vector of the invention, the nucleic acid encodes a protein that is selected from the group consisting of a RNA polymerase, a N protein of a non-segmented negative-strand RNA virus, a P protein of a non-segmented negative-strand RNA virus and a L protein of a non-segmented negative-strand RNA virus.

The term "genome" refers to any nucleic acid molecule, whose presence into the cell is not dependent upon pressure selection i.e., whose presence into the cell is permanent and/or does not depend from environmental conditions. The term "genome" does not encompass plasmids. Primarily, the term "genome" refers to nucleic acid molecules present into the cell nucleus (nuclear genome), by opposition to nucleic acid molecules present into the cytoplasm, and encompasses for example chromosomes. In particular embodiment, the term "genome" also includes nucleic acid molecules present in particular cell compartments, such as organelles, for example mitochondria (mitochondrial genome) or chloroplasts (chloroplast genome). In a particular embodiment, the genome is from a eukaryotic cell.

A retroviral-derived vector, and particularly a lentiviral-derived vector and more particular a HIV-1-derived vector, is a viral genome that comprises the elements necessary for the retrotranscription, particularly the LTRs possibly mutated including deleted in part especially deleted in the U3 region, as illustrated below and advantageously the DNA flap. These LTR and DNA flap regions may be the only sequences of retroviral, especially lentiviral origin in the retroviral-derived expression vector. In no case, the retroviral-derived vector contains the nucleotide sequences encoding the full-length retroviral proteins. In a particular embodiment of the invention, the retroviral-derived vector comprises or consists of a DNA flap and at least one nucleic acid encoding a protein necessary for the rescue of a non-segmented negative-strand RNA virus as described herein, as well as the LTRs of the corresponding viral genome.

An expression vector of the invention comprises a DNA flap and a nucleic acid encoding a RNA polymerase or functional part thereof. Such a vector may be the plasmid HIV-1-TRIPΔU3.CMV-T7 deposited with the CNCM on Dec. 14, 2006, under number 1-3702, which is an HIV-1 expression vector comprising a DNA flap (TRIP), a LTR deleted in the promoter and the enhancer of the U3 domain, a CMV promoter and a nucleic acid encoding the T7 phage RNA polymerase, especially one having the sequence SEQ ID NO: 8, or the plasmid HIV-1-TRIPΔU3.CMV-nlsT7 deposited with the CNCM on Dec. 14, 2006, under number I-3703, which is an HIV-1 expression vector comprising a DNA flap (TRIP), a LTR deleted in the promoter and the enhancer of the U3 domain, a CMV promoter and a nucleic acid encoding the nuclear form of the T7 phage RNA polymerase, especially one having the sequence SEQ ID NO: 10.

An expression vector of the invention comprises a DNA flap and a nucleic acid encoding a N protein of a non-segmented negative-strand RNA virus. Such a vector may be the plasmid HIV-1-TRIPΔU3.CMV-N deposited with the CNCM on Dec. 14, 2006, under number I-3700, which is an HIV-1 expression vector comprising a DNA flap (TRIP), a LTR deleted in the promoter and the enhancer of the U3 domain, a CMV promoter and a nucleic acid encoding the N protein of the MV Schwarz, especially one having the sequence SEQ ID NO: 12.

An expression vector of the invention comprises a DNA flap and a nucleic acid encoding a P protein of a non-segmented negative-strand RNA virus. Such a vector may be the plasmid HIV-1-TRIPΔU3.CMV-P deposited with the CNCM on Dec. 14, 2006, under number I-3701, which is an HIV-1 expression vector comprising a DNA flap (TRIP), a LTR deleted in the promoter and the enhancer of the U3 domain, a CMV promoter and a nucleic acid encoding the P protein of the MV Schwarz, especially one having the sequence SEQ ID NO: 14.

Another expression vector of the invention comprises a nucleic acid encoding an L protein of a non-segmented negative-strand RNA virus. Such a vector may be the pEMC-LSchw plasmid, deposited with the CNCM on Dec. 18, 2007, under number I-3881. One particular nucleic acid encoding an L protein is the one having SEQ ID NO:19.

The vectors CNCM I-3700 to 3703 quoted above all are contained in E. coli (JM109) strain, cultivated in LB medium supplemented with ampicilin (100 µg/ml) at 37° C. with shaking.

The invention relates to each and any nucleotide fragment contained in the polynucleotides inserted in the deposited plasmids referred to herein, and especially to each and any region suitable to design the insert, according to the present disclosure. It relates also to the use of these fragments for the construction of plasmids of the invention.

The four plasmids above are examples of vectors that can be used in the recombination of cells to obtain recombinant cells of the invention. However, these examples do not constitute limitations of the invention; therefore, and as described above, the N and P proteins (or their functional derivatives) can be derived from any non-segmented negative-strand RNA virus, the T7 polymerase can be any RNA polymerase, the CMV promoter can be any promoter, the TRIP DNA flap can be any DNA flap and the HIV-1 expression vector can be any vector and particularly any viral vector.

Other expression vectors of the invention comprise a DNA flap and a nucleic acid encoding a L protein of a non-segmented negative-strand RNA virus, or comprise a DNA flap and nucleic acid(s) encoding a RNA polymerase, a N protein of a non-segmented negative-strand RNA virus, a P protein of a non-segmented negative-strand RNA virus and optionally a L protein of a non-segmented negative-strand RNA virus.

The term "expression vector" indicates that, besides the elements explicitly mentioned, the vector comprises all the elements necessary to drive the expression of the nucleic acid(s) encoding the proteins of interests (expression regulatory elements), and particularly transcription regulatory elements. "Transcription regulatory element" defines any DNA regions involved in the regulation of transcription of the nucleic acid(s) integrated in the genome, and encompasses a promoter, such as CMV, EF1alpha or mPGK (murine phosphoglycerate kinase) or more generally any promoter suitable for insertion in a fetroviral, especially lentiviral vector, enhancer or cis-acting regulatory elements. These elements and particularly the promoter are chosen depending upon the nature of the recombinant cells. The determination of the suitable promoter, according to the expression level sought or to the recombined cell, makes part of the knowledge of the person skilled in the art. It is noteworthy that, when the recombinant cell contains several heterologous nucleic acids (also designated polynucleotides) encoding the proteins of interest, said transcription regulatory element(s) may be unique for all the nucleic acids or shared by some of them or in contrast each nucleic acid may be associated with a particular transcription regulatory element. In the latter case, the several transcription regulatory elements may be similar or different.

The presence of the DNA flap, in all the vectors used in the recombination step, leads to the formation of a DNA triplex structure (three stranded) at the DNA flap position (the triplex structure consisting of the region between the cPPT and the CTS domains including the CTS domain), enabling the import of the nucleic acid bearing the DNA flap into the nucleus of the cell (throughout nucleus membrane pore) and further the integration into the genome of this cell. The DNA flap acts as a cis-determinant of the vector nuclear import. In a first aspect, the presence of the DNA flap is of great interest for the recombination and the integration of nucleic acid(s) into non-dividing cells, since in the absence of cell division (and membrane disintegration), the import (and thus integration of nucleic acids into the cell genome) is only identified as a residual activity; therefore, the vectors containing the DNA flap are non-replicative retroviral vectors able to transduce non-dividing cells. In a second aspect, the presence of the DNA flap is also of great interest for the recombination and the integration of nucleic acid into dividing cells, by considerably improving the percentage of cells in which the nucleic acid containing the DNA flap is integrated. The insertion of the DNA flap sequence in an expression vector, as described in the present specification, strongly increases gene transfer in vitro and in vivo by stimulating nuclear import of vector DNA (Sirven et al, 2001; Zennou et al, 2001). HIV vectors including the DNA flap sequence (TRIP vectors) are able to transduce primary B and T cells, macrophages, dendritic cells, etc with a tenfold higher efficiency than other HIV vectors that lack the DNA flap. A transduction of 80-90% of cells can be routinely obtained.

Following the recombination by the vector(s) containing a DNA flap and nucleic acid(s) encoding the at least three proteins of interest and the integration of these nucleic acids in the genome, the recombinant cells stably produce the RNA polymerase, the N protein and the P protein.

The expression vectors of the invention, used to obtain the recombinant cells of the present invention, are viral vectors, and particularly viral expression vector, such as retroviral-derived, especially lentiviral-derived vectors such as HIV-, FIV- or SIV-derived vectors. More particularly, the lentiviral-derived vector is a human lentiviral-derived vector such as an HIV expression vector, particularly HIV-1 or HIV-2-derived vector. In a preferred embodiment, the viral vector is a HIV expression vector comprising a DNA flap as described above and at least one nucleic acid encoding the at least three proteins of interest. HIV vectors are classical replacement retroviral vectors in which substantially the entire coding viral sequences are replaced by the sequence to be transferred. HIV vectors express therefore only the heterologous nucleic acid(s) contained between the two HIV LTRs or mutated LTRs and under the control of the DNA flap. These vectors can thus accommodate large polynucleotides having up to 5-6 kb. A particular embodiment of the invention is a HIV expression virus as described above, and most particularly a HIV-1 expression vector, wherein a HIV-1 LTR is deleted for the promoter and the enhancer of the U3 domain (ΔU3). This particular deletion has been previously shown to increase the expression of the nucleic acid(s) contained in the vector, and particularly when associated with a promoter.

In a particular embodiment, the recombinant cell of the invention is obtainable by recombination of its genome either with plasmids HIV-1-TRIPΔU3.CMV-T7, HIV-1-TRIPΔU3.CMV-N and HIV-1-TRIPΔU3.CMV-P, or with plasmids HIV-1-TRIPΔU3.CMV-nlsT7, HIV-1-TRIPΔU3.CMV-N and HIV-1-TRIPΔU3.CMV-P.

Cells of the invention can be prokaryotic or eukaryotic cells, particularly animal or plant cells, and more particularly mammalian cells such as human cells or non-human mammalian cells. In a particular embodiment, cells, before recombination of its genome, are isolated from either a primary culture or a cell line. Cells of the invention may be dividing or non-dividing cells. As an example of cells that can be recombined to provide the recombinant cells of the invention are HEK 293 (human embryonic kidney) cells, which cell line 293 is deposited with the ATCC under No. CRL-1573. In a particular embodiment, human cells are not germinal cells and/or embryonic stem cells.

Recombinant cells of the invention can be the 293-T7-NP cell line deposited with the COLLECTION NATIONALE DE CULTURES DE MICROORGANISMES (CNCM), 25 rue du Docteur Roux, F-75724 PARIS Cedex 15, FRANCE on Jun. 14, 2006, under number I-3618 i.e., HEK-293 cells recombined with the plasmids HIV-1-TRIPΔU3.CMV-T7, HIV-1-TRIP ΔU3.CMV-N and HIV-1-TRIPΔU3.CMV-P. Another example of recombinant cells of the invention are the 293-nlsT7-NP MV cell line deposited with the COLLECTION NATIONALE DE CULTURES DE MICROORGANISMES (CNCM), 25 rue du Docteur Roux, F-75724 PARIS Cedex 15, FRANCE on Aug. 4, 2006, under number I-3662 i.e., HEK-293 cells recombined with plasmids HIV-1-TRIPΔU3.CMV-nlsT7, HIV-1-TRIPΔU3.CMV-N and HIV-1-TRIPΔU3.CMV-P.

In a further embodiment of the invention, the recombinant cells of the invention are further recombined by an expression vector comprising a nucleic acid encoding a RNA polymerase large protein (L) of a non-segmented negative-strand RNA virus. The expression of the L protein may be temporary and driven by a plasmid not containing DNA flap, or in contrast be stable and driven by a vector containing a DNA flap as defined above. The recombination by a plasmid or vector bearing the at least one copy of the nucleic acid encoding the L protein may be simultaneous to or subsequent to the recombination by the vector(s) containing the coding sequence(s) of the RNA polymerase, the N protein and the P protein.

Therefore, the present invention also refers to a cell stably producing a RNA polymerase, a N protein of a non-segmented negative-strand RNA virus and a P protein of a non-segmented negative-strand RNA virus, or functional derivatives thereof, and producing, stably or not, a L protein of a non-segmented negative-strand RNA virus.

The L protein is derived from any non-segmented negative-strand RNA virus quoted in Table 1. In a particular embodiment, the L protein is from the same non-segmented negative-strand RNA virus as the N protein and/or the P protein, and particularly from the same virus strain. In another embodiment, the L protein is from a different non-segmented negative-strand RNA virus than the N protein and/or the P protein.

In particular embodiment, the L protein is from a Paramyxoviridae virus, preferably a Paramyxoviridae virus, and most preferably a *Morbillivirus* virus. As an example of *Morbillivirus* is the Measles virus (MV), in particular an attenuated non immunosuppressive strain, e.g. an approved strain for a vaccine, and especially the Schwarz MV strain, or even the Edmonston (Ed) strain. A particular L protein is the one of the MV virus (SEQ ID NO: 16) or the one encoded by the sequence inserted in pEMC-LSchw plasmid and especially the sequence found between nucleotides 1425 and 7976 of SEQ ID NO:19.

In a particular embodiment, the sequence of the L protein must not be modified with respect to the wild type L protein and must be functional i.e., enabling the production of particles or virus when transcomplemented with N and P proteins and a T7 polymerase in a host cell. A test to determine the effective functionality of a clone bearing the L protein is carried out by transfecting a competent cell with vector(s) encoding the N protein, the P protein and the T7 (or nlsT7) polymerase, a vector encoding the L protein to be tested, and a minigenome comprising a leader, a promoter, a reporter gene (such a GFP) and a trailer. The functionality of the L clone is revealed by the production of particles expressing the reporter gene.

The present invention also describes a cell according to the present specification further recombined with a non-segmented negative-strand cDNA clone of a non-segmented negative strand RNA virus i.e., the antigenomic RNA (+) strand of the virus genome. "cDNA" used for the description of the nucleotide sequence of the molecule of the invention merely relates to the fact that originally said molecule is obtained by reverse transcription of the genomic (−) RNA genome of viral particles of a non-segmented negative strand RNA virus, particularly of the measles virus, and most preferably the full-length genomic (−) RNA genome of viral particles of a non-segmented negative strand RNA virus. This should not be regarded as a limitation for the methods used for the preparation of this cDNA clone. The invention thus encompasses, within the expression "cDNA", every DNA provided it has the above defined nucleotide sequence. Purified nucleic acids, including DNA, or plasmids are thus encompassed within the meaning cDNA according to the invention, provided said nucleic acid, especially DNA fulfils the above-given definitions.

In a particular embodiment, the cDNA clone of a non-segmented negative strand RNA virus contains, upstream of the viral sequences, transcription regulatory elements. In a preferred embodiment, these elements are the same as the one(s) located in the expression vector(s) comprising the N, P and/or L proteins described above. In a more preferred embodiment, the element is a T7 RNA polymerase promoter.

In an embodiment, the cDNA clone of a non-segmented negative-strand RNA virus is from the same non-segmented negative-strand RNA virus as the N protein and/or the P protein and/or the L protein, and particularly from the same virus strain. In another embodiment, the cDNA clone of a non-segmented negative strand RNA virus is from a different non-segmented negative-strand RNA virus than the N protein and/or the P protein and/or the L protein.

In particular embodiment, the cDNA clone is from a non-segmented negative strand RNA virus, such as a Paramyxoviridae virus, preferably a Paramyxovirinae virus, and most preferably a *Morbillivirus* virus. As an example of *Morbillivirus* is the Measles virus (MV), in particular an attenuated non immunosuppressive strain, e.g. an approved strain for a vaccine, and especially the Schwarz MV strain or the Edmonston (Ed) strain. Moreover, the nucleotide sequence of the non-segmented negative-strand cDNA clone may be modified as compared to the wild type strain or virus, such a defined below.

The invention also concerns cultures of cells wherein said cells are those defined throughout the specification, and particularly cultures of cells stably producing a RNA polymerase, a nucleoprotein (N) of a non-segmented negative-strand RNA virus and a phosphoprotein (P) of a non-segmented negative-strand RNA virus, or functional derivatives thereof. In another embodiment, the invention also concerns cultures of cells stably producing a RNA polymerase, a N protein of a non-segmented negative-strand RNA virus and a P protein of a non-segmented negative-strand RNA virus, or functional derivatives thereof, and producing, stably or transitory, a L protein of a non-segmented negative-strand RNA virus or functional derivatives thereof.

In an embodiment, the cells culture to be recombined is a primary culture i.e., a culture prepared from cells or tissues directly obtained from an animal (optionally non-human) or a plant. In another embodiment, the cells culture to be recombined is a cell line i.e., a population of cells resulting from the first subculture of a primary culture or from subsequent serial passaging of the cells.

In another aspect, the present invention also relates to various methods to produce infectious, recombinant, non-segmented negative-strand virus, using the cells of the invention.

A first method to produce infectious, recombinant, non-segmented negative-strand virus comprises or consists in:
  a. recombining a cell or a culture of cells stably producing a RNA polymerase, a nucleoprotein (N) of a non-segmented negative-strand RNA virus and a polymerase cofactor phosphoprotein (P) of a non-segmented negative-strand RNA virus, with cDNA clone of a non-segmented negative strand RNA virus and with a vector comprising a nucleic acid encoding a RNA polymerase large protein (L) of a non-segmented negative-strand RNA virus,
  b. transferring said recombinant cell or culture of recombinant cells onto cells competent to sustain the replication and production of non-segmented negative-strand RNA virus, and
  c. recovering the infectious, recombinant, non-segmented negative-strand RNA virus from the co-culture of step b.

A second method according to the invention is a method to produce infectious, recombinant, non-segmented negative-strand RNA virus comprising or consisting of:
  a. recombining a cell or a culture of cells stably producing a RNA polymerase, the nucleoprotein (N) of a non-segmented negative-strand RNA virus and the polymerase cofactor phosphoprotein (P) of a non-segmented negative-strand RNA virus, with a cDNA clone of a non-segmented negative strand RNA virus and with a vector comprising a nucleic acid encoding a RNA polymerase large protein (L) of a non-segmented negative-strand RNA virus, and
  b. recovering the infectious, recombinant, non-segmented negative-strand RNA virus from said recombinant cell or culture of recombinant cells.

As used herein, "recombining" means introducing at least one polynucleotide into a cell, for example under the form of a vector, said polynucleotide integrating (entirely or partially) or not integrating into the cell genome (such as defined above). According to a particular embodiment recombination can be obtained with a first polynucleotide which is a cDNA clone of a non-segmented negative strand RNA virus, whose definition, nature and optional modifications are discussed elsewhere in the present specification. Recombination can, also or alternatively, encompasses introducing a polynucleotide which is a vector encoding a RNA polymerase large protein (L) of a non-segmented negative-strand RNA virus, whose definition, nature and stability of expression has been described herein.

In these methods, the cell or a culture of cells stably producing a RNA polymerase, a nucleoprotein (N) of a non-segmented negative-strand RNA virus and a polymerase cofactor phosphoprotein (P) of a non-segmented negative-strand RNA virus is a cell as defined in the present specification or a culture of cells as defined in the present specification, i.e., are also recombinant cells to the extent that they have been modified by the introduction of one or more polynucleotides as defined above. In a particular embodiment of the invention, the cell or culture of cells, stably producing the RNA polymerase, the N and P proteins, does not produce the L protein of a non-segmented negative-strand RNA virus or does not stably produce the L protein of a non-segmented negative-strand RNA virus, e.g., enabling its transitory expression or production.

"Transfer" as used herein refers to the plating of the recombinant cells onto a different type of cells, and particularly onto monolayers of a different type of cells. These latter cells are competent to sustain both the replication and the production of infectious, recombinant, non-segmented negative-strand RNA viruses i.e., respectively the formation of infectious viruses inside the cell and possibly the release of these infectious viruses outside of the cells. This transfer results in the co-culture of the recombinant cells of the invention with competent cells as defined in the previous sentence. The above transfer may be an additional, i.e., optional, step when the recombinant cells are not efficient virus-producing culture i.e., that infectious viruses can not be efficiently recovered from these recombinant cells. This step is introduced after further recombination of the recombinant cells of the invention with a cDNA clone of a non-segmented negative-strand RNA virus, and optionally a vector comprising a nucleic acid encoding a RNA polymerase large protein (L) of a non-segmented negative-strand RNA virus.

In a particular embodiment of the invention, a transfer step is required since the recombinant cells, usually chosen for their capacity to be easily recombined are not efficient enough in the sustaining and production of recombinant infectious viruses. In said embodiment, the cell or culture of cells of step a. of the above-defined methods is a recombinant cell or culture of recombinant cells according to the invention, particularly recombinant HEK-293 cells such as the 293-T7-NP cell line deposited with the CNCM on Jun. 14, 2006, under number I-3618 or 293-nlsT7-NP MV cell line deposited with the CNCM on Aug. 4, 2006, under number I-3662.

Cells competent to sustain the replication and production of non-segmented negative-strand RNA virus may be any cell type that can be co-cultivated with the recombinant cells of the invention but not necessarily cells of the same Kingdom, Phylum, Class, Order, Family, Genus or Species. Examples of competent cells are Vero (African green monkey kidney) cells or CEF (chick embryo fibroblast) cells. CEF cells can be prepared from fertilized chicken eggs as obtained from EARL Morizeau (8 rue Moulin, 28190 Dangers, France), from any other producer of fertilized chicken eggs or from MRC5 cells (ATCC CCL171; lung fibroblast).

In another embodiment of the invention, the transfer step is not needed and thus not carried out. This is one of the advantages of the present invention to provide a method to produce infectious, recombinant, non-segmented negative-strand RNA viruses that is easy to carry out, faster and cheaper than the conventional methods and enabling the recovery of recombinant infectious viruses free of contaminants. This can be achieved with the recombinant cells of the invention that have the features of:
- stably producing a RNA polymerase, a nucleoprotein (N) of a non-segmented negative-strand RNA virus and a phosphoprotein (P) of a non-segmented negative-strand RNA virus, and
- from which infectious recombinant viruses can be efficiently recovered, without contaminations by unwanted viruses and/or other type of cells.

The "Recovery of infectious recombinant virus" as used herein refers to any means by which the infectious viruses, previously produced by the cells, are released from the cells, and isolated from the cultured cells. The recovery is said to be "direct" when the infectious recombinant viruses are recovered from recombinant cells of the invention, without involvement of other cell type(s). In contrast, the recovery is said to be "indirect" when the infectious recombinant viruses are recovered via another cell type than the recombinant cells of the invention. As mentioned earlier, the present invention is the first to report the direct recovery of infectious, recombinant, non-segmented negative-strand RNA virus.

In particular methods of the invention, the recombining step does not comprise the steps of recombining a cell or a culture of cells stably producing a RNA polymerase, a nucleoprotein (N) of a non-segmented negative-strand RNA virus and a polymerase cofactor phosphoprotein (P) of a non-segmented negative-strand RNA virus, with a vector comprising a nucleic acid encoding a RNA polymerase large protein (L) of a non-segmented negative-strand RNA virus. In that case, the recombinant cells of the invention have been selected for their capacity to express the L protein and especially have been previously recombined with a vector comprising a nucleic acid encoding a RNA polymerase large protein (L), the nucleic acid encoding the L protein being integrated in the cell genome or not.

When appropriate vectors bearing accessory proteins (non-P, non-L or non-N proteins, or non-RNA polymerase) may optionally be used in the methods of the invention, particularly when a genome or a cDNA clone, deleted for these proteins, is used. Such accessory proteins are the C protein, the V protein, the NS1 protein, the NS2 protein, the M protein, the M2 protein and/or the SH proteins. The vector(s) bearing the coding sequences of these accessory proteins may optionally comprises a cDNA flap as defined above.

The stability of the production of the RNA polymerase, N protein and P protein in the recombinant cells of the invention leads to some advantages according to the methods previously described in the art:
- the method of the invention does not necessarily comprise a transfer step;
- the method does not comprise heat shock step as reported in Parks et al. (1999). Indeed, this step has been shown to improve the efficiency of the synthesis of viral N and P proteins, as well as RNA polymerase, which proteins are synthesized from nucleic acids borne on plasmids. In the present invention, however, the nucleic acids are integrated into the cell genome, and the expression of these proteins has been shown to be stable, and/or at a level appropriate to initiate the de novo encapsidation.
- the method produces large quantities of infectious viruses, since the production of the RNA polymerase, N protein and P protein is stable, and not dependent on their expression from plasmids. Therefore, about 100-400 out of $10^6$ recombined cells transmit infectious viruses after recombination (number of rescue events). This is mostly superior to the 1-6 out of $10^6$ transfected cells obtained with the method of Radecke et al. (1995). In a particular embodiment of the method, the number of rescue events, for $10^6$ recombined cells, is more than 20, more than 50, more than 100, more than 200, more than 300, more than 400 or more than 500.

Finally, another advantage of the invention is the large variety of cells that can be recombined, and used to perform the invention. Indeed, the recombinant cells can be any eukaryotic cell, particularly any mammalian cell, either non-human cell or human cell. In a particular embodiment, the recombinant cells of the invention are human fibroblasts, especially MRC5 cell line (human lung fibroblasts). The invention is particularly useful for cells that do not divide.

According to the invention, the cDNA clone of a non-segmented negative-strand of a RNA virus is from a MV virus, particularly an attenuated virus in particular an attenuated non immunosuppressive strain, e.g. an approved strain for a vaccine, such as the Schwarz MV strain. A cDNA clone is a DNA sequence encoding the full-length antigenome of a non-segmented negative-strand RNA virus.

In a particular embodiment of the invention, the N, P and L proteins as well as the cDNA clone are from the same virus, that can be any virus of Table I, particularly a MV virus as disclosed above such as the Schwarz MV strain of measles virus. The nucleotide sequences of the Edmonston B. strain and of the Schwarz strain have been disclosed in WO 98/13505. Independently of the nature of the N, P and L proteins and the cDNA clone of the non-segmented negative-strand RNA virus, the RNA polymerase is the T7 RNA polymerase. A particular cDNA sequence is the sequence of the cDNA of the Schwarz strain as defined in SEQ ID NO: 18. Such a cDNA can be obtained from pTM-MVSchw, that is a plasmid derived from Bluescript containing the complete sequence of the measles virus, vaccine strain Schwarz, under the control of the promoter of the T7 RNA polymerase. Its size is 18967nt.

Alternatively, the cDNA clone of a non-segmented negative strand RNA virus is derived from any virus of Table I. A particular recombinant measles virus from which the cDNA clone is derived from is the Schwarz strain and especially an approved vaccine Schwarz strain such as that produced under the trademark Rouvax, available from Aventis Pasteur (France).

An "attenuated strain" is defined herein as a strain that is avirulent or less virulent than the parent strain in the same host, while maintaining immunogenicity and possibly adjuvanticity when administered in a host i.e., preserving immunodominant T and B cell epitopes and possibly the adjuvanticity such as the induction of T cell costimulatory proteins or the cytokine IL-12. In a particular embodiment, the attenuated strain is an "approved vaccine strain" i.e., a strain certified for use in vaccine production by one national or regional health authority having granted a marketing approval for this product (legal designation). Accordingly, an "approved vaccine strain" has been shown to be safe, stable and able to provide effective protection (immunogenicity and adjuvanticity). Stability of a strain is measured by assessing that the properties of the strain remain substantially unchanged after numerous passages on the same certified cell line.

"Derived from" as used herein means any cDNA clone whose nucleotide sequence is modified as compared to the one of the wild type virus or strain. This modification may be at least one substitution, deletion or insertion in the nucleotide sequence and particularly in the coding sequence of a protein of the virus or strain. In another embodiment, the nucleotide sequence is modified by the insertion of at least one heterologous nucleic acid(s) i.e., a sequence that is not naturally present in the virus or the strain in which the at least one nucleic acid(s) is inserted or a sequence which is not derived from the antigens of measles viruses. Moreover, the cDNA clone may be modified by deletion of part(s) of the wild-type viral genome, and insertion of heterologous nucleic acids.

In a preferred embodiment, it is pointed out that the derived cDNA clone, consisting or comprising one or several heterologous nucleic acid(s), meets the so-called rule of 6. Therefore, the derived cDNA clone is a polyhexameric length, i.e., is a multiple of six. This requirement is especially achieved for cDNA clones derived from Paramyxoviridae, and in particular measles viruses. Some non-segmented negative-strand RNA viruses do not comply with this rule, as known from the skilled person in the art.

Any heterologous nucleic acid can be inserted in the nucleotide sequence of the cDNA clone, as far as the insertion does not prevent the production of infectious recombinant non-segmented negative-strand virus (permissive sites). In a particular embodiment, the insertion or deletion of the native viral genome provides a polynucleotide which is a multiple of six. Therefore, even though the genome length is not a multiple of six, the modification consists of six or multiple of six deletions and/or insertions.

Therefore, the heterologous nucleic acid sequences may encode one or several peptides able to elicit a humoral and/or cellular immune response (such as CTL or CD4 response) in a determined host, against the organism or organisms especially the pathogenic organism(s), for example the virus, especially retrovirus, flavivirus or coronavirus, of the bacterium or parasites from which it (they) originate(s). Accordingly, the amino acid sequence of such peptide is one which comprises at least one epitope of an antigen, especially a conserved epitope, which epitope is exposed naturally on the antigen or is obtained or exposed as a result of a mutation or modification or combination of antigens. Heterologous nucleic acids, which can be inserted in the cDNA clones, encode especially structural antigens (including antigenic fragments thereof or derivatives of said antigens or fragments) of viruses including retroviruses such as human retroviruses especially lentivirus, in particular HIV-1 or HIV-2, flavivirus or coronavirus envelope, such as envelop or capsid antigen. Particularly, such antigens are especially from envelopes of AIDS viruses including HIV-1 or HIV-2, from capsid of HIV or from envelopes of the Yellow Fever Virus or envelopes from the West Nile Virus, or from envelopes of the Dengue virus (DV), envelopes of the Japanese encephalitis virus (JEV) or envelope of the SARS-associated coronavirus. Other retroviral, flaviviral or coronavirus antigens may however be advantageously used in order to derive recombinant measles viruses capable of eliciting antibodies against said retroviruses or flaviviruses, and/or capable of eliciting the production of neutralizing antibodies against the retrovirus or flaviviruses. In another embodiment, the peptide encoded or encompassed by the heterologous nucleic acid sequences is tumoral antigen or an antigen specifically expressed on the cell surface of cancer cells. According to another embodiment of the invention, the sequences encode multiepitopes or antigens that alternatively or additionally also elicit a cellular immune response against the retrovirus or flaviviruses.

Advantageously, the recombinant measles viruses produced by the method of the invention may also elicit a humoral and/or cellular immune response against measles virus. This response is however not mandatory provided the immune response against the epitope, or multiepitopes or antigens disclosed above is indeed obtained.

In a preferred embodiment of the invention, the heterologous nucleic acid encodes a protein from an HIV retrovirus, particularly an envelope antigen of HIV and especially a peptide derived from an envelope protein or glycoprotein of HIV-1 or HIV-2. The antigens of interest in this respect are especially gp160, gp120 and gp41 of HIV-1 or gp140, GAG or TAT of HIV-1. In a particular embodiment of the invention, the heterologous amino acid sequence is derived from a recombinant gp160, gp120 of HIV-1 or gp140, GAG or TAT of HIV-1.

In another embodiment, the V1, V2 and/or V3 loops of the gp120 (or gp160) antigen are deleted or deleted in part, individually or in combination in such a way that conserved epitopes are exposed on the obtained recombinant gp120 antigen. The V1, V2 and V3 loops of the gp120 (or gp160) antigen of HIV-1 have been especially disclosed in Fields virology (Fields B. N. et al. Lippincott Raven publishers 1996, p. 1953-1977).

In another embodiment, the heterologous nucleic acid encodes a peptide that is derived from the gp120 (or gp160) antigen of HIV-1, wherein the V1, V2 and/or V3 loops of the gp120 (or gp160) antigen are substituted or substituted in part, individually or in combination, in such a way that conserved epitopes are exposed on the obtained recombinant gp120 (or gp160) antigen.

In another embodiment, the heterologous nucleic acid encodes a peptide that is derived from an envelope antigen of HIV-1 especially is derived from the gp120 antigen in such a way that the V1 and V2 loops are deleted and the V3 loop is substituted for the sequence AAELDKWASAA.

In another embodiment, the heterologous nucleic acid encodes a peptide that is gp160ΔV3, gp160ΔV1V2, gp160ΔV1V2V3, gp140ΔV3, gp140ΔV1V2, gp140ΔV1V2V3.

Preferred cDNA clones containing epitopes from HIV, WNV, YFV, DV or JEV are vectors defined in Table II deposited at the CNCM (Collection Nationale de Culture de Microorganismes—Institut Pasteur—Paris, France), and whose features are given below.

TABLE II

| | Vector name | Strain from which the sequence is derived from | Deposit number | Date of deposit |
|---|---|---|---|---|
| Edmonston B. strain | pMV2(EdB)gp160[delta]V3HIV89.6P | | CNCM I-2883 | Jun. 12, 2002 |
| | pMV2(EdB)gp160HIV89.6P | | CNCM I-2884 | |
| | pMV2(EdB)gp140HIV89.6P | | CNCM I-2885 | |
| | pMV3(EdB)gp140[delta]V3HIV89.6P | | CNCM I-2886 | |
| | pMV2(EdB)-NS1YFV17D | | CNCM I-2887 | |
| | pMV2(EdB)-EnvYFV17D | | CNCM I-2888 | |
| Schwarz strain | pTM-MVSchw2-Es (WNV) | | CNCM I-3033 | May 26, 2003 |
| | pTM-MVSchw2-GFPbis | | CNCM I-3034 | |
| | pTM-MVSchw2-p17p24 [delta] myr (HIVB) | | CNCM I-3035 | |
| | pTM-MVSchw3-Tat(HIV89-6p) | | CNCM I-3036 | |
| | pTM-MVSchw3-GFP | | CNCM I-3037 | |
| | pTM-MVSchw2-Es (YFV) | | CNCM I-3038 | |
| | pTM-MVSchw2-gp140 [delta] V1 V2 V3 (HIV89-6) | | CNCM I-3054 | Jun. 19, 2003 |
| | pTM-MVSchw2-gp140 [delta] V3 (HIV89-6) | | CNCM I-3055 | |
| | pTM-MVSchw2-gp160 [delta] V1 V2 V3 (HIV89-6) | | CNCM I-3056 | |
| | pTM-MVSchw2-gp160 [delta] V1 V2 (HIV89-6) | | CNCM I-3057 | |
| | pTM-MVSchw2-Gag SIV239 p17-p24 [delta] myr-3-gp140 (HIV89-6) | | CNCM I-3058 | |
| | pTM-MVSchw2 [EDIII + $M^{1-40}$]WNV (IS-98-ST1) | | CNCM I-3440 | May 26, 2005 |
| | pTM-MVSchw2 [EDIII + apoptoM]DV1 (FGA89) | | CNCM I-3442 | |
| | pTM-MVSchw2 [EDIII] JEV (Nakayama) | | CNCM I-3441 | |

I-2883 (pMV2(EdB)gp160[delta]V3HIV89.6P) is a plasmid derived from Bluescript containing the complete sequence of the measles virus (Edmonston strain B), under the control of the T7 RNA polymerase promoter and containing the gene of the gp160ΔV3+ELDKWAS of the virus SVIH strain 89.6P inserted in an ATU at position 2 (between the N and P genes of measles virus). The size of the plasmid is 21264nt.

I-2884 (pMV2(EdB)gp160HIV89.6P) is a plasmid derived from Bluescript containing the complete sequence of the measles virus (Edmonston strain B), under the control of the T7 RNA polymerase promoter and containing the gene of the gp160 of the SVIH virus strain 89.6P inserted in an ATU at position 2 (between the N and P genes of measles virus). The size of the plasmid is 21658 nt.

I-2885 (pMV2(EdB)gp140HIV89.6P) is a plasmid derived from Bluescript containing the complete sequence of the measles virus (Edmonston strain B), under the control of the T7 RNA polymerase promoter and containing the gene of the gp140 of the SVIH virus strain 89.6P inserted in an ATU at position 2 (between the N and P genes of measles virus). The size of the plasmid is 21094 nt.

I-2886 (pMV3(EdB)gp140[delta]V3HIV89.6P) is a plasmid derived from Bluescript containing the complete sequence of the measles virus (Edmonston strain B), under the control of the T7 RNA polymerase promoter and containing the gene of the gp140ΔV3(ELDKWAS) of the SVIH virus strain 89.6P inserted in an ATU at position 2 (between the N and P genes of measles virus). The size of the plasmid is 21058 nt.

I-2887 (pMV2(EdB)-NS1YFV17D) is a plasmid derived from Bluescript containing the complete sequence of the measles virus (Edmonston strain B), under the control of the T7 RNA polymerase promoter and containing the NS1 gene of the Yellow Fever virus (YFV 17D) inserted in an ATU at position 2 (between the N and P genes of measles virus). The size of the plasmid is 20163 nt.

I-2888 (pMV2(EdB)-EnvYFV17D) is a plasmid derived from Bluescript containing the complete sequence of the measles virus (Edmonston strain B), under the control of the T7 RNA polymerase promoter and containing the Env gene of the Yellow Fever virus (YFV 17D) inserted in an ATU at position 2 (between the N and P genes of measles virus). The size of the plasmid is 20505 nucleotides.

I-3033 (pTM-MVSchw2-Es(WNV)) is a plasmid derived from Bluescript containing a cDNA sequence of the complete infectious genome of the measles virus (Schwarz strain), under the control of the T7 RNA polymerase promoter and expressing the gene of the secreted envelope, (E) of the West Nile virus (WNV), inserted in an ATU.

I-3034 (pTM-MVSchw2-GFPbis) is a plasmid derived from Bluescript containing a cDNA sequence of the complete infectious genome of the measles virus (Schwarz strain), under the control of the T7 RNA polymerase promoter and expressing the gene of the GFP inserted in an ATU.

I-3035 (pTM-MVSchw2-p17p24[delta]myr(HIVB)) is a plasmid derived from Bluescript containing a cDNA sequence of the complete infectious genome of the measles virus (Schwarz strain), under the control of the T7 RNA polymerase promoter and expressing the gene of the gag gene encoding p17p24Δmyrproteins of the HIVB virus inserted in an ATU.

I-3036 (pTMVSchw3-Tat(HIV89-6p)) is a plasmid derived from Bluescript containing a cDNA sequence of the complete infectious genome of the measles virus (Schwarz strain), under the control of the T7 RNA polymerase promoter and expressing the gene of the Tat gene of the virus strain 89.6P inserted in an ATU.

I-3037 (pTM-MVSchw3-GFP) is a plasmid derived from Bluescript containing a cDNA sequence of the complete infectious genome of the measles virus (Schwarz strain) under the control of the T7 RNA polymerase promoter and expressing the gene of the GFP gene inserted in an ATU having a deletion of one nucleotide.

I-3038 (pTM-MVSchw2-Es) (YFV) is a plasmid derived from Bluescript containing a cDNA sequence of the complete infectious genome of the measles virus (Schwarz strain) under the control of the T7 RNA polymerase promoter and expressing the gene of the secreted protein of the Fever virus (YFV) inserted in an ATU.

I-3054 (pTM-MVSchw2-gp140 [delta] V1 V2 V3 (HIV89-6)) is a plasmid derived from Bluescript containing a cDNA sequence of the complete infectious genome of the measles virus (Schwarz strain), under the control of the T7 RNA polymerase promoter and expressing the gene encoding gp140 [delta] V1 V2 (HIV 89-6) inserted in an ATU.

I-3055 (pTM-MVSchw2-gp140 [delta] V3 (HIV89-6)) is a plasmid derived from Bluescript containing a cDNA sequence of the complete infectious genome of the measles virus (Schwarz strain), under the control of the T7 RNA polymerase promoter and expressing the gene encoding gp14 [delta] V3 (HIV 89-6) inserted in an ATU.

I-3056 (pTM-MVSchw2-gp160 [delta] V1 V2 V3 (HIV89-6)) is a plasmid derived from Bluescript containing a cDNA sequence of the complete infectious genome of the measles virus (Schwarz strain), under the control of the T7 RNA polymerase promoter and expressing the gene encoding gp160 [delta] V1 V2 V3 (HIV 89-6) inserted in an ATU.

I-3057 (pTM-MVSchw2-gp160 [delta] V1 V2 (HIV89-6)) is a plasmid derived from Bluescript containing a cDNA sequence of the complete infectious genome of the measles virus (Schwarz strain), under the control of the T7 RNA polymerase promoter and expressing the gene encoding gp160 [delta] V1 V2 (HIV 89-6) inserted in an ATU.

I-3058 (pTM-MVSchw2-Gag SIV239 p17-p24 [delta] myr-3-gp140 (HIV89-6)) is a plasmid derived from Bluescript containing a cDNA sequence of the complete infectious genome of the measles virus (Schwarz strain), under the control of the T7 RNA polymerase promoter and expressing the gene encoding Gag SIV239 p17-p24 [delta] myr-3-gp140 (HIV89-6) inserted in an ATU.

I-3440 (pTM-MvSchw2-[EDIII+$M^{1-40}$] WNV (IS-98-ST1)) is a plasmid derived from PTM containing the cDNA sequence of the complete infectious genome of the measles virus (Schwarz strain) and an additional expression unit located between the P and M genes, this unit containing the nucleotide sequence of the domain III from the envelop protein of the West Nile virus (WNV) (WNV IS-98-ST1) fused to the sequence 1-40 of the membrane protein M.

I-3442 (pTM-MvSchw2-[EDIII+ApoptoM] DV1 (FGA89)) is a plasmid derived from PTM containing the cDNA sequence of the complete infectious genome of the measles virus (Schwarz strain) and an additional expression unit located between the P and M genes, this unit containing the nucleotide sequence of the domain III from the envelop protein of dengue-1 virus (strain FGA89) fused to the apoptotic sequence of the membrane protein M.

I-3441 (pTM-MvSchw2-[EDIII] JEV (Nakayama)) is a plasmid derived from PTM containing the cDNA sequence of the complete infectious genome of the measles virus (Schwarz strain) and an additional expression unit located between the P and M genes, this unit containing the nucleotide sequence of the domain III from the envelop protein of the Japanese encephalitis virus (JEV), strain Nakayama.

In a particular embodiment, the heterologous nucleic acid encodes a peptide that is derived from an antigen of the Yellow Fever virus selected among the envelope (Env), the NS1 proteins or immunogenic mutants thereof. When the heterologous DNA sequence present in the recombinant measles virus vector of the invention is derived from the Yellow Fever Virus (YFV), it is advantageously selected among YFV 17D 204 commercialized by Aventis Pasteur under the trademark Stamaril®.

In another particular embodiment, the heterologous nucleic acid encodes a peptide that is derived from an antigen of the West Nile virus selected among the envelope (E), premembrane (preM) or immunogenic mutants thereof. When the heterologous DNA sequence present in the recombinant measles virus vector of the invention is derived from the West Nile Virus (WNV), it is advantageously selected among the neurovirulent strain IS 98-ST1.

The heterogeneous nucleic acid may encode a tumour-specific antigen (TSA) or a tumour-associated antigen (TAA).

Another advantage of the invention is the possibility to insert in the cDNA clone of a non-segmented negative-strand RNA virus, long heterologous nucleic acid or a large number of heterologous nucleic acids. Therefore, the cDNA clone may be modified by insertion of one or several heterologous nucleic acids whose total sequence is at least 5 kb.

The invention relates to each and any nucleotide fragment contained in the polynucleotides inserted in the deposited plasmids referred to herein, and especially to each and any region suitable to design the insert, according to the present disclosure. It relates also to the use of these fragments for the construction of plasmids of the invention.

The invention also relates to methods to produce recombinant cells stably expressing the three or at least the three following proteins, a RNA polymerase, a nucleoprotein (N) of a non-segmented negative-strand RNA virus and a phosphoprotein (P) of a non-segmented negative-strand RNA virus, or functional derivatives thereof, comprising or consisting in either:

a. recombining a cell with at least:
   an expression vector comprising a DNA flap, and at least one copy of a nucleic acid encoding a RNA polymerase,
   an expression vector comprising a DNA flap, and at least one copy of a nucleic acid encoding a N protein of a non-segmented negative-strand RNA virus, and
   an expression vector comprising a DNA flap, and at least one copy of a nucleic acid encoding a P protein of a non-segmented negative-strand RNA virus, and
b. selecting the cells that stably produce at least a RNA polymerase, a nucleoprotein (N) of a non-segmented negative-strand RNA virus and a phosphoprotein (P) of a non-segmented negative-strand RNA virus, or functional derivatives thereof.

or a. recombining a cell with at least an expression vector comprising:
   at least one copy of a nucleic acid encoding a RNA polymerase under the control of a promoter,
   at least one copy of a nucleic acid encoding a N protein of a non-segmented negative-strand RNA virus under the control of a promoter,
   at least one copy of a nucleic acid encoding a P protein of a non-segmented negative-strand RNA virus under the control of a promoter, and
   a DNA flap, and
b. selecting the cells that stably produce at least a RNA polymerase, a nucleoprotein (N) of a non-segmented negative-strand RNA virus and a phosphoprotein (P) of a non-segmented negative-strand RNA virus, or functional derivatives thereof.

In a particular embodiment of the invention, the method to produce recombinant cells comprises further recombining the recombinant cells obtained in the a. step of the method above with an expression vector comprising a nucleic acid encoding a RNA polymerase large protein (L) or a functional derivative thereof of a non-segmented negative-strand RNA virus and selecting the cells that stably produce at least a RNA polymerase, a nucleoprotein (N) of a non-segmented negative-strand RNA virus and a phosphoprotein (P) of a non-segmented negative-strand RNA virus, and that produce a large protein (L) of a non-segmented negative-strand RNA virus or functional derivatives thereof.

The present invention is also directed to the use of recombinant cells of the invention, as described in the present specification, as helper cells, especially as helper cells in the production of infectious, recombinant, non-segmented negative-strand RNA virus.

Further embodiments and characteristics of the invention defined are found in the following examples and figures.

EXAMPLES

The invention will be further described in the following examples, which do not limit the scope of the invention described in the claims.

Cells and Viruses

Vero (African green monkey kidney) cells were grown as monolayers in Dulbecco's modified Eagle's medium (DMEM) supplemented with 5% fetal calf serum (FCS). Human kidney 293 (HEK-293) cells were grown in DMEM supplemented with 10% FCS. Human diploid MRC5 cells were grown as monolayers in DMEM supplemented with 10% FCS. Chicken embryo fibroblastic cells (CEF) were prepared as follows: fertilized chicken eggs (Morizeau, Dangers, France) were incubated at 38° C. for 9 days. Embryos were collected under sterile conditions. Head, limbs and viscera were removed and embryos were chopped then trypsinized for 5-10 minutes at 37° C. (Trypsin/EDTA 2.5 g/L). After filtration (70 μm) and several washes in DMEM high glucose/10% FCS, cells were seeded (5-7 10$^6$ cells per Petri dish) and incubated overnight at 37° C. before use for virus infection.

Plasmid Constructions

To allow the easy recombination of additional sequences using the Gateway® recombination system (Invitrogen), the Gateway® cassette (attb1/attb2 Seq) was introduced by ligation into the HIV-1-TRIP-ΔU3-BSX plasmid vector (Zennou et al., 2000) linearized by SmaI digestion. The T7 RNA polymerase gene was amplified from pAR-1173 plasmid (Brookhaven National Laboratory, ref) by PCR using Pfu-Turbo DNA polymerase (Stratagene) and the following primers containing the Gateway® recombination sequences (underlined):

```
AttB1-T7Pol:
5'-GGGGACAAGTTTGTACAAAAAAGCAGGCTCCACCATGGAATTCTCTG

ACATCGAACTGGCT-3'

AttB2-retourT7Pol;
5'-GGGGACCACTTTGTACAAGAAAGCTGGGTTATCACGCGAACGCGAAG

TCCGACTCTAAGATGTC-3'
```

A nuclear form of 17 RNA polymerase (nlsT7) was also amplified from pAR-3288 plasmid (Brookhaven National Laboratory, ref) using the following primers containing a nuclear localization signal (in bold) and the Gateway® recombination sequences (underlined):

```
AttB1-SV40nls:
5'-GGGGACAAGTTTGTACAAAAAAGCAGGCTCCACCATGGCACCAAAAA

AGAAGAGAAAGGTA-3'

AttB2-retourT7Pol:
5'-GGGGACCACTTTGTACAAGAAAGCTGGGTTATCACGCGAACGCGAAG

TCCGACTCTAAGATGTC-3'
```

Using the same approach, the Schwarz MV N and P genes were amplified by PCR from pTM-MVSchw plasmid, which contains a full-length infectious Schwarz MV antigenome (Combredet et al., 2003). The following primers containing the Gateway® recombination sequences (underlined) were used:

```
AttB1-N:
5'-GGGGACAAGTTTGTACAAAAAAGCAGGCTCCATGGCCACACTTTTAA

GGAGCTTAGCA-3'

AttB2-N:
5'-GGGGACCACTTTGTACAAGAAAGCTGGGTGTGTACTAGTCTAGAAGAT

TTCTGTCATTGTA-3'

AttB1-P:
5'-GGGGACAAGTTTGTACAAAAAAGCAGGCTCCATGGCAGAAGAGCAGG

CACGCCAT-3'

AttB2-P:
5'-GGGGACCACTTTGTACAAGAAAGCTGGGTGTTACTACTTCATTATTA

TCTTCATCAGCATCTGGTGGA-3'
```

The different PCR fragments encoding the T7 RNA polymerase, the nlsT7 RNA polymerase and the MV N and P proteins were then introduced into the pDONR™207 entry plasmid (Invitrogen) and recombined in the modified HIV-1-TRIP-ΔU3-BSX plasmid using the Gateway® recombination system (Invitrogen). The different recombinant vector plasmids obtained (HIV-1-TRIP delta U3.CMV-T7, HIV-1-TRIP delta U3.CMV-nlsT7, HIV-1-TRIP delta U3.CMV-N and HIV-1-TRIP delta U3.CMV-P) were fully sequenced. These vectors were deposited with the CNCM on Dec. 14, 2006, under respectively number I-3702, I-3703, I-3700 and I-3701.

The plasmid pEMC-LSchw expressing the large polymerase (L) protein from Schwarz MV was constructed in a similar way as described in Radecke et al. (1995). The 6552 nucleotide long sequence of the Schwarz L gene was taken from pTM-MVSchw plasmid (Combredet et al., 2003) and inserted into the pEMC-La plasmid previously described in Radecke et al. (1995), using classical cloning procedures. This plasmid was deposited with the CNCM on Dec. 18, 2007 under number I-3881.

Production of Vector Particles

Vector particles have been produced by co-transfection of HEK-293 cells using calcium-phosphate procedure with either HIV-1-TRIP delta U3.CMV-T7, HIV-1-TRIP delta U3.CMV-nlsT7, HIV-1-TRIP delta U3.CMV-N, or HIV-1-TRIP delta U3.CMV-P vector plasmids, an encapsidation plasmid expressing HIV-1 gag and pol genes, and a plasmid expressing the VSV-G envelope glycoprotein (pHCMV-G) as described in (Zennou et al., 2000). The amount of Gag p24 antigen in stocks of vector particles concentrated by ultracentrifugation was determined using HIV-1 p24 ELISA (Perkin Elmer LifeSciences).

Generation of Cell Lines 293-T7-MV

Cells (HEK-293) were seeded into 35 mm wells one day before transduction by TRIP-T7 and TRIP-nlsT7 lentiviral vectors. Vectors (500 ng/ml p24) were added in DMEM supplemented with 10% FCS. During 8 days, the same amount of vector was repeatedly added every day on cells. Cells were expanded every two days. After each passage, the T7 RNA polymerase activity of the cells was determined. A 35 mm cell culture was transfected with 5 μg of pEMC-Luc using the calcium-phosphate procedure, and the luciferase activity in 1/20 of the cleared cell lysate harvested one day after transfection was measured in a luminometer. The luciferase activity increased after each additional transduction and remained maximal between the 7$^{th}$ and the 8$^{th}$ transduction. The absence of cytotoxicity of T7 RNA polymerase expression was demonstrated after each transduction by quantifying cell viability using the trypan blue-exclusion method and comparison to non-transduced cells. After 8 steps of transduction, two cell populations were generated with a very high T7 RNA polymerase activity, either cytoplasmic (293-17) or nuclear (293-nlsT7).

Figure 2:
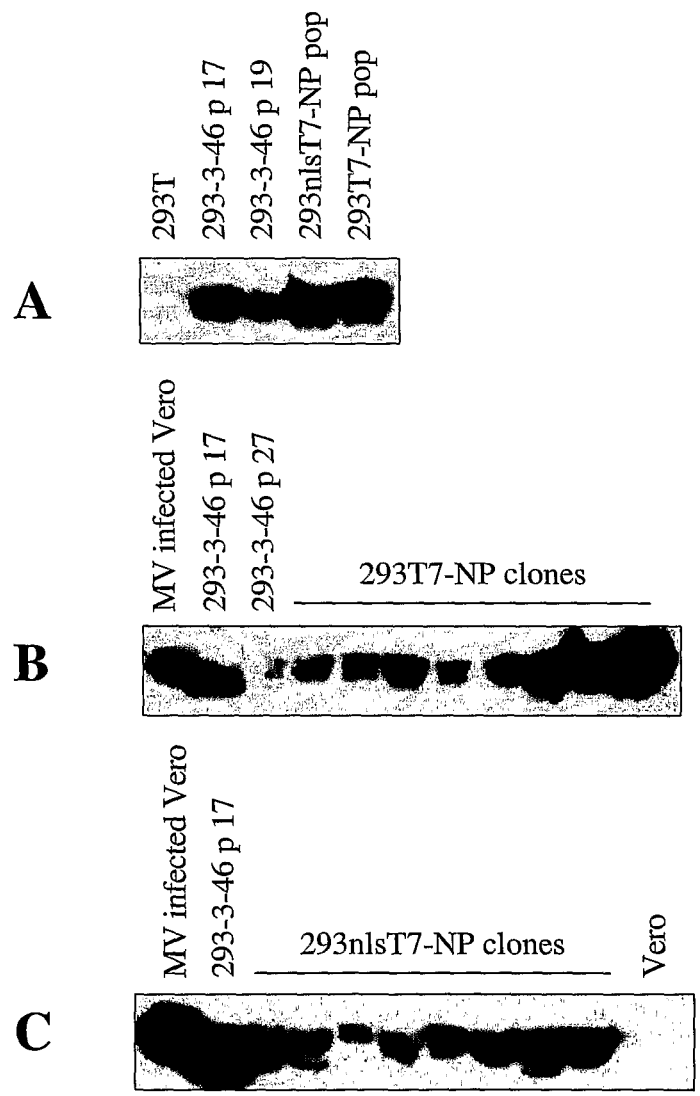
FIG. 2: Western blot showing the expression of the MV N and P proteins in different cell lysates; (A) non transduced 293T, previously described 293-3-46 cell line at two different passages (17 and 19), 293nlsT7-NP and 293T7-NP cell populations generated after transduction with lentiviral vectors; (B) MV-infected Vero cells, 293-3-46 cell line at two different passages (17 and 27), eight 293T7-NP cell clones; (C) MV-infected Vero cells, 293-3-46 cell line (passage 17), eight 293nlsT7-NP cell clones, uninfected Vero cells. Blots were probed with anti-MV NP antibody (1/500) and HRP anti-mouse Ig secondary antibody (1/1000).

The two cell populations (293-T7 and 293-nlsT7) were then co transduced simultaneously by TRIP-N and TRIP-P vectors. Vectors (TRIP N: 390 ng/ml p24 and TRIP P: 330 ng/ml p24) were added on cells seeded in 35 mm wells. During 10 days, the same amount of both vectors was repeatedly added every day on cells. Cells were expanded every two days, After 10 rounds of transduction, the expression of MV N and P proteins was analyzed on the total cell populations by western blotting using 1/20 of the total lyzate of a 35 mm well. The expression of both proteins was comparable to that of similar number of infected Vero cells (FIG. 2). Transduced cells were then cloned by limiting dilution. Cells were seeded in 96-well plates at a dilution of 1/3 cell per well. After 2 weeks, the first clones were selected. About 100 clones of each 293-T7-NP and 293-nlsT7-NP cells were expanded to 24-well plates, then to 35 mm wells. The expression of MV N and P proteins was analyzed on 20 clones by western blotting using 1/20 of the total lyzate of a 35 mm well. The expression of both proteins was comparable to that of similar number of infected Vero cells (FIG. 2). The T7 RNA polymerase activity was measured for each clone as described above, A number of clones with a very high luciferase activity and a similar level of MV N and P expression were selected. The clones, listed below, were amplified and frozen at −180° C. in DMEM/30% FCS/10% DMSO at a density of 10$^7$ cells/ml: 293-T7-NP1, 293-T7-NP3, 293-17-NP5, 293-T7-NP7, 293-T7-NP8, 293-T7-NP10, 293-T7-NP13, 293-T7-NP14, 293-T7-NP20, 293-T7-NP28, 293-T7-NP31, 293-T7-NP33, 293-nlsT7-NP1, 293-nlsT7-NP5, 293-nlsT7-NP6, 293-nlsT7-NP13, 293-nlsT7-NP14, 293-nlsT7-NP15, 293-nlsT7-NP30 and 293-nlsT7-NP40.

Rescue of Schwarz MV Using 293-T7-NP and 293-nlsT7-NP Helper Cells

To evaluate the capacity of the different helper 293-T7-NP and 293-nlsT7-NP cell clones generated to efficiently rescue MV from cDNA, we used the plasmid pTM-MVSchw-eGFP (Combredet et al., 2003) to rescue a recombinant Schwarz MV expressing the green fluorescent protein (eGFP). We used a similar system as described previously (Radecke et al., 1995; Parks et al., 1999; Combredet et al., 2003). Helper cells 293-T7-NP or 293-nlsT7-NP were transfected using the calcium phosphate procedure with pTM-MVSchw-eGFP (5 µg) and the plasmid pEMC-LSchw expressing the Schwarz MV polymerase (L) gene (20-100 ng). After overnight incubation at 37° C., the transfection medium was replaced by fresh medium and the cells were heat-shocked at 43° C. for 3 hours, then returned to 37° C. (22). After two days of incubation at 37° C., transfected cells were transferred onto monolayers of Vero, CEF or MRC5 cells and incubated at 37° C. in 10 cm dishes, except for CEF which were incubated at 32° C. Fluorescent cells appeared rapidly after 2-3 days of co culture on Vero, CEF or MRC5 cells. Infected cells expanded rapidly in focuses. The recombinant virus was highly syncytial in Vero cells and non-syncytial on CEF and MRC5 cells. Single syncytia or infectious focuses were transferred to 35 mm wells of Vero, CEF or MRC5 cells, then expanded to larger dishes by adding fresh cells. Virus was harvested from CEF or MRC5 cells after 5 days of infection, and from Vero cells when syncytia involved 80-90% of the culture (usually after 2 days) by scraping infected cells, freeze-thawing of cells and medium, and centrifugation to remove cellular debris. Such viral productions were titrated using the $TCID_{50}$ titration method. Briefly, Vero cells were seeded into 96-well plate (7500 cells/well) and infected by serial 1:10 dilutions of virus sample in DMEM/5% FCS. After incubation at 37° C. for 7 days, cells were stained with crystal violet and the virus dilution that resulted in infection in 50% of test unit was determined. The 50% end point described as tissue culture infectious dose ($TCID_{50}$) was calculated by the Kärber method (3). Recombinant virus rescued and grown on Vero cells had titers of $10^7$-$10^8$ $TCID_{50}$/ml, and virus rescued and grown on CEF or MRC5 cells had lower titers of $10^4$-$10^6$ $TCID_{50}$/ml.

The invention provides the technology for the construction and production of recombinant vectors, especially Human Immunodeficiency Virus (HIV)-TRIP lentiviral vectors, expressing the T7 RNA polymerase and measles Schwarz N and P proteins under the control of the cytomegalovirus (CMV) promoter. These vectors can be used to efficiently transduce in vitro at high level almost all cells, particularly human or mammalian cells. Such cells can be used as helper/transcomplementary cells able to generate de novo recombinant measles viruses after transfection by full-length infectious viral antigenomic cDNA or by modified cDNA clones as defined above.

The present invention allows rescuing any non-segmented negative-strand RNA viruses, such as measles viruses, from cDNA, optionally modified, without contamination by any other helper virus such as vaccinia virus, Due to the high transduction efficiency of lentiviral vectors, this method allows to generate cells expressing a very high level of helper proteins. Because retrovirus-based recombination, particularly lentiviral-based recombination, of foreign DNA into chromosomic DNA is genuine as compared to the illicit plasmid-based recombination, the helper cells generated by this method are very stable and their high efficiency to rescue non-segmented negative-strand RNA viruses from cDNA is maintained after multiple serial passages.

BIBLIOGRAPHY

Ameborn, P., G. Biberfeld, M. Forsgren, and L. V. von Stedingk. 1983. Specific and non-specific B cell activation in measles and varicella. Clin Exp Immunol 51:165-72.

Baron, M. D., and T. Barrett. 1997. Rescue of rinderpest virus from cloned cDNA. J Virol 71:1265-71.

Buchholz, U. J., H. Granzow, K. Schuldt, S. S. Whitehead, B. R. Murphy, and P. L. Collins. 2000. Chimeric bovine respiratory syncytial virus with glycoprotein gene substitutions from human respiratory syncytial virus (HRSV): effects on host range and evaluation as a live-attenuated HRSV vaccine. J Virol 74:1187-99.

C.D.C. 2005. Progress in reducing measles mortality—worldwide, 1999-2003. MMWR Morb Mortal Wkly Rep. 54:200-203.

Calain, P., and L. Roux. 1993. The rule of six, a basic feature for efficient replication of Sendai virus defective interfering RNA. J Virol 67:4822-30.

Clarke, D. K., M. S. Sidhu, J. E. Johnson, and S. A. Udem. 2000. Rescue of mumps virus from cDNA. J Virol 74:4831-8.

Collins, P. L., M. G. Hill, E. Camargo, H. Grosfeld, R. M. Chanock, and B. R. Murphy. 1995. Production of infectious human respiratory syncytial virus from cloned cDNA confirms an essential role for the transcription elongation factor from the 5' proximal open reading frame of the M2 mRNA in gene expression and provides a capability for vaccine development. Proc Natl Acad Sci USA 92:11563-7.

Combredet, C., V. Labrousse-Najburg, L. Mollet, C. Lorin, F. Delebecque, B. Hurtrel, H. McClure, M. Feinberg, M. Brahic, and F. Tangy. 2003. A molecularly cloned Schwarz strain of measles virus vaccine induces strong immune responses in macaques and transgenic mice. Journal of Virology 77:11546-11554.

Das, S. C., M. D. Baron, and T. Barrett. 2000. Recovery and characterization of a chimeric rinderpest virus with the glycoproteins of peste-des-petits-ruminants virus: homologous F and H proteins are required for virus viability. J Virol 74:9039-47.

Durbin, A. P., S. L. Hall, J. W. Siew, S. S. Whitehead, P. L. Collins, and B. R. Murphy. 1997. Recovery of infectious human parainfluenza virus type 3 from cDNA. Virology 235:323-32.

Enders, J. F., and T. C. Peebles. 1954. Propagation in tissue cultures od cytopathogenic agents from patients with measles. Proc. Soc. Exp. Biol. Med. 86:277-286.

Finke, S., and K. K. Conzelmann. 1999. Virus promoters determine interference by defective RNAs: selective amplification of mini-RNA vectors and rescue from cDNA by a 3' copy-back ambisense rabies virus. J Virol 73:3818-25.

Fujii, Y., T. Sakaguchi, K. Kiyotani, C. Huang, N. Fukuhara, Y. Egi, and T. Yoshida. 2002. Involvement of the leader sequence in Sendai virus pathogenesis revealed by recovery of a pathogenic field isolate from cDNA. J Virol 76:8540-7.

Garcin, D., P. Latorre, and D. Kolakofsky. 1999. Sendai virus C proteins counteract the interferon-mediated induction of an antiviral state. J Virol 73:6559-65.

Gassen, U., F. M. Collins, W. P. Duprex, and B. K. Rima. 2000. Establishment of a rescue system for canine distemper virus. J Virol 74:10737-44.

Griffin, D. 2001. Measles virus, p. 1401-1441. In D. Knipe and P. Howley (ed.), Field's Virology, 4th Edition, vol. 2. Lippincott-Raven Publishers, Philadelphia.

Harty, R. N., M. E. Brown, F. P. Hayes, N. T. Wright, and M. J. Schnell. 2001. Vaccinia virus-free recovery of vesicular stomatitis virus. J Mol Microbiol Biotechnol 3:513-7.

He, B., R. G. Paterson, C. D. Ward, and R. A. Lamb. 1997. Recovery of infectious SV5 from cloned DNA and expression of a foreign gene. Virology 237:249-60.

Hilleman, M. 2002. Current overview of the pathogenesis and prophylaxis of measles with focus on practical implications. Vaccine 20:651-665.

Hoffman, M. A., and A. K. Banerjee. 1997. An infectious clone of human parainfluenza virus type 3. J Virol 71:4272-7.

Ito, N., M. Takayama, K. Yamada, M. Sugiyama, and N. Minamoto. 2001. Rescue of rabies virus from cloned cDNA and identification of the pathogenicity-related gene: glycoprotein gene is associated with virulence for adult mice. J Virol 75:9121-8.

Kato, A., Y. Sakai, T. Shioda, T. Kondo, M. Nakanishi, and Y. Nagai. 1996. Initiation of Sendai virus multiplication from transfected cDNA or RNA with negative or positive sense. Genes Cells 1:569-79.

Kawano, M., M. Kaito, Y. Kozuka, H. Komada, N. Noda, K. Nanba, M. Tsurudome, M. Ito, M. Nishio, and Y. Ito. 2001. Recovery of infectious human parainfluenza type 2 virus from cDNA clones and properties of the defective virus without V-specific cysteine-rich domain. Virology 284:99-112.

Kim, E. A., K. S. Lee, S. L. Primack, H. K. Yoon, H. S. Byun, T. S. Kim, G. Y. Suh, O. J. Kwon, and J. Han. 2002. Viral pneumonias in adults: radiologic and pathologic findings. Radiographics 22 Spec No:S137-49.

Lawson, N. D., E. A. Stillman, M. A. Whitt, and J. K. Rose. 1995. Recombinant vesicular stomatitis viruses from DNA. Proc Natl Acad Sci USA 92:4477-81.

Leyrer, S., W. J. Neubert, and R. Sedlmeier. 1998. Rapid and efficient recovery of Sendai virus from cDNA: factors influencing recombinant virus rescue. J Virol Methods 75:47-58.

Okada, H., F. Kobune, T. A. Sato, T. Kohama, Y. Takeuchi, T. Abe, N. Takayama, T. Tsuchiya, and M. Tashiro. 2000. Extensive lymphopenia due to apoptosis of uninfected lymphocytes in acute measles patients. Arch Virol 145: 905-20.

Okada, H., T. A. Sato, A. Katayama, K. Higuchi, K. Shichijo, T. Tsuchiya, N. Takayama, Y. Takeuchi, T. Abe, N. Okabe, and M. Tashiro. 2001. Comparative analysis of host responses related to immunosuppression between measles patients and vaccine recipients with live attenuated measles vaccines. Arch Virol 146:859-74.

Ovsyannikova, I., N. Dhiman, R. Jacobson, R. Vierkant, and G. Poland. 2003. Frequency of measles virus-specific CD4+ and CD8+ T cells in subjects seronegative or highly seropositive for measles vaccine. Clinical and Diagnostic Laboratory Immunology 10:411-416.

Parks, C. L., R. A. Lerch, P. Walpita, M. S. Sidhu, and S. A. Udem. 1999. Enhanced measles virus cDNA rescue and gene expression after heat shock. J Virol 73:3560-6.

Parks, C. L., R. A. Lerch, P. Walpita, H. P. Wang, M. S. Sidhu, and S. A. Udem. 2001a. Analysis of the noncoding regions of measles virus strains in the Edmonston vaccine lineage. J Virol 75:921-33.

Parks, C. L., R. A. Lerch, P. Walpita, H. P. Wang, M. S. Sidhu, and S. A. Udem. 2001b. Comparison of predicted amino acid sequences of measles virus strains in the Edmonston vaccine lineage. J Virol 75:910-20.

Peeters, B. P., O. S. de Leeuw, G. Koch, and A. L. Gielkens. 1999. Rescue of Newcastle disease virus from cloned cDNA: evidence that cleavability of the fusion protein is a major determinant for virulence. J Virol 73:5001-9.

Radecke, F., P. Spielhofer, H. Schneider, K. Kaelin, M. Huber, C. Dotsch, G. Christiansen, and M. A. Billeter. 1995. Rescue of measles viruses from cloned DNA. Embo J 14:5773-84.

Romer-Oberdorfer, A., E. Mundt, T. Mebatsion, U. J. Buchholz, and T. C. Mettenleiter. 1999. Generation of recombinant lentogenic Newcastle disease virus from cDNA. J Gen Virol 80 (Pt 11):2987-95.

Schmidt, A. C., J. M. McAuliffe, A. Huang, S. R. Surman, J. E. Bailly, W. R. Elkins, P. L. Collins, B. R. Murphy, and M. H. Skiadopoulos. 2000. Bovine parainfluenza virus type 3 (BPIV3) fusion and hemagglutinin-neuraminidase glycoproteins make an important contribution to the restricted replication of BPIV3 in primates. J Virol 74:8922-9.

Schneider, H., P. Spielhofer, K. Kaelin, C. Dotsch, F. Radecke, G. Sutter, and M. A. Billeter. 1997. Rescue of measles virus using a replication-deficient vaccinia-T7 vector. J Virol Methods 64:57-64.

Schnell, M. J., L. Buonocore, E. Kretzschmar, E. Johnson, and J. K. Rose. 1996. Foreign glycoproteins expressed from recombinant vesicular stomatitis viruses are incorporated efficiently into virus particles. Proc Natl Acad Sci USA 93:11359-65.

Schnell, M. J., T. Mebatsion, and K. K. Conzelmann. 1994. Infectious rabies viruses from cloned cDNA. Embo J 13:4195-203.

Schwarz, A. 1962. Preliminary tests of a highly attenuated measles vaccine. Am. J. Dis. Child. 103:216-219.

Sirven, A., E. Ravet, P. Charneau, V. Zennou, L. Coulombel, D. Guetard, F. Pflumio, and A. Dubart-Kupperschmitt. 2001. Enhanced transgene expression in cord blood CD34 (+)-derived hematopoietic cells, including developing T cells and NOD/SCID mouse repopulating cells, following transduction with modified trip lentiviral vectors. Mol Ther 3:438-48.

Takeda, M., K. Takeuchi, N. Miyajima, F. Kobune, Y. Ami, N. Nagata, Y. Suzaki, Y. Nagai, and M. Tashiro. 2000. Recovery of pathogenic measles virus from cloned cDNA. J Virol 74:6643-7.

Volchkov, V. E., V. A. Volchkova, E. Muhlberger, L. V. Kolesnikova, M. Weik, O. Dolnik, and H. D. Klenk. 2001. Recovery of infectious Ebola virus from complementary DNA: RNA editing of the GP gene and viral cytotoxicity. Science 291:1965-9.

Whelan, S. P., L. A. Ball, J. N. Barr, and G. T. Wertz. 1995. Efficient recovery of infectious vesicular stomatitis virus entirely from cDNA clones. Proc Natl Acad Sci USA 92:8388-92.

Zennou, V., C. Petit, D. Guetard, U. Nerhbass, L. Montagnier, and P. Charneau. 2000. HIV-1 genome nuclear import is mediated by a central DNA flap. Cell 101:173-85.

Zennou, V., C. Serguera, C. Sarkis, P. Colin, E. Perret, J. Mallet, and P. Charneau. 2001. The HIV-1 DNA flap stimulates HIV vector-mediated cell transduction in the brain. Nat Biotechnol 19:446-50.

The invention claimed is:

1. A method to produce an infectious measles virus, comprising:
   a) providing a cell of the cell line 293-T7-NP deposited with the CNCM on Jun. 14, 2006, under number I-3618;
   b) transfecting the cell of a) with (i) a vector comprising the coding sequence for a RNA polymerase large protein (L) of a measles virus, and (ii) a vector comprising a cDNA clone of a measles virus;
   c) combining a transfected cell of b) with cells competent to sustain the replication and production of the measles virus to form a co-culture; and
   d) recovering the infectious measles virus from the co-culture.

2. The method of claim 1, wherein the measles virus is a Schwarz strain measles virus.

3. The method of claim 1, wherein the competent cells in c) are Vero (African green monkey kidney) cells, CEF (chick embryo fibroblast) cells or MRC5 cells.

4. The method according to claim 1, wherein the nucleotide sequence of the cDNA clone of the measles virus is modified by insertion, at a permissive site, of at least one heterologous nucleic acid.

5. The method according to claim 4, wherein the at least one heterologous nucleic acid encodes at least one epitope.

6. The method according to claim 5, wherein the measles virus is a Schwarz strain measles virus.

7. The method according to claim 1, wherein the cDNA clone is of an attenuated measles virus.

8. A cell of the cell line 293-T7-NP deposited with the CNCM on Jun. 14, 2006, under number I-3618.

9. A method to produce an infectious measles virus, comprising:
   a) providing a cell of the cell line 293-nlsT7-NP deposited with the CNCM on Aug. 4, 2006, under number I-3662;
   b) transfecting the cell of a) with (i) a vector comprising the coding sequence for a RNA polymerase large protein (L) of a measles virus, and (ii) a vector comprising a cDNA clone of a measles virus;
   c) combining a transfected cell of b) with cells competent to sustain the replication and production of the measles virus to form a co-culture; and
   d) recovering the infectious measles virus from the co-culture.

10. The method of claim 9, wherein the measles virus is a Schwarz strain measles virus.

11. The method of claim 9, wherein the competent cells in c) are Vero (African green monkey kidney) cells, CEF (chick embryo fibroblast) cells or MRC5 cells.

12. The method according to claim 9, wherein the nucleotide sequence of the cDNA clone of the measles virus is modified by insertion, at a permissive site, of at least one heterologous nucleic acid.

13. The method according to claim 12, wherein the at least one heterologous nucleic acid encodes at least one epitope.

14. The method according to claim 13, wherein the measles virus is a Schwarz strain measles virus.

15. The method according to claim 9, wherein the cDNA clone is of an attenuated measles virus.

16. A cell of the cell line 293-nlsT7-NP deposited with the CNCM on Aug. 4, 2006, under number I-3662.

* * * * *

SEQUENCE LISTING

```
<160> NUMBER OF SEQ ID NOS: 26

<210> SEQ ID NO 1
<211> LENGTH: 200
<212> TYPE: DNA
<213> ORGANISM: Artificial
<220> FEATURE:
<223> OTHER INFORMATION: CAEV FLAP

<400> SEQUENCE: 1
gttccagcca caatttgtcg ctgtagaatc agccatagca gcagccctag tcgccataaa      60
tataaaaaga aagggtgggc tggggacaag ccctatggat atttttatat ataataaaga     120
acagaaaaga ataaataata aatataataa aaattctcaa aaaattcaat tctgttatta     180
cagaataagg aaaagaggac                                                 200

<210> SEQ ID NO 2
<211> LENGTH: 200
<212> TYPE: DNA
<213> ORGANISM: Artificial
<220> FEATURE:
<223> OTHER INFORMATION: EIAV FLAP

<400> SEQUENCE: 2
cttgtaacaa agggagggaa agtatgggag gacagacacc atgggaagta tttatcacta      60
atcaagcaca agtaatacat gagaaacttt tactacagca agcacaatcc tccaaaaaat     120
tttgttttta caaatccct ggtgaacatg attggaaggg acctactagg gtgctgtgga     180
agggtgatgg tgcagtagta                                                 200

<210> SEQ ID NO 3
<211> LENGTH: 200
<212> TYPE: DNA
<213> ORGANISM: Artificial
<220> FEATURE:
<223> OTHER INFORMATION: VISNA FLAP

<400> SEQUENCE: 3
ggaccctcat tactctaaat ataaaagaa agggtgggct agggacaagc cctatggata       60
tatttatatt taataaggaa caacaaagaa tacagcaaca aagtaaatca aaacaagaaa     120
aaattcgatt ttgttattac agaacaagaa aaagagggca tccaggagag tggcaaggac     180
```

```
caacacaggt actttggggc                                              200

<210> SEQ ID NO 4
<211> LENGTH: 200
<212> TYPE: DNA
<213> ORGANISM: Artificial
<220> FEATURE:
<223> OTHER INFORMATION: SIV AGM FLAP

<400> SEQUENCE: 4
tactgatggc ttgcatactt cacaatttta aagaaaggg aggaataggg ggacagactt     60
cagcagagag actaattaat ataataacaa cacaattaga aatacaacat ttacaaacca   120
aaattcaaaa aattttaaat tttagagtct actacagaga agggagagac cctgtgtgga   180
aaggaccggc acaattaatc                                              200

<210> SEQ ID NO 5
<211> LENGTH: 200
<212> TYPE: DNA
<213> ORGANISM: Artificial
<220> FEATURE:
<223> OTHER INFORMATION: HIV-2 ROD FLAP

<400> SEQUENCE: 5
tgcatgaatt ttaaaagaag gggggggaata ggggatatga ctccatcaga aagattaatc    60
aatatgatca ccacagaaca agagatacaa ttcctccaag ccaaaaattc aaaattaaaa   120
gattttcggg tctatttcag agaaggcaga gatcagttgt ggaaaggacc tggggaacta   180
ctgtggaaag gagaaggagc                                              200

<210> SEQ ID NO 6
<211> LENGTH: 200
<212> TYPE: DNA
<213> ORGANISM: Artificial
<220> FEATURE:
<223> OTHER INFORMATION: HIV-1 LAI FLAP

<400> SEQUENCE: 6
cagtattcat ccacaatttt aaaagaaaag gggggattgg ggggtacagt gcagggaaa     60 gaatagtaga cataatagca acagacatac aaactaaaga attacaaaaa caaattacaa   120
aaattcaaaa ttttcgggtt tattacaggg acagcagaga tccactttgg aaaggaccag   180
caaagctcct ctggaaaggt                                              200

<210> SEQ ID NO 7
<211> LENGTH: 119
<212> TYPE: DNA
<213> ORGANISM: Artificial
<220> FEATURE:
<223> OTHER INFORMATION: HIV-1 FLAP

<400> SEQUENCE: 7
ttttaaaaga aaaggggggga ttgggggggta cagtgcaggg gaaagaatag tagacataat    60
agcaacagac atacaaacta agaattaca aaacaaatt acaaaaattc aaaattttc      119

<210> SEQ ID NO 8
<211> LENGTH: 2640
<212> TYPE: DNA
<213> ORGANISM: Bacteriophage T7
<220> FEATURE:
<221> NAME/KEY: misc_feature
<222> LOCATION: (1)..(2640)
<223> OTHER INFORMATION: T7 RNA polymerase gene
<220> FEATURE:
```

<221> NAME/KEY: CDS
<222> LOCATION: (10)..(2637)

<400> SEQUENCE: 8

```
ggctccacc atg gaa ttc tct gac atc gaa ctg gct gct atc ccg ttc aac      51
          Met Glu Phe Ser Asp Ile Glu Leu Ala Ala Ile Pro Phe Asn
          1               5                   10 act ctg gct gac cat tac ggt gag cgt tta gct cgc gaa cag ttg gcc        99
Thr Leu Ala Asp His Tyr Gly Glu Arg Leu Ala Arg Glu Gln Leu Ala
15                  20                  25                  30 ctt gag cat gag tct tac gag atg ggt gaa gca cgc ttc cgc aag atg       147
Leu Glu His Glu Ser Tyr Glu Met Gly Glu Ala Arg Phe Arg Lys Met
                35                  40                  45 ttt gag cgt caa ctt aaa gct ggt gag gtt gcg gat aac gct gcc gcc       195
Phe Glu Arg Gln Leu Lys Ala Gly Glu Val Ala Asp Asn Ala Ala Ala
            50                  55                  60 aag cct ctc atc act acc cta ctc cct aag atg att gca cgc atc aac       243
Lys Pro Leu Ile Thr Thr Leu Leu Pro Lys Met Ile Ala Arg Ile Asn
65                  70                  75 gac tgg ttt gag gaa gtg aaa gct aag cgc ggc aag cgc ccg aca gcc       291
Asp Trp Phe Glu Glu Val Lys Ala Lys Arg Gly Lys Arg Pro Thr Ala
80                  85                  90 ttc cag ttc ctg caa gaa atc aag ccg gaa gcc gta gcg tac atc acc       339
Phe Gln Phe Leu Gln Glu Ile Lys Pro Glu Ala Val Ala Tyr Ile Thr
95                  100                 105                 110 att aag acc act ctg gct tgc cta acc agt gct gac aat aca acc gtt       387
Ile Lys Thr Thr Leu Ala Cys Leu Thr Ser Ala Asp Asn Thr Thr Val
                115                 120                 125 cag gct gta gca agc gca atc ggt cgg gcc att gag gac gag gct cgc       435
Gln Ala Val Ala Ser Ala Ile Gly Arg Ala Ile Glu Asp Glu Ala Arg
            130                 135                 140 ttc ggt cgt atc cgt gac ctt gaa gct aag cac ttc aag aaa aac gtt       483
Phe Gly Arg Ile Arg Asp Leu Glu Ala Lys His Phe Lys Lys Asn Val
        145                 150                 155 gag gaa caa ctc aac aag cgc gta ggg cac gtc tac aag aaa gca ttt       531
Glu Glu Gln Leu Asn Lys Arg Val Gly His Val Tyr Lys Lys Ala Phe
160                 165                 170 atg caa gtt gtc gag gct gac atg ctc tct aag ggt cta ctc ggt ggc       579
Met Gln Val Val Glu Ala Asp Met Leu Ser Lys Gly Leu Leu Gly Gly
175                 180                 185                 190 gag gcg tgg tct tcg tgg cat aag gaa gac tct att cat gta gga gta       627
Glu Ala Trp Ser Ser Trp His Lys Glu Asp Ser Ile His Val Gly Val
                195                 200                 205 cgc tgc atc gag atg ctc att gag tca acc gga atg gtt agc tta cac       675
Arg Cys Ile Glu Met Leu Ile Glu Ser Thr Gly Met Val Ser Leu His
            210                 215                 220 cgc caa aat gct ggc gta gta ggt caa gac tct gag act atc gaa ctc       723
Arg Gln Asn Ala Gly Val Val Gly Gln Asp Ser Glu Thr Ile Glu Leu
        225                 230                 235 gca cct gaa tac gct gag gct atc gca acc cgt gca ggt gcg ctg gct       771
Ala Pro Glu Tyr Ala Glu Ala Ile Ala Thr Arg Ala Gly Ala Leu Ala
240                 245                 250 ggc atc tct ccg atg ttc caa cct tgc gta gtt cct cct aag ccg tgg       819
Gly Ile Ser Pro Met Phe Gln Pro Cys Val Val Pro Pro Lys Pro Trp
255                 260                 265                 270 act ggc att act ggt ggt ggc tat tgg gct aac ggt cgt cgt cct ctg       867
Thr Gly Ile Thr Gly Gly Gly Tyr Trp Ala Asn Gly Arg Arg Pro Leu
                275                 280                 285 gcg ctg gtg cgt act cac agt aag aaa gca ctg atg cgc tac gaa gac       915
Ala Leu Val Arg Thr His Ser Lys Lys Ala Leu Met Arg Tyr Glu Asp
            290                 295                 300
```

| | | |
|---|---|---|
| gtt tac atg cct gag gtg tac aaa gcg att aac att gcg caa aac acc<br>Val Tyr Met Pro Glu Val Tyr Lys Ala Ile Asn Ile Ala Gln Asn Thr<br>305 310 315 | | 963 |
| gca tgg aaa atc aac aag aaa gtc cta gcg gtc gcc aac gta atc acc<br>Ala Trp Lys Ile Asn Lys Lys Val Leu Ala Val Ala Asn Val Ile Thr<br>320 325 330 | | 1011 |
| aag tgg aag cat tgt ccg gtc gag gac atc cct gcg att gag cgt gaa<br>Lys Trp Lys His Cys Pro Val Glu Asp Ile Pro Ala Ile Glu Arg Glu<br>335 340 345 350 | | 1059 |
| gaa ctc ccg atg aaa ccg gaa gac atc gac atg aat cct gag gct ctc<br>Glu Leu Pro Met Lys Pro Glu Asp Ile Asp Met Asn Pro Glu Ala Leu<br>355 360 365 | | 1107 |
| acc gcg tgg aaa cgt gct gcc gct gct gtg tac cgc aag gac agg gct<br>Thr Ala Trp Lys Arg Ala Ala Ala Ala Val Tyr Arg Lys Asp Arg Ala<br>370 375 380 | | 1155 |
| cgc aag tct cgc cgt atc agc ctt gag ttc atg ctt gag caa gcc aat<br>Arg Lys Ser Arg Arg Ile Ser Leu Glu Phe Met Leu Glu Gln Ala Asn<br>385 390 395 | | 1203 |
| aag ttt gct aac cat aag gcc atc tgg ttc cct tac aac atg gac tgg<br>Lys Phe Ala Asn His Lys Ala Ile Trp Phe Pro Tyr Asn Met Asp Trp<br>400 405 410 | | 1251 |
| cgc ggt cgt gtt tac gcc gtg tca atg ttc aac ccg caa ggt aac gat<br>Arg Gly Arg Val Tyr Ala Val Ser Met Phe Asn Pro Gln Gly Asn Asp<br>415 420 425 430 | | 1299 |
| atg acc aaa gga ctg ctt acg ctg gcg aaa ggt aaa cca atc ggt aag<br>Met Thr Lys Gly Leu Leu Thr Leu Ala Lys Gly Lys Pro Ile Gly Lys<br>435 440 445 | | 1347 |
| gaa ggt tac tac tgg ctg aaa atc cac ggt gca aac tgt gcg ggt gtc<br>Glu Gly Tyr Tyr Trp Leu Lys Ile His Gly Ala Asn Cys Ala Gly Val<br>450 455 460 | | 1395 |
| gat aag gtt ccg ttc cct gag cgc atc aag ttc att gag gaa aac cac<br>Asp Lys Val Pro Phe Pro Glu Arg Ile Lys Phe Ile Glu Glu Asn His<br>465 470 475 | | 1443 |
| gag aac atc atg gct tgc gct aag tct cca ctg gag aac act tgg tgg<br>Glu Asn Ile Met Ala Cys Ala Lys Ser Pro Leu Glu Asn Thr Trp Trp<br>480 485 490 | | 1491 |
| gct gag caa gat tct ccg ttc tgc ttc ctt gcg ttc tgc ttt gag tac<br>Ala Glu Gln Asp Ser Pro Phe Cys Phe Leu Ala Phe Cys Phe Glu Tyr<br>495 500 505 510 | | 1539 |
| gct ggg gta cag cac cac ggc ctg agc tat aac tgc tcc ctt ccg ctg<br>Ala Gly Val Gln His His Gly Leu Ser Tyr Asn Cys Ser Leu Pro Leu<br>515 520 525 | | 1587 |
| gcg ttt gac ggg tct tgc tct ggc atc cag cac ttc tcc gcg atg ctc<br>Ala Phe Asp Gly Ser Cys Ser Gly Ile Gln His Phe Ser Ala Met Leu<br>530 535 540 | | 1635 |
| cga gat gag gta ggt ggt cgc gcg gtt aac ttg ctt cct agt gag acc<br>Arg Asp Glu Val Gly Gly Arg Ala Val Asn Leu Leu Pro Ser Glu Thr<br>545 550 555 | | 1683 |
| gtt cag gac atc tac ggg att gtt gct aag aaa gtc aac gag att cta<br>Val Gln Asp Ile Tyr Gly Ile Val Ala Lys Lys Val Asn Glu Ile Leu<br>560 565 570 | | 1731 |
| caa gca gac gca atc aat ggg acc gat aac gaa gta gtt acc gtg acc<br>Gln Ala Asp Ala Ile Asn Gly Thr Asp Asn Glu Val Val Thr Val Thr<br>575 580 585 590 | | 1779 |
| gat gag aac act ggt gaa atc tct gag aaa gtc aag ctg ggc act aag<br>Asp Glu Asn Thr Gly Glu Ile Ser Glu Lys Val Lys Leu Gly Thr Lys<br>595 600 605 | | 1827 |
| gca ctg gct ggt caa tgg ctg gct cac ggt gtt act cgc agt gtg act<br>Ala Leu Ala Gly Gln Trp Leu Ala His Gly Val Thr Arg Ser Val Thr<br>610 615 620 | | 1875 |

```
aag cgt tca gtc atg acg ctg gct tac ggg tcc aaa gag ttc ggc ttc        1923
Lys Arg Ser Val Met Thr Leu Ala Tyr Gly Ser Lys Glu Phe Gly Phe
        625                 630                 635 cgt caa caa gtg ctg gaa gat acc att cag cca gct att gat tcc ggc        1971
Arg Gln Gln Val Leu Glu Asp Thr Ile Gln Pro Ala Ile Asp Ser Gly
640                 645                 650 aag ggt ccg atg ttc act cag ccg aat cag gct gct gga tac atg gct        2019
Lys Gly Pro Met Phe Thr Gln Pro Asn Gln Ala Ala Gly Tyr Met Ala
655                 660                 665                 670 aag ctg att tgg gaa tct gtg agc gtg acg gtg gta gct gcg gtt gaa        2067
Lys Leu Ile Trp Glu Ser Val Ser Val Thr Val Val Ala Ala Val Glu
        675                 680                 685 gca atg aac tgg ctt aag tct gct gct aag ctg ctg gct gct gag gtc        2115
Ala Met Asn Trp Leu Lys Ser Ala Ala Lys Leu Leu Ala Ala Glu Val
        690                 695                 700 aaa gat aag aag act gga gag att ctt cgc aag cgt tgc gct gtg cat        2163
Lys Asp Lys Lys Thr Gly Glu Ile Leu Arg Lys Arg Cys Ala Val His
        705                 710                 715 tgg gta act cct gat ggt ttc cct gtg tgg cag gaa tac aag aag cct        2211
Trp Val Thr Pro Asp Gly Phe Pro Val Trp Gln Glu Tyr Lys Lys Pro
        720                 725                 730 att cag acg cgc ttg aac ctg atg ttc ctc ggt cag ttc cgc tta cag        2259
Ile Gln Thr Arg Leu Asn Leu Met Phe Leu Gly Gln Phe Arg Leu Gln
735                 740                 745                 750 cct acc att aac acc aac aaa gat agc gag att gat gca cac aaa cag        2307
Pro Thr Ile Asn Thr Asn Lys Asp Ser Glu Ile Asp Ala His Lys Gln
        755                 760                 765 gag tct ggt atc gct cct aac ttt gta cac agc caa gac ggt agc cac        2355
Glu Ser Gly Ile Ala Pro Asn Phe Val His Ser Gln Asp Gly Ser His
        770                 775                 780 ctt cgt aag act gta gtg tgg gca cac gag aag tac gga atc gaa tct        2403
Leu Arg Lys Thr Val Val Trp Ala His Glu Lys Tyr Gly Ile Glu Ser
        785                 790                 795 ttt gca ctg att cac gac tcc ttc ggt acc att ccg gct gac gct gcg        2451
Phe Ala Leu Ile His Asp Ser Phe Gly Thr Ile Pro Ala Asp Ala Ala
800                 805                 810 aac ctg ttc aaa gca gtg cgc gaa act atg gtt gac aca tat gag tct        2499
Asn Leu Phe Lys Ala Val Arg Glu Thr Met Val Asp Thr Tyr Glu Ser
815                 820                 825                 830 tgt gat gta ctg gct gat ttc tac gac cag ttc gct gac cag ttg cac        2547
Cys Asp Val Leu Ala Asp Phe Tyr Asp Gln Phe Ala Asp Gln Leu His
        835                 840                 845 gag tct caa ttg gac aaa atg cca gca ctt ccg gct aaa ggt aac ttg        2595
Glu Ser Gln Leu Asp Lys Met Pro Ala Leu Pro Ala Lys Gly Asn Leu
        850                 855                 860 aac ctc cgt gac atc tta gag tcg gac ttc gcg ttc gcg tga taa            2640
Asn Leu Arg Asp Ile Leu Glu Ser Asp Phe Ala Phe Ala
        865                 870                 875

<210> SEQ ID NO 9
<211> LENGTH: 875
<212> TYPE: PRT
<213> ORGANISM: Bacteriophage T7

<400> SEQUENCE: 9

Met Glu Phe Ser Asp Ile Glu Leu Ala Ala Ile Pro Phe Asn Thr Leu
1               5                   10                  15

Ala Asp His Tyr Gly Glu Arg Leu Ala Arg Glu Gln Leu Ala Leu Glu
            20                  25                  30

His Glu Ser Tyr Glu Met Gly Glu Ala Arg Phe Arg Lys Met Phe Glu
```

```
                35                  40                  45
Arg Gln Leu Lys Ala Gly Glu Val Ala Asp Asn Ala Ala Lys Pro
 50                  55                  60
Leu Ile Thr Thr Leu Leu Pro Lys Met Ile Ala Arg Ile Asn Asp Trp
 65                  70                  75                  80
Phe Glu Glu Val Lys Ala Lys Arg Gly Lys Arg Pro Thr Ala Phe Gln
                     85                  90                  95
Phe Leu Gln Glu Ile Lys Pro Glu Ala Val Ala Tyr Ile Thr Ile Lys
                100                 105                 110
Thr Thr Leu Ala Cys Leu Thr Ser Ala Asp Asn Thr Thr Val Gln Ala
                115                 120                 125
Val Ala Ser Ala Ile Gly Arg Ala Ile Glu Asp Glu Ala Arg Phe Gly
            130                 135                 140
Arg Ile Arg Asp Leu Glu Ala Lys His Phe Lys Lys Asn Val Glu Glu
145                 150                 155                 160
Gln Leu Asn Lys Arg Val Gly His Val Tyr Lys Lys Ala Phe Met Gln
                165                 170                 175
Val Val Glu Ala Asp Met Leu Ser Lys Gly Leu Leu Gly Gly Glu Ala
                180                 185                 190
Trp Ser Ser Trp His Lys Glu Asp Ser Ile His Val Gly Val Arg Cys
            195                 200                 205
Ile Glu Met Leu Ile Glu Ser Thr Gly Met Val Ser Leu His Arg Gln
            210                 215                 220
Asn Ala Gly Val Val Gly Gln Asp Ser Glu Thr Ile Glu Leu Ala Pro
225                 230                 235                 240
Glu Tyr Ala Glu Ala Ile Ala Thr Arg Ala Gly Ala Leu Ala Gly Ile
                245                 250                 255
Ser Pro Met Phe Gln Pro Cys Val Val Pro Pro Lys Pro Trp Thr Gly
                260                 265                 270
Ile Thr Gly Gly Gly Tyr Trp Ala Asn Gly Arg Arg Pro Leu Ala Leu
            275                 280                 285
Val Arg Thr His Ser Lys Lys Ala Leu Met Arg Tyr Glu Asp Val Tyr
            290                 295                 300
Met Pro Glu Val Tyr Lys Ala Ile Asn Ile Ala Gln Asn Thr Ala Trp
305                 310                 315                 320
Lys Ile Asn Lys Lys Val Leu Ala Val Ala Asn Val Ile Thr Lys Trp
                325                 330                 335
Lys His Cys Pro Val Glu Asp Ile Pro Ala Ile Glu Arg Glu Glu Leu
                340                 345                 350
Pro Met Lys Pro Glu Asp Ile Asp Met Asn Pro Glu Ala Leu Thr Ala
                355                 360                 365
Trp Lys Arg Ala Ala Ala Val Tyr Arg Lys Asp Arg Ala Arg Lys
            370                 375                 380
Ser Arg Arg Ile Ser Leu Glu Phe Met Leu Glu Gln Ala Asn Lys Phe
385                 390                 395                 400
Ala Asn His Lys Ala Ile Trp Phe Pro Tyr Asn Met Asp Trp Arg Gly
                405                 410                 415
Arg Val Tyr Ala Val Ser Met Phe Asn Pro Gln Gly Asn Asp Met Thr
                420                 425                 430
Lys Gly Leu Leu Thr Leu Ala Lys Gly Lys Pro Ile Gly Lys Glu Gly
            435                 440                 445
Tyr Tyr Trp Leu Lys Ile His Gly Ala Asn Cys Ala Gly Val Asp Lys
450                 455                 460
```

```
Val Pro Phe Pro Glu Arg Ile Lys Phe Ile Glu Glu Asn His Glu Asn
465                 470                 475                 480

Ile Met Ala Cys Ala Lys Ser Pro Leu Glu Asn Thr Trp Trp Ala Glu
                485                 490                 495

Gln Asp Ser Pro Phe Cys Phe Leu Ala Phe Cys Phe Glu Tyr Ala Gly
            500                 505                 510

Val Gln His His Gly Leu Ser Tyr Asn Cys Ser Leu Pro Leu Ala Phe
        515                 520                 525

Asp Gly Ser Cys Ser Gly Ile Gln His Phe Ser Ala Met Leu Arg Asp
    530                 535                 540

Glu Val Gly Gly Arg Ala Val Asn Leu Leu Pro Ser Gly Thr Val Gln
545                 550                 555                 560

Asp Ile Tyr Gly Ile Val Ala Lys Lys Val Asn Glu Ile Leu Gln Ala
                565                 570                 575

Asp Ala Ile Asn Gly Thr Asp Asn Glu Val Val Thr Val Thr Asp Glu
            580                 585                 590

Asn Thr Gly Glu Ile Ser Glu Lys Val Lys Leu Gly Thr Lys Ala Leu
        595                 600                 605

Ala Gly Gln Trp Leu Ala His Gly Val Thr Arg Ser Val Thr Lys Arg
610                 615                 620

Ser Val Met Thr Leu Ala Tyr Gly Ser Lys Glu Phe Gly Phe Arg Gln
625                 630                 635                 640

Gln Val Leu Glu Asp Thr Ile Gln Pro Ala Ile Asp Ser Gly Lys Gly
                645                 650                 655

Pro Met Phe Thr Gln Pro Asn Gln Ala Ala Gly Tyr Met Ala Lys Leu
            660                 665                 670

Ile Trp Glu Ser Val Ser Val Thr Val Ala Ala Val Glu Ala Met
        675                 680                 685

Asn Trp Leu Lys Ser Ala Ala Lys Leu Leu Ala Ala Glu Val Lys Asp
    690                 695                 700

Lys Lys Thr Gly Glu Ile Leu Arg Lys Arg Cys Ala Val His Trp Val
705                 710                 715                 720

Thr Pro Asp Gly Phe Pro Val Trp Gln Glu Tyr Lys Lys Pro Ile Gln
                725                 730                 735

Thr Arg Leu Asn Leu Met Phe Leu Gly Gln Phe Arg Leu Gln Pro Thr
            740                 745                 750

Ile Asn Thr Asn Lys Asp Ser Glu Ile Asp Ala His Lys Gln Glu Ser
        755                 760                 765

Gly Ile Ala Pro Asn Phe Val His Ser Gln Asp Gly Ser His Leu Arg
770                 775                 780

Lys Thr Val Val Trp Ala His Glu Lys Tyr Gly Ile Glu Ser Phe Ala
785                 790                 795                 800

Leu Ile His Asp Ser Phe Gly Thr Ile Pro Ala Asp Ala Ala Asn Leu
                805                 810                 815

Phe Lys Ala Val Arg Glu Thr Met Val Asp Thr Tyr Glu Ser Cys Asp
            820                 825                 830

Val Leu Ala Asp Phe Tyr Asp Gln Phe Ala Asp Gln Leu His Glu Ser
        835                 840                 845

Gln Leu Asp Lys Met Pro Ala Leu Pro Ala Lys Gly Asn Leu Asn Leu
850                 855                 860

Arg Asp Ile Leu Glu Ser Asp Phe Ala Phe Ala
865                 870                 875

<210> SEQ ID NO 10
```

```
<211> LENGTH: 2676
<212> TYPE: DNA
<213> ORGANISM: Bacteriophage T7
<220> FEATURE:
<221> NAME/KEY: misc_feature
<222> LOCATION: (1)..(2676)
<223> OTHER INFORMATION: nls T7 RNA polymerase gene
<220> FEATURE:
<221> NAME/KEY: CDS
<222> LOCATION: (10)..(2673)

<400> SEQUENCE: 10 ggctccacc atg gca cca aaa aag aag aga aag gta gaa gac ccc aag gaa        51
          Met Ala Pro Lys Lys Lys Arg Lys Val Glu Asp Pro Lys Glu
          1               5                   10 ttc tct gac atc gaa ctg gct gct atc ccg ttc aac act ctg gct gac          99
Phe Ser Asp Ile Glu Leu Ala Ala Ile Pro Phe Asn Thr Leu Ala Asp
15                  20                  25                  30 cat tac ggt gag cgt tta gct cgc gaa cag ttg gcc ctt gag cat gag         147
His Tyr Gly Glu Arg Leu Ala Arg Glu Gln Leu Ala Leu Glu His Glu
                35                  40                  45 tct tac gag atg ggt gaa gca cgc ttc cgc aag atg ttt gag cgt caa         195
Ser Tyr Glu Met Gly Glu Ala Arg Phe Arg Lys Met Phe Glu Arg Gln
        50                  55                  60 ctt aaa gct ggt gag gtt gcg gat aac gct gcc gcc aag cct ctc atc         243
Leu Lys Ala Gly Glu Val Ala Asp Asn Ala Ala Ala Lys Pro Leu Ile
    65                  70                  75 act acc cta ctc cct aag atg att gca cgc atc aac gac tgg ttt gag         291
Thr Thr Leu Leu Pro Lys Met Ile Ala Arg Ile Asn Asp Trp Phe Glu
80                  85                  90 gaa gtg aaa gct aag cgc ggc aag cgc ccg aca gcc ttc cag ttc ctg         339
Glu Val Lys Ala Lys Arg Gly Lys Arg Pro Thr Ala Phe Gln Phe Leu
95                  100                 105                 110 caa gaa atc aag ccg gaa gcc gta gcg tac atc acc att aag acc act         387
Gln Glu Ile Lys Pro Glu Ala Val Ala Tyr Ile Thr Ile Lys Thr Thr
                115                 120                 125 ctg gct tgc cta acc agt gct gac aat aca acc gtt cag gct gta gca         435
Leu Ala Cys Leu Thr Ser Ala Asp Asn Thr Thr Val Gln Ala Val Ala
        130                 135                 140 agc gca atc ggt cgg gcc att gag gac gag gct cgc ttc ggt cgt atc         483
Ser Ala Ile Gly Arg Ala Ile Glu Asp Glu Ala Arg Phe Gly Arg Ile
    145                 150                 155 cgt gac ctt gaa gct aag cac ttc aag aaa aac gtt gag gaa caa ctc         531
Arg Asp Leu Glu Ala Lys His Phe Lys Lys Asn Val Glu Glu Gln Leu
160                 165                 170 aac aag cgc gta ggg cac gtc tac aag aaa gca ttt atg caa gtt gtc         579
Asn Lys Arg Val Gly His Val Tyr Lys Lys Ala Phe Met Gln Val Val
175                 180                 185                 190 gag gct gac atg ctc tct aag ggt cta ctc ggt ggc gag gcg tgg tct         627
Glu Ala Asp Met Leu Ser Lys Gly Leu Leu Gly Gly Glu Ala Trp Ser
                195                 200                 205 tcg tgg cat aag gaa gac tct att cat gta gga gta cgc tgc atc gag         675
Ser Trp His Lys Glu Asp Ser Ile His Val Gly Val Arg Cys Ile Glu
        210                 215                 220 atg ctc att gag tca acc gga atg gtt agc tta cac cgc caa aat gct         723
Met Leu Ile Glu Ser Thr Gly Met Val Ser Leu His Arg Gln Asn Ala
    225                 230                 235 ggc gta gta ggt caa gac tct gag act atc gaa ctc gca cct gaa tac         771
Gly Val Val Gly Gln Asp Ser Glu Thr Ile Glu Leu Ala Pro Glu Tyr
240                 245                 250 gct gag gct atc gca acc cgt gca ggt gcg ctg gct ggc atc tct ccg         819
Ala Glu Ala Ile Ala Thr Arg Ala Gly Ala Leu Ala Gly Ile Ser Pro
255                 260                 265                 270
```

```
atg ttc caa cct tgc gta gtt cct cct aag ccg tgg act ggc att act       867
Met Phe Gln Pro Cys Val Val Pro Pro Lys Pro Trp Thr Gly Ile Thr
            275                 280                 285 ggt ggt ggc tat tgg gct aac ggt cgt cgt cct ctg gcg ctg gtg cgt       915
Gly Gly Gly Tyr Trp Ala Asn Gly Arg Arg Pro Leu Ala Leu Val Arg
            290                 295                 300 act cac agt aag aaa gca ctg atg cgc tac gaa gac gtt tac atg cct       963
Thr His Ser Lys Lys Ala Leu Met Arg Tyr Glu Asp Val Tyr Met Pro
            305                 310                 315 gag gtg tac aaa gcg att aac att gcg caa aac acc gca tgg aaa atc      1011
Glu Val Tyr Lys Ala Ile Asn Ile Ala Gln Asn Thr Ala Trp Lys Ile
            320                 325                 330 aac aag aaa gtc cta gcg gtc gcc aac gta atc acc aag tgg aag cat      1059
Asn Lys Lys Val Leu Ala Val Ala Asn Val Ile Thr Lys Trp Lys His
335                 340                 345                 350 tgt ccg gtc gag gac atc cct gcg att gag cgt gaa gaa ctc ccg atg      1107
Cys Pro Val Glu Asp Ile Pro Ala Ile Glu Arg Glu Glu Leu Pro Met
                355                 360                 365 aaa ccg gaa gac atc gac atg aat cct gag gct ctc acc gcg tgg aaa      1155
Lys Pro Glu Asp Ile Asp Met Asn Pro Glu Ala Leu Thr Ala Trp Lys
            370                 375                 380 cgt gct gcc gct gct gtg tac cgc aag gac agg gct cgc aag tct cgc      1203
Arg Ala Ala Ala Ala Val Tyr Arg Lys Asp Arg Ala Arg Lys Ser Arg
            385                 390                 395 cgt atc agc ctt gag ttc atg ctt gag caa gcc aat aag ttt gct aac      1251
Arg Ile Ser Leu Glu Phe Met Leu Glu Gln Ala Asn Lys Phe Ala Asn
            400                 405                 410 cat aag gcc atc tgg ttc cct tac aac atg gac tgg cgc ggt cgt gtt      1299
His Lys Ala Ile Trp Phe Pro Tyr Asn Met Asp Trp Arg Gly Arg Val
415                 420                 425                 430 tac gcc gtg tca atg ttc aac ccg caa ggt aac gat atg acc aaa gga      1347
Tyr Ala Val Ser Met Phe Asn Pro Gln Gly Asn Asp Met Thr Lys Gly
                435                 440                 445 ctg ctt acg ctg gcg aaa ggt aaa cca atc ggt aag gaa ggt tac tac      1395
Leu Leu Thr Leu Ala Lys Gly Lys Pro Ile Gly Lys Glu Gly Tyr Tyr
            450                 455                 460 tgg ctg aaa atc cac ggt gca aac tgt gcg ggt gtc gat aag gtt ccg      1443
Trp Leu Lys Ile His Gly Ala Asn Cys Ala Gly Val Asp Lys Val Pro
            465                 470                 475 ttc cct gag cgc atc aag ttc att gag gaa aac cac gag aac atc atg      1491
Phe Pro Glu Arg Ile Lys Phe Ile Glu Glu Asn His Glu Asn Ile Met
            480                 485                 490 gct tgc gct aag tct cca ctg gag aac act tgg tgg gct gag caa gat      1539
Ala Cys Ala Lys Ser Pro Leu Glu Asn Thr Trp Trp Ala Glu Gln Asp
495                 500                 505                 510 tct ccg ttc tgc ttc ctt gcg ttc tgc ttt gag tac gct ggg gta cag      1587
Ser Pro Phe Cys Phe Leu Ala Phe Cys Phe Glu Tyr Ala Gly Val Gln
                515                 520                 525 cac cac ggc ctg agc tat aac tgc tcc ctt ccg ctg gcg ttt gac ggg      1635
His His Gly Leu Ser Tyr Asn Cys Ser Leu Pro Leu Ala Phe Asp Gly
            530                 535                 540 tct tgc tct ggc atc cag cac ttc tcc gcg atg ctc cga gat gag gta      1683
Ser Cys Ser Gly Ile Gln His Phe Ser Ala Met Leu Arg Asp Glu Val
            545                 550                 555 ggt ggt cgc gcg gtt aac ttg ctt cct agt gag acc gtt cag gac atc      1731
Gly Gly Arg Ala Val Asn Leu Leu Pro Ser Glu Thr Val Gln Asp Ile
            560                 565                 570 tac ggg att gtt gct aag aaa gtc aac gag att cta caa gca gac gca      1779
Tyr Gly Ile Val Ala Lys Lys Val Asn Glu Ile Leu Gln Ala Asp Ala
575                 580                 585                 590
```

| | |
|---|---|
| atc aat ggg acc gat aac gaa gta gtt acc gtg acc gat gag aac act<br>Ile Asn Gly Thr Asp Asn Glu Val Val Thr Val Thr Asp Glu Asn Thr<br>    595                 600                 605 | 1827 |
| ggt gaa atc tct gag aaa gtc aag ctg ggc act aag gca ctg gct ggt<br>Gly Glu Ile Ser Glu Lys Val Lys Leu Gly Thr Lys Ala Leu Ala Gly<br>610                 615                 620 | 1875 |
| caa tgg ctg gct cac ggt gtt act cgc agt gtg act aag cgt tca gtc<br>Gln Trp Leu Ala His Gly Val Thr Arg Ser Val Thr Lys Arg Ser Val<br>            625                 630                 635 | 1923 |
| atg acg ctg gct tac ggg tcc aaa gag ttc ggc ttc cgt caa caa gtg<br>Met Thr Leu Ala Tyr Gly Ser Lys Glu Phe Gly Phe Arg Gln Gln Val<br>    640                 645                 650 | 1971 |
| ctg gaa gat acc att cag cca gct att gat tcc ggc aag ggt ccg atg<br>Leu Glu Asp Thr Ile Gln Pro Ala Ile Asp Ser Gly Lys Gly Pro Met<br>655                 660                 665                 670 | 2019 |
| ttc act cag ccg aat cag gct gct gga tac atg gct aag ctg att tgg<br>Phe Thr Gln Pro Asn Gln Ala Ala Gly Tyr Met Ala Lys Leu Ile Trp<br>                675                 680                 685 | 2067 |
| gaa tct gtg agc gtg acg gtg gta gct gcg gtt gaa gca atg aac tgg<br>Glu Ser Val Ser Val Thr Val Val Ala Ala Val Glu Ala Met Asn Trp<br>        690                 695                 700 | 2115 |
| ctt aag tct gct gct aag ctg ctg gct gct gag gtc aaa gat aag aag<br>Leu Lys Ser Ala Ala Lys Leu Leu Ala Ala Glu Val Lys Asp Lys Lys<br>    705                 710                 715 | 2163 |
| act gga gag att ctt cgc aag cgt tgc gct gtg cat tgg gta act cct<br>Thr Gly Glu Ile Leu Arg Lys Arg Cys Ala Val His Trp Val Thr Pro<br>720                 725                 730 | 2211 |
| gat ggt ttc cct gtg tgg cag gaa tac aag aag cct att cag acg cgc<br>Asp Gly Phe Pro Val Trp Gln Glu Tyr Lys Lys Pro Ile Gln Thr Arg<br>735                 740                 745                 750 | 2259 |
| ttg aac ctg atg ttc ctc ggt cag ttc cgc tta cag cct acc att aac<br>Leu Asn Leu Met Phe Leu Gly Gln Phe Arg Leu Gln Pro Thr Ile Asn<br>                755                 760                 765 | 2307 |
| acc aac aaa gat agc gag att gat gca cac aaa cag gag tct ggt atc<br>Thr Asn Lys Asp Ser Glu Ile Asp Ala His Lys Gln Glu Ser Gly Ile<br>        770                 775                 780 | 2355 |
| gct cct aac ttt gta cac agc caa gac ggt agc cac ctt cgt aag act<br>Ala Pro Asn Phe Val His Ser Gln Asp Gly Ser His Leu Arg Lys Thr<br>    785                 790                 795 | 2403 |
| gta gtg tgg gca cac gag aag tac gga atc gaa tct ttt gca ctg att<br>Val Val Trp Ala His Glu Lys Tyr Gly Ile Glu Ser Phe Ala Leu Ile<br>800                 805                 810 | 2451 |
| cac gac tcc ttc ggt acc att ccg gct gac gct gcg aac ctg ttc aaa<br>His Asp Ser Phe Gly Thr Ile Pro Ala Asp Ala Ala Asn Leu Phe Lys<br>815                 820                 825                 830 | 2499 |
| gca gtg cgc gaa act atg gtt gac aca tat gag tct tgt gat gta ctg<br>Ala Val Arg Glu Thr Met Val Asp Thr Tyr Glu Ser Cys Asp Val Leu<br>                835                 840                 845 | 2547 |
| gct gat ttc tac gac cag ttc gct gac cag ttg cac gag tct caa ttg<br>Ala Asp Phe Tyr Asp Gln Phe Ala Asp Gln Leu His Glu Ser Gln Leu<br>        850                 855                 860 | 2595 |
| gac aaa atg cca gca ctt ccg gct aaa ggt aac ttg aac ctc cgt gac<br>Asp Lys Met Pro Ala Leu Pro Ala Lys Gly Asn Leu Asn Leu Arg Asp<br>    865                 870                 875 | 2643 |
| atc tta gag tcg gac ttc gcg ttc gcg tga taa<br>Ile Leu Glu Ser Asp Phe Ala Phe Ala<br>        880                 885 | 2676 |

<210> SEQ ID NO 11
<211> LENGTH: 887

```
<212> TYPE: PRT
<213> ORGANISM: Bacteriophage T7

<400> SEQUENCE: 11

Met Ala Pro Lys Lys Arg Lys Val Glu Asp Pro Lys Glu Phe Ser
1               5                   10                  15

Asp Ile Glu Leu Ala Ala Ile Pro Phe Asn Thr Leu Ala Asp His Tyr
            20                  25                  30

Gly Glu Arg Leu Ala Arg Glu Gln Leu Ala Leu Glu His Glu Ser Tyr
            35                  40                  45

Glu Met Gly Glu Ala Arg Phe Arg Lys Met Phe Glu Arg Gln Leu Lys
    50                  55                  60

Ala Gly Glu Val Ala Asp Asn Ala Ala Ala Lys Pro Leu Ile Thr Thr
65                  70                  75                  80

Leu Leu Pro Lys Met Ile Ala Arg Ile Asn Asp Trp Phe Glu Glu Val
                85                  90                  95

Lys Ala Lys Arg Gly Lys Arg Pro Thr Ala Phe Gln Phe Leu Gln Glu
            100                 105                 110

Ile Lys Pro Glu Ala Val Ala Tyr Ile Thr Ile Lys Thr Thr Leu Ala
        115                 120                 125

Cys Leu Thr Ser Ala Asp Asn Thr Thr Val Gln Ala Val Ala Ser Ala
130                 135                 140

Ile Gly Arg Ala Ile Glu Asp Glu Ala Arg Phe Gly Arg Ile Arg Asp
145                 150                 155                 160

Leu Glu Ala Lys His Phe Lys Lys Asn Val Glu Glu Gln Leu Asn Lys
                165                 170                 175

Arg Val Gly His Val Tyr Lys Lys Ala Phe Met Gln Val Val Glu Ala
            180                 185                 190

Asp Met Leu Ser Lys Gly Leu Leu Gly Gly Glu Ala Trp Ser Ser Trp
        195                 200                 205

His Lys Glu Asp Ser Ile His Val Gly Val Arg Cys Ile Glu Met Leu
    210                 215                 220

Ile Glu Ser Thr Gly Met Val Ser Leu His Arg Gln Asn Ala Gly Val
225                 230                 235                 240

Val Gly Gln Asp Ser Glu Thr Ile Glu Leu Ala Pro Glu Tyr Ala Glu
                245                 250                 255

Ala Ile Ala Thr Arg Ala Gly Ala Leu Ala Gly Ile Ser Pro Met Phe
            260                 265                 270

Gln Pro Cys Val Val Pro Pro Lys Pro Trp Thr Gly Ile Thr Gly Gly
        275                 280                 285

Gly Tyr Trp Ala Asn Gly Arg Arg Pro Leu Ala Leu Val Arg Thr His
    290                 295                 300

Ser Lys Lys Ala Leu Met Arg Tyr Glu Asp Val Tyr Met Pro Glu Val
305                 310                 315                 320

Tyr Lys Ala Ile Asn Ile Ala Gln Asn Thr Ala Trp Lys Ile Asn Lys
                325                 330                 335

Lys Val Leu Ala Val Ala Asn Val Ile Thr Lys Trp Lys His Cys Pro
            340                 345                 350

Val Glu Asp Ile Pro Ala Ile Glu Arg Glu Glu Leu Pro Met Lys Pro
        355                 360                 365

Glu Asp Ile Asp Met Asn Pro Glu Ala Leu Thr Ala Trp Lys Arg Ala
    370                 375                 380

Ala Ala Ala Val Tyr Arg Lys Asp Arg Ala Arg Lys Ser Arg Arg Ile
385                 390                 395                 400
```

```
Ser Leu Glu Phe Met Leu Glu Gln Ala Asn Lys Phe Ala Asn His Lys
                405                 410                 415
Ala Ile Trp Phe Pro Tyr Asn Met Asp Trp Arg Gly Arg Val Tyr Ala
            420                 425                 430
Val Ser Met Phe Asn Pro Gln Gly Asn Asp Met Thr Lys Gly Leu Leu
        435                 440                 445
Thr Leu Ala Lys Gly Lys Pro Ile Gly Lys Glu Gly Tyr Tyr Trp Leu
    450                 455                 460
Lys Ile His Gly Ala Asn Cys Ala Gly Val Asp Lys Val Pro Phe Pro
465                 470                 475                 480
Glu Arg Ile Lys Phe Ile Glu Glu Asn His Glu Asn Ile Met Ala Cys
                485                 490                 495
Ala Lys Ser Pro Leu Glu Asn Thr Trp Trp Ala Glu Gln Asp Ser Pro
            500                 505                 510
Phe Cys Phe Leu Ala Phe Cys Phe Glu Tyr Ala Gly Val Gln His His
        515                 520                 525
Gly Leu Ser Tyr Asn Cys Ser Leu Pro Leu Ala Phe Asp Gly Ser Cys
    530                 535                 540
Ser Gly Ile Gln His Phe Ser Ala Met Leu Arg Asp Glu Val Gly Gly
545                 550                 555                 560
Arg Ala Val Asn Leu Leu Pro Ser Glu Thr Val Gln Asp Ile Tyr Gly
                565                 570                 575
Ile Val Ala Lys Lys Val Asn Glu Ile Leu Gln Ala Asp Ala Ile Asn
            580                 585                 590
Gly Thr Asp Asn Glu Val Val Thr Val Thr Asp Glu Asn Thr Gly Glu
        595                 600                 605
Ile Ser Glu Lys Val Lys Leu Gly Thr Lys Ala Leu Ala Gly Gln Trp
    610                 615                 620
Leu Ala His Gly Val Thr Arg Ser Val Thr Lys Arg Ser Val Met Thr
625                 630                 635                 640
Leu Ala Tyr Gly Ser Lys Glu Phe Gly Phe Arg Gln Gln Val Leu Glu
                645                 650                 655
Asp Thr Ile Gln Pro Ala Ile Asp Ser Gly Lys Gly Pro Met Phe Thr
            660                 665                 670
Gln Pro Asn Gln Ala Ala Gly Tyr Met Ala Lys Leu Ile Trp Glu Ser
        675                 680                 685
Val Ser Val Thr Val Ala Ala Val Glu Ala Met Asn Trp Leu Lys
    690                 695                 700
Ser Ala Ala Lys Leu Leu Ala Ala Glu Val Lys Asp Lys Lys Thr Gly
705                 710                 715                 720
Glu Ile Leu Arg Lys Arg Cys Ala Val His Trp Val Thr Pro Asp Gly
                725                 730                 735
Phe Pro Val Trp Gln Glu Tyr Lys Lys Pro Ile Gln Thr Arg Leu Asn
            740                 745                 750
Leu Met Phe Leu Gly Gln Phe Arg Leu Gln Pro Thr Ile Asn Thr Asn
        755                 760                 765
Lys Asp Ser Glu Ile Asp Ala His Lys Gln Glu Ser Gly Ile Ala Pro
    770                 775                 780
Asn Phe Val His Ser Gln Asp Gly Ser His Leu Arg Lys Thr Val Val
785                 790                 795                 800
Trp Ala His Glu Lys Tyr Gly Ile Glu Ser Phe Ala Leu Ile His Asp
                805                 810                 815
Ser Phe Gly Thr Ile Pro Ala Asp Ala Ala Asn Leu Phe Lys Ala Val
            820                 825                 830
```

-continued

```
Arg Glu Thr Met Val Asp Thr Tyr Glu Ser Cys Asp Val Leu Ala Asp
        835                 840                 845

Phe Tyr Asp Gln Phe Ala Asp Gln Leu His Glu Ser Gln Leu Asp Lys
    850                 855                 860

Met Pro Ala Leu Pro Ala Lys Gly Asn Leu Asn Leu Arg Asp Ile Leu
865                 870                 875                 880

Glu Ser Asp Phe Ala Phe Ala
                885

<210> SEQ ID NO 12
<211> LENGTH: 1578
<212> TYPE: DNA
<213> ORGANISM: Measles virus
<220> FEATURE:
<221> NAME/KEY: CDS
<222> LOCATION: (1)..(1578)
<220> FEATURE:
<221> NAME/KEY: misc_feature
<222> LOCATION: (1)..(1578)
<223> OTHER INFORMATION: Schwarz MV N gene

<400> SEQUENCE: 12 atg gcc aca ctt tta agg agc tta gca ttg ttc aaa aga aac aag gac       48
Met Ala Thr Leu Leu Arg Ser Leu Ala Leu Phe Lys Arg Asn Lys Asp
1               5                   10                  15 aaa cca ccc att aca tca gga tcc ggt gga gcc atc aga gga atc aaa       96
Lys Pro Pro Ile Thr Ser Gly Ser Gly Gly Ala Ile Arg Gly Ile Lys
            20                  25                  30 cac att att ata gta cca atc cct gga gat tcc tca att acc act cga      144
His Ile Ile Ile Val Pro Ile Pro Gly Asp Ser Ser Ile Thr Thr Arg
        35                  40                  45 tcc aga ctt ctg gac cgg ttg gtg agg tta att gga aac ccg gat gtg      192
Ser Arg Leu Leu Asp Arg Leu Val Arg Leu Ile Gly Asn Pro Asp Val
    50                  55                  60 agc ggg ccc aaa cta aca ggg gca cta ata ggt ata tta tcc tta ttt      240
Ser Gly Pro Lys Leu Thr Gly Ala Leu Ile Gly Ile Leu Ser Leu Phe
65                  70                  75                  80 gtg gag tct cca ggt caa ttg att cag agg atc acc gat gac cct gac      288
Val Glu Ser Pro Gly Gln Leu Ile Gln Arg Ile Thr Asp Asp Pro Asp
                85                  90                  95 gtt agc ata agg ctg tta gag gtt gtc cag agt gac cag tca caa tct      336
Val Ser Ile Arg Leu Leu Glu Val Val Gln Ser Asp Gln Ser Gln Ser
            100                 105                 110 ggc ctt acc ttc gca tca aga ggt acc aac atg gag gat gag gcg gac      384
Gly Leu Thr Phe Ala Ser Arg Gly Thr Asn Met Glu Asp Glu Ala Asp
        115                 120                 125 caa tac ttt tca cat gat gat cca att agt agt gat caa tcc agg ttc      432
Gln Tyr Phe Ser His Asp Asp Pro Ile Ser Ser Asp Gln Ser Arg Phe
    130                 135                 140 gga tgg ttc ggg aac aag gaa atc tca gat att gaa gtg caa gac cct      480
Gly Trp Phe Gly Asn Lys Glu Ile Ser Asp Ile Glu Val Gln Asp Pro
145                 150                 155                 160 gag gga ttc aac atg att ctg ggt acc atc cta gcc caa att tgg gtc      528
Glu Gly Phe Asn Met Ile Leu Gly Thr Ile Leu Ala Gln Ile Trp Val
                165                 170                 175 ttg ctc gca aag gcg gtt acg gcc cca gac acg gca gct gat tcg gag      576
Leu Leu Ala Lys Ala Val Thr Ala Pro Asp Thr Ala Ala Asp Ser Glu
            180                 185                 190 cta aga agg tgg ata aag tac acc caa caa aga agg gta gtt ggt gaa      624
Leu Arg Arg Trp Ile Lys Tyr Thr Gln Gln Arg Arg Val Val Gly Glu
        195                 200                 205
```

```
ttt aga ttg gag aga aaa tgg ttg gat gtg gtg agg aac agg att gcc      672
Phe Arg Leu Glu Arg Lys Trp Leu Asp Val Val Arg Asn Arg Ile Ala
    210                 215                 220 gag gac ctc tcc tta cgc cga ttc atg gtc gct cta atc ctg gat atc      720
Glu Asp Leu Ser Leu Arg Arg Phe Met Val Ala Leu Ile Leu Asp Ile
225                 230                 235                 240 aag aga aca ccc gga aac aaa ccc agg att gct gaa atg ata tgt gac      768
Lys Arg Thr Pro Gly Asn Lys Pro Arg Ile Ala Glu Met Ile Cys Asp
                245                 250                 255 att gat aca tat atc gta gag gca gga tta gcc agt ttt atc ctg act      816
Ile Asp Thr Tyr Ile Val Glu Ala Gly Leu Ala Ser Phe Ile Leu Thr
            260                 265                 270 att aag ttt ggg ata gaa act atg tat cct gct ctt gga ctg cat gaa      864
Ile Lys Phe Gly Ile Glu Thr Met Tyr Pro Ala Leu Gly Leu His Glu
        275                 280                 285 ttt gct ggt gag tta tcc aca ctt gag tcc ttg atg aac ctt tac cag      912
Phe Ala Gly Glu Leu Ser Thr Leu Glu Ser Leu Met Asn Leu Tyr Gln
    290                 295                 300 caa atg ggg gaa act gca ccc tac atg gta atc ctg gag aac tca att      960
Gln Met Gly Glu Thr Ala Pro Tyr Met Val Ile Leu Glu Asn Ser Ile
305                 310                 315                 320 cag aac aag ttc agt gca gga tca tac cct ctg ctc tgg agc tat gcc     1008
Gln Asn Lys Phe Ser Ala Gly Ser Tyr Pro Leu Leu Trp Ser Tyr Ala
                325                 330                 335 atg gga gta gga gtg gaa ctt gaa aac tcc atg gga ggt ttg aac ttt     1056
Met Gly Val Gly Val Glu Leu Glu Asn Ser Met Gly Gly Leu Asn Phe
            340                 345                 350 ggc cga tct tac ttt gat cca gca tat ttt aga tta ggg caa gag atg     1104
Gly Arg Ser Tyr Phe Asp Pro Ala Tyr Phe Arg Leu Gly Gln Glu Met
        355                 360                 365 gta agg agg tca gct gga aag gtc agt tcc aca ttg gca tct gaa ctc     1152
Val Arg Arg Ser Ala Gly Lys Val Ser Ser Thr Leu Ala Ser Glu Leu
    370                 375                 380 ggt atc act gcc gag gat gca agg ctt gtt tca gag att gca atg cat     1200
Gly Ile Thr Ala Glu Asp Ala Arg Leu Val Ser Glu Ile Ala Met His
385                 390                 395                 400 act act gag gac aag atc agt aga gcg gtt gga ccc aga caa gcc caa     1248
Thr Thr Glu Asp Lys Ile Ser Arg Ala Val Gly Pro Arg Gln Ala Gln
                405                 410                 415 gta tca ttt cta cac ggt gat caa agt gag aat gag cta ccg aga ttg     1296
Val Ser Phe Leu His Gly Asp Gln Ser Glu Asn Glu Leu Pro Arg Leu
            420                 425                 430 ggg ggc aag gaa gat agg agg gtc aaa cag agt cga gga gaa gcc agg     1344
Gly Gly Lys Glu Asp Arg Arg Val Lys Gln Ser Arg Gly Glu Ala Arg
        435                 440                 445 gag agc tac aga gaa acc ggg ccc agc aga gca agt gat gcg aga gct     1392
Glu Ser Tyr Arg Glu Thr Gly Pro Ser Arg Ala Ser Asp Ala Arg Ala
    450                 455                 460 gcc cat ctt cca acc ggc aca ccc cta gac att gac act gca acg gag     1440
Ala His Leu Pro Thr Gly Thr Pro Leu Asp Ile Asp Thr Ala Thr Glu
465                 470                 475                 480 tcc agc caa gat ccg cag gac agt cga agg tca gct gac gcc ctg ctt     1488
Ser Ser Gln Asp Pro Gln Asp Ser Arg Arg Ser Ala Asp Ala Leu Leu
                485                 490                 495 agg ctg caa gcc atg gca gga atc tcg gaa gaa caa ggc tca gac acg     1536
Arg Leu Gln Ala Met Ala Gly Ile Ser Glu Glu Gln Gly Ser Asp Thr
            500                 505                 510 gac acc cct ata gtg tac aat gac aga aat ctt cta gac tag              1578
Asp Thr Pro Ile Val Tyr Asn Asp Arg Asn Leu Leu Asp
        515                 520                 525
```

<210> SEQ ID NO 13
<211> LENGTH: 525
<212> TYPE: PRT
<213> ORGANISM: Measles virus

<400> S

```
Gly Ile Thr Ala Glu Asp Ala Arg Leu Val Ser Glu Ile Ala Met His
385                 390                 395                 400

Thr Thr Glu Asp Lys Ile Ser Arg Ala Val Gly Pro Arg Gln Ala Gln
            405                 410                 415

Val Ser Phe Leu His Gly Asp Gln Ser Glu Asn Glu Leu Pro Arg Leu
        420                 425                 430

Gly Gly Lys Glu Asp Arg Arg Val Lys Gln Ser Arg Gly Glu Ala Arg
            435                 440                 445

Glu Ser Tyr Arg Glu Thr Gly Pro Ser Arg Ala Ser Asp Ala Arg Ala
        450                 455                 460

Ala His Leu Pro Thr Gly Thr Pro Leu Asp Ile Asp Thr Ala Thr Glu
465                 470                 475                 480

Ser Ser Gln Asp Pro Gln Asp Ser Arg Arg Ser Ala Asp Ala Leu Leu
            485                 490                 495

Arg Leu Gln Ala Met Ala Gly Ile Ser Glu Glu Gln Gly Ser Asp Thr
        500                 505                 510

Asp Thr Pro Ile Val Tyr Asn Asp Arg Asn Leu Leu Asp
        515                 520                 525

<210> SEQ ID NO 14
<211> LENGTH: 1524
<212> TYPE: DNA
<213> ORGANISM: Measles virus
<220> FEATURE:
<221> NAME/KEY: CDS
<222> LOCATION: (1)..(1524)
<220> FEATURE:
<221> NAME/KEY: misc_feature
<222> LOCAT

```
                145                 150                 155                 160
gag gga tat gct atc act gac cgg gga tct gct ccc atc tct atg ggg       528
Glu Gly Tyr Ala Ile Thr Asp Arg Gly Ser Ala Pro Ile Ser Met Gly
                165                 170                 175 ttc agg gct tct gat gtt gaa act gca gaa ggg gag atc cac gag           576
Phe Arg Ala Ser Asp Val Glu Thr Ala Glu Gly Gly Glu Ile His Glu
            180                 185                 190 ctc ctg aga ctc caa tcc aga ggc aac aac ttt ccg aag ctt ggg aaa       624
Leu Leu Arg Leu Gln Ser Arg Gly Asn Asn Phe Pro Lys Leu Gly Lys
        195                 200                 205 act ctc aat gtt cct ccg ccc ccg gac ccc ggt agg gcc agc act tcc       672
Thr Leu Asn Val Pro Pro Pro Pro Asp Pro Gly Arg Ala Ser Thr Ser
    210                 215                 220 ggg aca ccc att aaa aag ggc aca gac gcg aga tta gcc tca ttt gga       720
Gly Thr Pro Ile Lys Lys Gly Thr Asp Ala Arg Leu Ala Ser Phe Gly
225                 230                 235                 240 acg gag atc gcg tct tta ttg aca ggt ggt gca acc caa tgt gct cga       768
Thr Glu Ile Ala Ser Leu Leu Thr Gly Gly Ala Thr Gln Cys Ala Arg
                245                 250                 255 aag tca ccc tcg gaa cca tca ggg cca ggt gca cct gcg ggg aat gtc       816
Lys Ser Pro Ser Glu Pro Ser Gly Pro Gly Ala Pro Ala Gly Asn Val
            260                 265                 270 ccc gag tgt gtg agc aat gcc gca ctg ata cag gag tgg aca ccc gaa       864
Pro Glu Cys Val Ser Asn Ala Ala Leu Ile Gln Glu Trp Thr Pro Glu
        275                 280                 285 tct ggt acc aca atc tcc ccg aga tcc cag aat aat gaa gaa ggg gga       912
Ser Gly Thr Thr Ile Ser Pro Arg Ser Gln Asn Asn Glu Glu Gly Gly
    290                 295                 300 gac tat tat gat gat gag ctg ttc tct gat gtc caa gat att aaa aca       960
Asp Tyr Tyr Asp Asp Glu Leu Phe Ser Asp Val Gln Asp Ile Lys Thr
305                 310                 315                 320 gcc ttg gcc aaa ata cac gag gat aat cag aag ata atc tcc aag cta      1008
Ala Leu Ala Lys Ile His Glu Asp Asn Gln Lys Ile Ile Ser Lys Leu
                325                 330                 335 gaa tca ctg ctg tta ttg aag gga gaa gtt gag tca att aag aag cag      1056
Glu Ser Leu Leu Leu Leu Lys Gly Glu Val Glu Ser Ile Lys Lys Gln
            340                 345                 350 atc aac agg caa aat atc agc ata tcc acc ctg gaa gga cac ctc tca      1104
Ile Asn Arg Gln Asn Ile Ser Ile Ser Thr Leu Glu Gly His Leu Ser
        355                 360                 365 agc atc atg atc gcc att cct gga ctt ggg aag gat ccc aac gac ccc      1152
Ser Ile Met Ile Ala Ile Pro Gly Leu Gly Lys Asp Pro Asn Asp Pro
    370                 375                 380 act gca gat gtc gaa atc aat ccc gac ttg aaa ccc atc ata ggc aga      1200
Thr Ala Asp Val Glu Ile Asn Pro Asp Leu Lys Pro Ile Ile Gly Arg
385                 390                 395                 400 gat tca ggc cga gca ctg gcc gaa gtt ctc aag aaa ccc gtt gcc agc      1248
Asp Ser Gly Arg Ala Leu Ala Glu Val Leu Lys Lys Pro Val Ala Ser
                405                 410                 415 cga caa ctc caa gga atg aca aat gga cgg acc agt tcc aga gga cag      1296
Arg Gln Leu Gln Gly Met Thr Asn Gly Arg Thr Ser Ser Arg Gly Gln
            420                 425                 430 ctg ctg aag gaa ttt cag cta aag ccg atc ggg aaa aag atg agc tca      1344
Leu Leu Lys Glu Phe Gln Leu Lys Pro Ile Gly Lys Lys Met Ser Ser
        435                 440                 445 gcc gtc ggg ttt gtt cct gac acc ggc cct gca tca cgc agt gta atc      1392
Ala Val Gly Phe Val Pro Asp Thr Gly Pro Ala Ser Arg Ser Val Ile
    450                 455                 460 cgc tcc att ata aaa tcc agc cgg cta gag gag gat cgg aag cgt tac      1440
Arg Ser Ile Ile Lys Ser Ser Arg Leu Glu Glu Asp Arg Lys Arg Tyr
```

```
                     465              470              475              480
ctg atg act ctc ctt gat gat atc aaa gga gcc aat gat ctt gcc aag       1488
Leu Met Thr Leu Leu Asp Asp Ile Lys Gly Ala Asn Asp Leu Ala Lys
                     485              490              495 ttc cac cag atg ctg atg aag ata ata atg aag tag                       1524
Phe His Gln Met Leu Met Lys Ile Ile Met Lys
        500                  505
```

<210> SEQ ID NO 15
<211> LENGTH: 507
<212> TYPE: PRT
<213> ORGANISM: Measles virus

<400> SEQUENCE: 15

```
Met Ala Glu Glu Gln Ala Arg His Val Lys Asn Gly Leu Glu Cys Ile
1               5                   10                  15

Arg Ala Leu Lys Ala Glu Pro Ile Gly Ser Leu Ala Ile Glu Glu Ala
                20                  25                  30

Met Ala Ala Trp Ser Glu Ile Ser Asp Asn Pro Gly Gln Glu Arg Ala
            35                  40                  45

Thr Cys Arg Glu Glu Lys Ala Gly Ser Ser Gly Leu Ser Lys Pro Cys
50                  55                  60

Leu Ser Ala Ile Gly Ser Thr Glu Gly Gly Ala Pro Arg Ile Arg Gly
65                  70                  75                  80

Gln Gly Pro Gly Glu Ser Asp Asp Asp Ala Glu Thr Leu Gly Ile Pro
                85                  90                  95

Pro Arg Asn Leu Gln Ala Ser Ser Thr Gly Leu Gln Cys Tyr Tyr Val
                100                 105                 110

Tyr Asp His Ser Gly Glu Ala Val Lys Gly Ile Gln Asp Ala Asp Ser
            115                 120                 125

Ile Met Val Gln Ser Gly Leu Asp Gly Asp Ser Thr Leu Ser Gly Gly
130                 135                 140

Asp Asn Glu Ser Glu Asn Ser Asp Val Asp Ile Gly Glu Pro Asp Thr
145                 150                 155                 160

Glu Gly Tyr Ala Ile Thr Asp Arg Gly Ser Ala Pro Ile Ser Met Gly
                165                 170                 175

Phe Arg Ala Ser Asp Val Glu Thr Ala Glu Gly Gly Glu Ile His Glu
            180                 185                 190

Leu Leu Arg Leu Gln Ser Arg Gly Asn Asn Phe Pro Lys Leu Gly Lys
        195                 200                 205

Thr Leu Asn Val Pro Pro Pro Asp Pro Gly Arg Ala Ser Thr Ser
210                 215                 220

Gly Thr Pro Ile Lys Lys Gly Thr Asp Ala Arg Leu Ala Ser Phe Gly
225                 230                 235                 240

Thr Glu Ile Ala Ser Leu Leu Thr Gly Gly Ala Thr Gln Cys Ala Arg
                245                 250                 255

Lys Ser Pro Ser Glu Pro Ser Gly Pro Gly Ala Pro Ala Gly Asn Val
            260                 265                 270

Pro Glu Cys Val Ser Asn Ala Ala Leu Ile Gln Glu Trp Thr Pro Glu
        275                 280                 285

Ser Gly Thr Thr Ile Ser Pro Arg Ser Gln Asn Asn Glu Glu Gly Gly
    290                 295                 300

Asp Tyr Tyr Asp Asp Glu Leu Phe Ser Asp Val Gln Asp Ile Lys Thr
305                 310                 315                 320

Ala Leu Ala Lys Ile His Glu Asp Asn Gln Lys Ile Ile Ser Lys Leu
                325                 330                 335
```

-continued

Glu Ser Leu Leu Leu Leu Lys Gly Glu Val Glu Ser Ile Lys Lys Gln
340 345 350

Ile Asn Arg Gln Asn Ile Ser Ile Ser Thr Leu Glu Gly His Leu Ser
355 360 365

Ser Ile Met Ile Ala Ile Pro Gly Leu Gly Lys Asp Pro Asn Asp Pro
370 375 380

Thr Ala Asp Val Glu Ile Asn Pro Asp Leu Lys Pro Ile Ile Gly Arg
385 390 395 400

Asp Ser Gly Arg Ala Leu Ala Glu Val Leu Lys Lys Pro Val Ala Ser
405 410 415

Arg Gln Leu Gln Gly Met Thr Asn Gly Arg Thr Ser Ser Arg Gly Gln
420 425 430

Leu Leu Lys Glu Phe Gln Leu Lys Pro Ile Gly Lys Lys Met Ser Ser
435 440 445

Ala Val Gly Phe Val Pro Asp Thr Gly Pro Ala Ser Arg Ser Val Ile
450 455 460

Arg Ser Ile Ile Lys Ser Ser Arg Leu Glu Glu Asp Arg Lys Arg Tyr
465 470 475 480

Leu Met Thr Leu Leu Asp Asp Ile Lys Gly Ala Asn Asp Leu Ala Lys
485 490 495

Phe His Gln Met Leu Met Lys Ile Ile Met Lys
500 505

<210> SEQ ID NO 16
<211> LENGTH: 6552
<212> TYPE: DNA
<213> ORGANISM: Measles virus
<220> FEATURE:
<221> NAME/KEY: CDS
<222> LOCATION: (1)..(6552)
<220> FEATURE:
<221> NAME/KEY: misc_feature
<222> LOCATION: (1)..(6555)
<223> OTHER INFORMATION: Schwarz MV L gene

<400> SEQUENCE: 16 atg gac tcg cta tct gtc aac cag atc tta tac cct gaa gtt cac cta 48
Met Asp Ser Leu Ser Val Asn Gln Ile Leu Tyr Pro Glu Val His Leu
1 5 10 15 gat agc ccg ata gtt acc aat aag ata gta gcc atc ctg gag tat gct 96
Asp Ser Pro Ile Val Thr Asn Lys Ile Val Ala Ile Leu Glu Tyr Ala
20 25 30 cga gtc cct cac gct tac agc ctg gag gac cct aca ctg tgt cag aac 144
Arg Val Pro His Ala Tyr Ser Leu Glu Asp Pro Thr Leu Cys Gln Asn
35 40 45 atc aag cac cgc cta aaa aac gga ttt tcc aac caa atg att ata aac 192
Ile Lys His Arg Leu Lys Asn Gly Phe Ser Asn Gln Met Ile Ile Asn
50 55 60 aat gtg gaa gtt ggg aat gtc atc aag tcc aag ctt agg agt tat ccg 240
Asn Val Glu Val Gly Asn Val Ile Lys Ser Lys Leu Arg Ser Tyr Pro
65 70 75 80 gcc cac tct cat att cca tat cca aat tgt aat cag gat tta ttt aac 288
Ala His Ser His Ile Pro Tyr Pro Asn Cys Asn Gln Asp Leu Phe Asn
85 90 95 ata gaa gac aaa gag tca acg agg aag atc cgt gaa ctc ctc aaa aag 336
Ile Glu Asp Lys Glu Ser Thr Arg Lys Ile Arg Glu Leu Leu Lys Lys
100 105 110 ggg aat tcg ctg tac tcc aaa gtc agt gat aag gtt ttc caa tgc tta 384
Gly Asn Ser Leu Tyr Ser Lys Val Ser Asp Lys Val Phe Gln Cys Leu
115 120 125

```
agg gac act aac tca cgg ctt ggc cta ggc tcc gaa ttg agg gag gac    432
Arg Asp Thr Asn Ser Arg Leu Gly Leu Gly Ser Glu Leu Arg Glu Asp
        130                 135                 140 atc aag gag aaa gtt att aac ttg gga gtt tac atg cac agc tcc cag    480
Ile Lys Glu Lys Val Ile Asn Leu Gly Val Tyr Met His Ser Ser Gln
145                 150                 155                 160 tgg ttt gag ccc ttt ctg ttt tgg ttt aca gtc aag act gag atg agg    528
Trp Phe Glu Pro Phe Leu Phe Trp Phe Thr Val Lys Thr Glu Met Arg
                165                 170                 175 tca gtg att aaa tca caa acc cat act tgc cat agg agg aga cac aca    576
Ser Val Ile Lys Ser Gln Thr His Thr Cys His Arg Arg Arg His Thr
            180                 185                 190 cct gta ttc ttc act ggt agt tca gtt gag ttg cta atc tct cgt gac    624
Pro Val Phe Phe Thr Gly Ser Ser Val Glu Leu Leu Ile Ser Arg Asp
        195                 200                 205 ctt gtt gct ata atc agt aaa gag tct caa cat gta tat tac ctg aca    672
Leu Val Ala Ile Ile Ser Lys Glu Ser Gln His Val Tyr Tyr Leu Thr
        210                 215                 220 ttt gaa ctg gtt ttg atg tat tgt gat gtc ata gag ggg agg tta atg    720
Phe Glu Leu Val Leu Met Tyr Cys Asp Val Ile Glu Gly Arg Leu Met
225                 230                 235                 240 aca gag acc gct atg act att gat gct agg tat aca gag ctt cta gga    768
Thr Glu Thr Ala Met Thr Ile Asp Ala Arg Tyr Thr Glu Leu Leu Gly
                245                 250                 255 aga gtc aga tac atg tgg aaa ctg ata gat ggt ttc ttc cct gca ctc    816
Arg Val Arg Tyr Met Trp Lys Leu Ile Asp Gly Phe Phe Pro Ala Leu
            260                 265                 270 ggg aat cca act tat caa att gta gcc atg ctg gag cct ctt tca ctt    864
Gly Asn Pro Thr Tyr Gln Ile Val Ala Met Leu Glu Pro Leu Ser Leu
        275                 280                 285 gct tac ctg cag ctg agg gat ata aca gta gaa ctc aga ggt gct ttc    912
Ala Tyr Leu Gln Leu Arg Asp Ile Thr Val Glu Leu Arg Gly Ala Phe
        290                 295                 300 ctt aac cac tgc ttt act gaa ata cat gat gtt ctt gac caa aac ggg    960
Leu Asn His Cys Phe Thr Glu Ile His Asp Val Leu Asp Gln Asn Gly
305                 310                 315                 320 ttt tct gat gaa ggt act tat cat gag tta act gaa gct cta gat tac   1008
Phe Ser Asp Glu Gly Thr Tyr His Glu Leu Thr Glu Ala Leu Asp Tyr
                325                 330                 335 att ttc ata act gat gac ata cat ctg aca ggg gag att ttc tca ttt   1056
Ile Phe Ile Thr Asp Asp Ile His Leu Thr Gly Glu Ile Phe Ser Phe
            340                 345                 350 ttc aga agt ttc ggc cac ccc aga ctt gaa gca gta acg gct gct gaa   1104
Phe Arg Ser Phe Gly His Pro Arg Leu Glu Ala Val Thr Ala Ala Glu
        355                 360                 365 aat gtt agg aaa tac atg aat cag cct aaa gtc att gtg tat gag act   1152
Asn Val Arg Lys Tyr Met Asn Gln Pro Lys Val Ile Val Tyr Glu Thr
        370                 375                 380 ctg atg aaa ggt cat gcc ata ttt tgt gga atc ata atc aac ggc tat   1200
Leu Met Lys Gly His Ala Ile Phe Cys Gly Ile Ile Ile Asn Gly Tyr
385                 390                 395                 400 cgt gac agg cac gga ggc agt tgg cca ccg ctg acc ctc ccc ctg cat   1248
Arg Asp Arg His Gly Gly Ser Trp Pro Pro Leu Thr Leu Pro Leu His
                405                 410                 415 gct gca gac aca atc cgg aat gct caa gct tca ggt gaa ggg tta aca   1296
Ala Ala Asp Thr Ile Arg Asn Ala Gln Ala Ser Gly Glu Gly Leu Thr
            420                 425                 430 cat gag cag tgc gtt gat aac tgg aaa tct ttt gct gga gtg aaa ttt   1344
His Glu Gln Cys Val Asp Asn Trp Lys Ser Phe Ala Gly Val Lys Phe
        435                 440                 445
```

| | | | | | | | | | | | | | | | |
|---|---|---|---|---|---|---|---|---|---|---|---|---|---|---|---|
| ggc | tgc | ttt | atg | cct | ctt | agc | ctg | gat | agt | gat | ctg | aca | atg | tac | cta | 1392 |
| Gly | Cys | Phe | Met | Pro | Leu | Ser | Leu | Asp | Ser | Asp | Leu | Thr | Met | Tyr | Leu |
| 450 | | | | 455 | | | | | 460 | | | | |

```
ggc tgc ttt atg cct ctt agc ctg gat agt gat ctg aca atg tac cta       1392
Gly Cys Phe Met Pro Leu Ser Leu Asp Ser Asp Leu Thr Met Tyr Leu
450                 455                 460 aag gac aag gca ctt gct gct ctc caa agg gaa tgg gat tca gtt tac       1440
Lys Asp Lys Ala Leu Ala Ala Leu Gln Arg Glu Trp Asp Ser Val Tyr
465                 470                 475                 480 ccg aaa gag ttc ctg cgt tac gac cct ccc aag gga acc ggg tca cgg       1488
Pro Lys Glu Phe Leu Arg Tyr Asp Pro Pro Lys Gly Thr Gly Ser Arg
            485                 490                 495 agg ctt gta gat gtt ttc ctt aat gat tcg agc ttt gac cca tat gat       1536
Arg Leu Val Asp Val Phe Leu Asn Asp Ser Ser Phe Asp Pro Tyr Asp
                500                 505                 510 gtg ata atg tat gtt gta agt gga gct tac ctc cat gac cct gag ttc       1584
Val Ile Met Tyr Val Val Ser Gly Ala Tyr Leu His Asp Pro Glu Phe
        515                 520                 525 aac ctg tct tac agc ctg aaa gaa aag gag atc aag gaa aca ggt aga       1632
Asn Leu Ser Tyr Ser Leu Lys Glu Lys Glu Ile Lys Glu Thr Gly Arg
    530                 535                 540 ctt ttt gct aaa atg act tac aaa atg agg gca tgc caa gtg att gct       1680
Leu Phe Ala Lys Met Thr Tyr Lys Met Arg Ala Cys Gln Val Ile Ala
545                 550                 555                 560 gaa aat cta atc tca aac ggg att ggc aaa tat ttt aag gac aat ggg       1728
Glu Asn Leu Ile Ser Asn Gly Ile Gly Lys Tyr Phe Lys Asp Asn Gly
                565                 570                 575 atg gcc aag gat gag cac gat ttg act aag gca ctc cac act cta gct       1776
Met Ala Lys Asp Glu His Asp Leu Thr Lys Ala Leu His Thr Leu Ala
        580                 585                 590 gtc tca gga gtc ccc aaa gat ctc aaa gaa agt cac agg ggg ggg cca       1824
Val Ser Gly Val Pro Lys Asp Leu Lys Glu Ser His Arg Gly Gly Pro
    595                 600                 605 gtc tta aaa acc tac tcc cga agc cca gtc cac aca agt acc agg aac       1872
Val Leu Lys Thr Tyr Ser Arg Ser Pro Val His Thr Ser Thr Arg Asn
610                 615                 620 gtg aga gca gca aaa ggg ttt ata ggg ttc cct caa gta att cgg cag       1920
Val Arg Ala Ala Lys Gly Phe Ile Gly Phe Pro Gln Val Ile Arg Gln
625                 630                 635                 640 gac caa gac act gat cat ccg gag aat atg gaa gct tac gag aca gtc       1968
Asp Gln Asp Thr Asp His Pro Glu Asn Met Glu Ala Tyr Glu Thr Val
                645                 650                 655 agt gca ttt atc acg act gat ctc aag aag tac tgc ctt aat tgg aga       2016
Ser Ala Phe Ile Thr Thr Asp Leu Lys Lys Tyr Cys Leu Asn Trp Arg
        660                 665                 670 tat gag acc atc agc ttg ttt gca cag agg cta aat gag att tac gga       2064
Tyr Glu Thr Ile Ser Leu Phe Ala Gln Arg Leu Asn Glu Ile Tyr Gly
    675                 680                 685 ttg ccc tca ttt ttc cag tgg ctg cat aag agg ctt gag acc tct gtc       2112
Leu Pro Ser Phe Phe Gln Trp Leu His Lys Arg Leu Glu Thr Ser Val
690                 695                 700 ctg tat gta agt gac cct cat tgc ccc ccc gac ctt gac gcc cat atc       2160
Leu Tyr Val Ser Asp Pro His Cys Pro Pro Asp Leu Asp Ala His Ile
705                 710                 715                 720 ccg tta tat aaa gtc ccc aat gat caa atc ttc att aag tac cct atg       2208
Pro Leu Tyr Lys Val Pro Asn Asp Gln Ile Phe Ile Lys Tyr Pro Met
                725                 730                 735 gga ggt ata gaa ggg tat tgt cag aag ctg tgg acc atc agc acc att       2256
Gly Gly Ile Glu Gly Tyr Cys Gln Lys Leu Trp Thr Ile Ser Thr Ile
        740                 745                 750 ccc tat cta tac ctg gct gct tat gag agc gga gta agg att gct tcg       2304
Pro Tyr Leu Tyr Leu Ala Ala Tyr Glu Ser Gly Val Arg Ile Ala Ser
    755                 760                 765
```

|                                                                                                                               |      |
|-------------------------------------------------------------------------------------------------------------------------------|------|
| tta gtg caa ggg gac aat cag acc ata gcc gta aca aaa agg gta ccc<br>Leu Val Gln Gly Asp Asn Gln Thr Ile Ala Val Thr Lys Arg Val Pro<br>770 775 780 | 2352 |
| agc aca tgg ccc tac aac ctt aag aaa cgg gaa gct gct aga gta act<br>Ser Thr Trp Pro Tyr Asn Leu Lys Lys Arg Glu Ala Ala Arg Val Thr<br>785 790 795 800 | 2400 |
| aga gat tac ttt gta att ctt agg caa agg cta cat gat att ggc cat<br>Arg Asp Tyr Phe Val Ile Leu Arg Gln Arg Leu His Asp Ile Gly His<br>805 810 815 | 2448 |
| cac ctc aag gca aat gag aca att gtt tca tca cat ttt ttt gtc tat<br>His Leu Lys Ala Asn Glu Thr Ile Val Ser Ser His Phe Phe Val Tyr<br>820 825 830 | 2496 |
| tca aaa gga ata tat tat gat ggg cta ctt gtg tcc caa tca ctc aag<br>Ser Lys Gly Ile Tyr Tyr Asp Gly Leu Leu Val Ser Gln Ser Leu Lys<br>835 840 845 | 2544 |
| agc atc gca aga tgt gta ttc tgg tca gag act ata gtt gat gaa aca<br>Ser Ile Ala Arg Cys Val Phe Trp Ser Glu Thr Ile Val Asp Glu Thr<br>850 855 860 | 2592 |
| agg gca gca tgc agt aat att gct aca aca atg gct aaa agc atc gag<br>Arg Ala Ala Cys Ser Asn Ile Ala Thr Thr Met Ala Lys Ser Ile Glu<br>865 870 875 880 | 2640 |
| aga ggt tat gac cgt tac ctt gca tat tcc ctg aac gtc cta aaa gtg<br>Arg Gly Tyr Asp Arg Tyr Leu Ala Tyr Ser Leu Asn Val Leu Lys Val<br>885 890 895 | 2688 |
| ata cag caa att ctg atc tct ctt ggc ttc aca atc aat tca acc atg<br>Ile Gln Gln Ile Leu Ile Ser Leu Gly Phe Thr Ile Asn Ser Thr Met<br>900 905 910 | 2736 |
| acc cgg gat gta gtc ata ccc ctc ctc aca aac aac gac ctc tta ata<br>Thr Arg Asp Val Val Ile Pro Leu Leu Thr Asn Asn Asp Leu Leu Ile<br>915 920 925 | 2784 |
| agg atg gca ctg ttg ccc gct cct att ggg ggg atg aat tat ctg aat<br>Arg Met Ala Leu Leu Pro Ala Pro Ile Gly Gly Met Asn Tyr Leu Asn<br>930 935 940 | 2832 |
| atg agc agg ctg ttt gtc aga aac atc ggt gat cca gta aca tca tca<br>Met Ser Arg Leu Phe Val Arg Asn Ile Gly Asp Pro Val Thr Ser Ser<br>945 950 955 960 | 2880 |
| att gct gat ctc aag aga atg att ctc gcc tca cta atg cct gaa gag<br>Ile Ala Asp Leu Lys Arg Met Ile Leu Ala Ser Leu Met Pro Glu Glu<br>965 970 975 | 2928 |
| acc ctc cat caa gta atg aca caa caa ccg ggg gac tct tca ttc cta<br>Thr Leu His Gln Val Met Thr Gln Gln Pro Gly Asp Ser Ser Phe Leu<br>980 985 990 | 2976 |
| gac tgg gct agc gac cct tac tca gca aat ctt gta tgt gtc cag agc<br>Asp Trp Ala Ser Asp Pro Tyr Ser Ala Asn Leu Val Cys Val Gln Ser<br>995 1000 1005 | 3024 |
| atc act aga ctc ctc aag aac ata act gca agg ttt gtc ctg atc<br>Ile Thr Arg Leu Leu Lys Asn Ile Thr Ala Arg Phe Val Leu Ile<br>1010 1015 1020 | 3069 |
| cat agt cca aac cca atg tta aaa gga tta ttc cat gat gac agt<br>His Ser Pro Asn Pro Met Leu Lys Gly Leu Phe His Asp Asp Ser<br>1025 1030 1035 | 3114 |
| aaa gaa gag gac gag gga ctg gcg gca ttc ctc atg gac agg cat<br>Lys Glu Glu Asp Glu Gly Leu Ala Ala Phe Leu Met Asp Arg His<br>1040 1045 1050 | 3159 |
| att ata gta cct agg gca gct cat gaa atc ctg gat cat agt gtc<br>Ile Ile Val Pro Arg Ala Ala His Glu Ile Leu Asp His Ser Val<br>1055 1060 1065 | 3204 |
| aca ggg gca aga gag tct att gca ggc atg ctg gat acc aca aaa<br>Thr Gly Ala Arg Glu Ser Ile Ala Gly Met Leu Asp Thr Thr Lys<br>1070 1075 1080 | 3249 |

```
ggc ttg att cga gcc agc atg agg aag ggg gga tta acc tct cga     3294
Gly Leu Ile Arg Ala Ser Met Arg Lys Gly Gly Leu Thr Ser Arg
    1085                1090                1095 gtg ata acc aga ttg tcc aat tat gac tat gaa caa ttc aga gca     3339
Val Ile Thr Arg Leu Ser Asn Tyr Asp Tyr Glu Gln Phe Arg Ala
    1100                1105                1110 ggg atg gtg cta ttg aca gga aga aag aga aat gtc ctc att gac     3384
Gly Met Val Leu Leu Thr Gly Arg Lys Arg Asn Val Leu Ile Asp
    1115                1120                1125 aaa gag tca tgt tca gtg cag ctg gcg aga gct cta aga agc cat     3429
Lys Glu Ser Cys Ser Val Gln Leu Ala Arg Ala Leu Arg Ser His
    1130                1135                1140 atg tgg gcg agg cta gct cga gga cgg cct att tac ggc ctt gag     3474
Met Trp Ala Arg Leu Ala Arg Gly Arg Pro Ile Tyr Gly Leu Glu
    1145                1150                1155 gtc cct gat gta cta gaa tct atg cga ggc cac ctt att cgg cgt     3519
Val Pro Asp Val Leu Glu Ser Met Arg Gly His Leu Ile Arg Arg
    1160                1165                1170 cat gag aca tgt gtc atc tgc gag tgt gga tca gtc aac tac gga     3564
His Glu Thr Cys Val Ile Cys Glu Cys Gly Ser Val Asn Tyr Gly
    1175                1180                1185 tgg ttt ttt gtc ccc tcg ggt tgc caa ctg gat gat att gac aag     3609
Trp Phe Phe Val Pro Ser Gly Cys Gln Leu Asp Asp Ile Asp Lys
    1190                1195                1200 gaa aca tca tcc ttg aga gtc cca tat att ggt tct acc act gat     3654
Glu Thr Ser Ser Leu Arg Val Pro Tyr Ile Gly Ser Thr Thr Asp
    1205                1210                1215 gag aga aca gac atg aag ctt gcc ttc gta aga gcc cca agt cga     3699
Glu Arg Thr Asp Met Lys Leu Ala Phe Val Arg Ala Pro Ser Arg
    1220                1225                1230 tcc ttg cga tct gct gtt aga ata gca aca gtg tac tca tgg gct     3744
Ser Leu Arg Ser Ala Val Arg Ile Ala Thr Val Tyr Ser Trp Ala
    1235                1240                1245 tac ggt gat gat gat agc tct tgg aac gaa gcc tgg ttg ttg gct     3789
Tyr Gly Asp Asp Asp Ser Ser Trp Asn Glu Ala Trp Leu Leu Ala
    1250                1255                1260 agg caa agg gcc aat gtg agc ctg gag gag cta agg gtg atc act     3834
Arg Gln Arg Ala Asn Val Ser Leu Glu Glu Leu Arg Val Ile Thr
    1265                1270                1275 ccc atc tca act tcg act aat tta gcg cat agg ttg agg gat cgt     3879
Pro Ile Ser Thr Ser Thr Asn Leu Ala His Arg Leu Arg Asp Arg
    1280                1285                1290 agc act caa gtg aaa tac tca ggt aca tcc ctt gtc cga gtg gcg     3924
Ser Thr Gln Val Lys Tyr Ser Gly Thr Ser Leu Val Arg Val Ala
    1295                1300                1305 agg tat acc aca atc tcc aac gac aat ctc tca ttt gtc ata tca     3969
Arg Tyr Thr Thr Ile Ser Asn Asp Asn Leu Ser Phe Val Ile Ser
    1310                1315                1320 gat aag aag gtt gat act aac ttt ata tac caa caa gga atg ctt     4014
Asp Lys Lys Val Asp Thr Asn Phe Ile Tyr Gln Gln Gly Met Leu
    1325                1330                1335 cta ggg ttg ggt gtt tta gaa aca ttg ttt cga ctc gag aaa gat     4059
Leu Gly Leu Gly Val Leu Glu Thr Leu Phe Arg Leu Glu Lys Asp
    1340                1345                1350 acc gga tca tct aac acg gta tta cat ctt cac gtc gaa aca gat     4104
Thr Gly Ser Ser Asn Thr Val Leu His Leu His Val Glu Thr Asp
    1355                1360                1365 tgt tgc gtg atc ccg atg ata gat cat ccc agg ata ccc agc tcc     4149
Cys Cys Val Ile Pro Met Ile Asp His Pro Arg Ile Pro Ser Ser
    1370                1375                1380
```

| | | | | | | | | | | | | |
|---|---|---|---|---|---|---|---|---|---|---|---|---|
| cgc | aag | cta | gag | ctg | agg | gca | gag | cta | tgt | acc | aac | cca ttg ata | 4194 |
| Arg | Lys | Leu | Glu | Leu | Arg | Ala | Glu | Leu | Cys | Thr | Asn | Pro Leu Ile | |
| 1385 | | | | 1390 | | | | 1395 | | | | | |
| tat | gat | aat | gca | cct | tta | att | gac | aga | gat | gca | aca | agg cta tac | 4239 |
| Tyr | Asp | Asn | Ala | Pro | Leu | Ile | Asp | Arg | Asp | Ala | Thr | Arg Leu Tyr | |
| 1400 | | | | | 1405 | | | | 1410 | | | | |
| acc | cag | agc | cat | agg | agg | cac | ctt | gtg | gaa | ttt | gtt | aca tgg tcc | 4284 |
| Thr | Gln | Ser | His | Arg | Arg | His | Leu | Val | Glu | Phe | Val | Thr Trp Ser | |
| 1415 | | | | | 1420 | | | | 1425 | | | | |
| aca | ccc | caa | cta | tat | cac | att | tta | gct | aag | tcc | aca | gca cta tct | 4329 |
| Thr | Pro | Gln | Leu | Tyr | His | Ile | Leu | Ala | Lys | Ser | Thr | Ala Leu Ser | |
| 1430 | | | | | 1435 | | | | 1440 | | | | |
| atg | att | gac | ctg | gta | aca | aaa | ttt | gag | aag | gac | cat | atg aat gaa | 4374 |
| Met | Ile | Asp | Leu | Val | Thr | Lys | Phe | Glu | Lys | Asp | His | Met Asn Glu | |
| 1445 | | | | | 1450 | | | | 1455 | | | | |
| att | tca | gct | ctc | ata | ggg | gat | gac | gat | atc | aat | agt | ttc ata act | 4419 |
| Ile | Ser | Ala | Leu | Ile | Gly | Asp | Asp | Asp | Ile | Asn | Ser | Phe Ile Thr | |
| 1460 | | | | | 1465 | | | | 1470 | | | | |
| gag | ttt | ctg | ctc | ata | gag | cca | aga | tta | ttc | act | atc | tac ttg ggc | 4464 |
| Glu | Phe | Leu | Leu | Ile | Glu | Pro | Arg | Leu | Phe | Thr | Ile | Tyr Leu Gly | |
| 1475 | | | | | 1480 | | | | 1485 | | | | |
| cag | tgt | gcg | gcc | atc | aat | tgg | gca | ttt | gat | gta | cat | tat cat aga | 4509 |
| Gln | Cys | Ala | Ala | Ile | Asn | Trp | Ala | Phe | Asp | Val | His | Tyr His Arg | |
| 1490 | | | | | 1495 | | | | 1500 | | | | |
| cca | tca | ggg | aaa | tat | cag | atg | ggt | gag | ctg | ttg | tca | tcg ttc ctt | 4554 |
| Pro | Ser | Gly | Lys | Tyr | Gln | Met | Gly | Glu | Leu | Leu | Ser | Ser Phe Leu | |
| 1505 | | | | | 1510 | | | | 1515 | | | | |
| tct | aga | atg | agc | aaa | gga | gtg | ttt | aag | gtg | ctt | gtc | aat gct cta | 4599 |
| Ser | Arg | Met | Ser | Lys | Gly | Val | Phe | Lys | Val | Leu | Val | Asn Ala Leu | |
| 1520 | | | | | 1525 | | | | 1530 | | | | |
| agc | cac | cca | aag | atc | tac | aag | aaa | ttc | tgg | cat | tgt | ggt att ata | 4644 |
| Ser | His | Pro | Lys | Ile | Tyr | Lys | Lys | Phe | Trp | His | Cys | Gly Ile Ile | |
| 1535 | | | | | 1540 | | | | 1545 | | | | |
| gag | cct | atc | cat | ggt | cct | tca | ctt | gat | gct | caa | aac | ttg cac aca | 4689 |
| Glu | Pro | Ile | His | Gly | Pro | Ser | Leu | Asp | Ala | Gln | Asn | Leu His Thr | |
| 1550 | | | | | 1555 | | | | 1560 | | | | |
| act | gtg | tgc | aac | atg | gtt | tac | aca | tgc | tat | atg | acc | tac ctc gac | 4734 |
| Thr | Val | Cys | Asn | Met | Val | Tyr | Thr | Cys | Tyr | Met | Thr | Tyr Leu Asp | |
| 1565 | | | | | 1570 | | | | 1575 | | | | |
| ctg | ttg | ttg | aat | gaa | gag | tta | gaa | gag | ttc | aca | ttt | ctc ttg tgt | 4779 |
| Leu | Leu | Leu | Asn | Glu | Glu | Leu | Glu | Glu | Phe | Thr | Phe | Leu Leu Cys | |
| 1580 | | | | | 1585 | | | | 1590 | | | | |
| gaa | agc | gac | gag | gat | gta | gta | ccg | gac | aga | ttc | gac | aac atc cag | 4824 |
| Glu | Ser | Asp | Glu | Asp | Val | Val | Pro | Asp | Arg | Phe | Asp | Asn Ile Gln | |
| 1595 | | | | | 1600 | | | | 1605 | | | | |
| gca | aaa | cac | tta | tgt | gtt | ctc | gca | gat | ttg | tac | tgt | caa cca ggg | 4869 |
| Ala | Lys | His | Leu | Cys | Val | Leu | Ala | Asp | Leu | Tyr | Cys | Gln Pro Gly | |
| 1610 | | | | | 1615 | | | | 1620 | | | | |
| acc | tgc | cca | cca | att | cga | ggt | cta | aga | ccg | gta | gag | aaa tgt gca | 4914 |
| Thr | Cys | Pro | Pro | Ile | Arg | Gly | Leu | Arg | Pro | Val | Glu | Lys Cys Ala | |
| 1625 | | | | | 1630 | | | | 1635 | | | | |
| gtt | cta | acc | gac | cat | atc | aag | gca | gag | gct | atg | tta | tct cca gca | 4959 |
| Val | Leu | Thr | Asp | His | Ile | Lys | Ala | Glu | Ala | Met | Leu | Ser Pro Ala | |
| 1640 | | | | | 1645 | | | | 1650 | | | | |
| gga | tct | tcg | tgg | aac | ata | aat | cca | att | att | gta | gac | cat tac tca | 5004 |
| Gly | Ser | Ser | Trp | Asn | Ile | Asn | Pro | Ile | Ile | Val | Asp | His Tyr Ser | |
| 1655 | | | | | 1660 | | | | 1665 | | | | |
| tgc | tct | ctg | act | tat | ctc | cgg | cga | gga | tcg | atc | aaa | cag ata aga | 5049 |
| Cys | Ser | Leu | Thr | Tyr | Leu | Arg | Arg | Gly | Ser | Ile | Lys | Gln Ile Arg | |
| 1670 | | | | | 1675 | | | | 1680 | | | | |

```
ttg aga gtt gat cca gga ttc att ttc gac gcc ctc gct gag gta          5094
Leu Arg Val Asp Pro Gly Phe Ile Phe Asp Ala Leu Ala Glu Val
    1685                1690                1695 aat gtc agt cag cca aag atc ggc agc aac aac atc tca aat atg          5139
Asn Val Ser Gln Pro Lys Ile Gly Ser Asn Asn Ile Ser Asn Met
1700                1705                1710 agc atc aag gct ttc aga ccc cca cac gat gat gtt gca aaa ttg          5184
Ser Ile Lys Ala Phe Arg Pro Pro His Asp Asp Val Ala Lys Leu
    1715                1720                1725 ctc aaa gat atc aac aca agc aag cac aat ctt ccc att tca ggg          5229
Leu Lys Asp Ile Asn Thr Ser Lys His Asn Leu Pro Ile Ser Gly
1730                1735                1740 ggc aat ctc gcc aat tat gaa atc cat gct ttc cgc aga atc ggg          5274
Gly Asn Leu Ala Asn Tyr Glu Ile His Ala Phe Arg Arg Ile Gly
    1745                1750                1755 ttg aac tca tct gct tgc tac aaa gct gtt gag ata tca aca tta          5319
Leu Asn Ser Ser Ala Cys Tyr Lys Ala Val Glu Ile Ser Thr Leu
1760                1765                1770 att agg aga tgc ctt gag cca ggg gag gac ggc ttg ttc ttg ggt          5364
Ile Arg Arg Cys Leu Glu Pro Gly Glu Asp Gly Leu Phe Leu Gly
    1775                1780                1785 gag gga tcg ggt tct atg ttg atc act tat aaa gag ata ctt aaa          5409
Glu Gly Ser Gly Ser Met Leu Ile Thr Tyr Lys Glu Ile Leu Lys
1790                1795                1800 cta aac aag tgc ttc tat aat agt ggg gtt tcc gcc aat tct aga          5454
Leu Asn Lys Cys Phe Tyr Asn Ser Gly Val Ser Ala Asn Ser Arg
    1805                1810                1815 tct ggt caa agg gaa tta gca ccc tat ccc tcc gaa gtt ggc ctt          5499
Ser Gly Gln Arg Glu Leu Ala Pro Tyr Pro Ser Glu Val Gly Leu
1820                1825                1830 gtc gaa cac aga atg gga gta ggt aat att gtc aaa gtg ctc ttt          5544
Val Glu His Arg Met Gly Val Gly Asn Ile Val Lys Val Leu Phe
    1835                1840                1845 aac ggg agg ccc gaa gtc acg tgg gta ggc agt gta gat tgc ttc          5589
Asn Gly Arg Pro Glu Val Thr Trp Val Gly Ser Val Asp Cys Phe
1850                1855                1860 aat ttc ata gtt agt aat atc cct acc tct agt gtg ggg ttt atc          5634
Asn Phe Ile Val Ser Asn Ile Pro Thr Ser Ser Val Gly Phe Ile
    1865                1870                1875 cat tca gat ata gag acc ttg cct gac aaa gat act ata gag aag          5679
His Ser Asp Ile Glu Thr Leu Pro Asp Lys Asp Thr Ile Glu Lys
1880                1885                1890 cta gag gaa ttg gca gcc atc tta tcg atg gct ctg ctc ctg ggc          5724
Leu Glu Glu Leu Ala Ala Ile Leu Ser Met Ala Leu Leu Leu Gly
    1895                1900                1905 aaa ata gga tca ata ctg gtg att aag ctt atg cct ttc agc ggg          5769
Lys Ile Gly Ser Ile Leu Val Ile Lys Leu Met Pro Phe Ser Gly
1910                1915                1920 gat ttt gtt cag gga ttt ata agt tat gta ggg tct cat tat aga          5814
Asp Phe Val Gln Gly Phe Ile Ser Tyr Val Gly Ser His Tyr Arg
    1925                1930                1935 gaa gtg aac ctt gta tac cct aga tac agc aac ttc atc tct act          5859
Glu Val Asn Leu Val Tyr Pro Arg Tyr Ser Asn Phe Ile Ser Thr
1940                1945                1950 gaa tct tat ttg gtt atg aca gat ctc aag gct aac cgg cta atg          5904
Glu Ser Tyr Leu Val Met Thr Asp Leu Lys Ala Asn Arg Leu Met
    1955                1960                1965 aat cct gaa aag att aag cag cag ata att gaa tca tct gtg agg          5949
Asn Pro Glu Lys Ile Lys Gln Gln Ile Ile Glu Ser Ser Val Arg
1970                1975                1980
```

```
act tca  cct gga ctt ata ggt  cac atc cta tcc att  aag caa cta      5994
Thr Ser  Pro Gly Leu Ile Gly  His Ile Leu Ser Ile  Lys Gln Leu
    1985                 1990                 1995 agc tgc  ata caa gca att gtg  gga gac gca gtt agt  aga ggt gat      6039
Ser Cys  Ile Gln Ala Ile Val  Gly Asp Ala Val Ser  Arg Gly Asp
    2000                 2005                 2010 atc aat  cct act ctg aaa aaa  ctt aca cct ata gag  cag gtg ctg      6084
Ile Asn  Pro Thr Leu Lys Lys  Leu Thr Pro Ile Glu  Gln Val Leu
    2015                 2020                 2025 atc aat  tgc ggg ttg gca att  aac gga cct aag ctg  tgc aaa gaa      6129
Ile Asn  Cys Gly Leu Ala Ile  Asn Gly Pro Lys Leu  Cys Lys Glu
    2030                 2035                 2040 ttg atc  cac cat gat gtt gcc  tca ggg caa gat gga  ttg ctt aat      6174
Leu Ile  His His Asp Val Ala  Ser Gly Gln Asp Gly  Leu Leu Asn
    2045                 2050                 2055 tct ata  ctc atc ctc tac agg  gag ttg gca aga ttc  aaa gac aac      6219
Ser Ile  Leu Ile Leu Tyr Arg  Glu Leu Ala Arg Phe  Lys Asp Asn
    2060                 2065                 2070 caa aga  agt caa caa ggg atg  ttc cac gct tac ccc  gta ttg gta      6264
Gln Arg  Ser Gln Gln Gly Met  Phe His Ala Tyr Pro  Val Leu Val
    2075                 2080                 2085 agt agc  agg caa cga gaa ctt  ata tct agg atc acc  cgc aaa ttc      6309
Ser Ser  Arg Gln Arg Glu Leu  Ile Ser Arg Ile Thr  Arg Lys Phe
    2090                 2095                 2100 tgg ggg  cac att ctt ctt tac  tcc ggg aac aaa aag  ttg ata aat      6354
Trp Gly  His Ile Leu Leu Tyr  Ser Gly Asn Lys Lys  Leu Ile Asn
    2105                 2110                 2115 aag ttt  atc cag aat ctc aag  tcc ggc tat ctg ata  cta gac tta      6399
Lys Phe  Ile Gln Asn Leu Lys  Ser Gly Tyr Leu Ile  Leu Asp Leu
    2120                 2125                 2130 cac cag  aat atc ttc gtt aag  aat cta tcc aag tca  gag aaa cag      6444
His Gln  Asn Ile Phe Val Lys  Asn Leu Ser Lys Ser  Glu Lys Gln
    2135                 2140                 2145 att att  atg acg ggg ggt ttg  aaa cgt gag tgg gtt  ttt aag gta      6489
Ile Ile  Met Thr Gly Gly Leu  Lys Arg Glu Trp Val  Phe Lys Val
    2150                 2155                 2160 aca gtc  aag gag acc aaa gaa  tgg tat aag tta gtc  gga tac agt      6534
Thr Val  Lys Glu Thr Lys Glu  Trp Tyr Lys Leu Val  Gly Tyr Ser
    2165                 2170                 2175 gcc ctg  att aag gac taa                                            6552
Ala Leu  Ile Lys Asp
    2180
```

<210> SEQ ID NO 17
<211> LENGTH: 2183
<212> TYPE: PRT
<213> ORGANISM: Measles virus

<400> SEQUENCE: 17

```
Met Asp Ser Leu Ser Val Asn Gln Ile Leu Tyr Pro Glu Val His Leu
1               5                   10                  15

Asp Ser Pro Ile Val Thr Asn Lys Ile Val Ala Ile Leu Glu Tyr Ala
            20                  25                  30

Arg Val Pro His Ala Tyr Ser Leu Glu Asp Pro Thr Leu Cys Gln Asn
        35                  40                  45

Ile Lys His Arg Leu Lys Asn Gly Phe Ser Asn Gln Met Ile Ile Asn
    50                  55                  60

Asn Val Glu Val Gly Asn Val Ile Lys Ser Lys Leu Arg Ser Tyr Pro
65                  70                  75                  80
```

```
Ala His Ser His Ile Pro Tyr Pro Asn Cys Asn Gln Asp Leu Phe Asn
                85                  90                  95
Ile Glu Asp Lys Glu Ser Thr Arg Lys Ile Arg Glu Leu Leu Lys Lys
            100                 105                 110
Gly Asn Ser Leu Tyr Ser Lys Val Ser Asp Lys Val Phe Gln Cys Leu
        115                 120                 125
Arg Asp Thr Asn Ser Arg Leu Gly Leu Gly Ser Glu Leu Arg Glu Asp
    130                 135                 140
Ile Lys Glu Lys Val Ile Asn Leu Gly Val Tyr Met His Ser Ser Gln
145                 150                 155                 160
Trp Phe Glu Pro Phe Leu Phe Trp Phe Thr Val Lys Thr Glu Met Arg
                165                 170                 175
Ser Val Ile Lys Ser Gln Thr His Thr Cys His Arg Arg His Thr
            180                 185                 190
Pro Val Phe Phe Thr Gly Ser Ser Val Glu Leu Leu Ile Ser Arg Asp
        195                 200                 205
Leu Val Ala Ile Ile Ser Lys Glu Ser Gln His Val Tyr Tyr Leu Thr
    210                 215                 220
Phe Glu Leu Val Leu Met Tyr Cys Asp Val Ile Glu Gly Arg Leu Met
225                 230                 235                 240
Thr Glu Thr Ala Met Thr Ile Asp Ala Arg Tyr Thr Glu Leu Leu Gly
                245                 250                 255
Arg Val Arg Tyr Met Trp Lys Leu Ile Asp Gly Phe Phe Pro Ala Leu
            260                 265                 270
Gly Asn Pro Thr Tyr Gln Ile Val Ala Met Leu Glu Pro Leu Ser Leu
        275                 280                 285
Ala Tyr Leu Gln Leu Arg Asp Ile Thr Val Glu Leu Arg Gly Ala Phe
    290                 295                 300
Leu Asn His Cys Phe Thr Glu Ile His Asp Val Leu Asp Gln Asn Gly
305                 310                 315                 320
Phe Ser Asp Glu Gly Thr Tyr His Glu Leu Thr Glu Ala Leu Asp Tyr
                325                 330                 335
Ile Phe Ile Thr Asp Asp Ile His Leu Thr Gly Glu Ile Phe Ser Phe
            340                 345                 350
Phe Arg Ser Phe Gly His Pro Arg Leu Glu Ala Val Thr Ala Ala Glu
        355                 360                 365
Asn Val Arg Lys Tyr Met Asn Gln Pro Lys Val Ile Val Tyr Glu Thr
    370                 375                 380
Leu Met Lys Gly His Ala Ile Phe Cys Gly Ile Ile Asn Gly Tyr
385                 390                 395                 400
Arg Asp Arg His Gly Gly Ser Trp Pro Pro Leu Thr Leu Pro Leu His
                405                 410                 415
Ala Ala Asp Thr Ile Arg Asn Ala Gln Ala Ser Gly Glu Gly Leu Thr
            420                 425                 430
His Glu Gln Cys Val Asp Asn Trp Lys Ser Phe Ala Gly Val Lys Phe
        435                 440                 445
Gly Cys Phe Met Pro Leu Ser Leu Asp Ser Asp Leu Thr Met Tyr Leu
    450                 455                 460
Lys Asp Lys Ala Leu Ala Ala Leu Gln Arg Glu Trp Asp Ser Val Tyr
465                 470                 475                 480
Pro Lys Glu Phe Leu Arg Tyr Asp Pro Pro Lys Gly Thr Gly Ser Arg
                485                 490                 495
Arg Leu Val Asp Val Phe Leu Asn Asp Ser Ser Phe Asp Pro Tyr Asp
            500                 505                 510
```

-continued

Val Ile Met Tyr Val Val Ser Gly Ala Tyr Leu His Asp Pro Glu Phe
            515                 520                 525

Asn Leu Ser Tyr Ser Leu Lys Glu Lys Glu Ile Lys Glu Thr Gly Arg
            530                 535                 540

Leu Phe Ala Lys Met Thr Tyr Lys Met Arg Ala Cys Gln Val Ile Ala
545                 550                 555                 560

Glu Asn Leu Ile Ser Asn Gly Ile Gly Lys Tyr Phe Lys Asp Asn Gly
            565                 570                 575

Met Ala Lys Asp Glu His Asp Leu Thr Lys Ala Leu His Thr Leu Ala
            580                 585                 590

Val Ser Gly Val Pro Lys Asp Leu Lys Glu Ser His Arg Gly Gly Pro
            595                 600                 605

Val Leu Lys Thr Tyr Ser Arg Ser Pro Val His Thr Ser Thr Arg Asn
            610                 615                 620

Val Arg Ala Ala Lys Gly Phe Ile Gly Phe Pro Gln Val Ile Arg Gln
625                 630                 635                 640

Asp Gln Asp Thr Asp His Pro Glu Asn Met Glu Ala Tyr Glu Thr Val
            645                 650                 655

Ser Ala Phe Ile Thr Thr Asp Leu Lys Lys Tyr Cys Leu Asn Trp Arg
            660                 665                 670

Tyr Glu Thr Ile Ser Leu Phe Ala Gln Arg Leu Asn Glu Ile Tyr Gly
            675                 680                 685

Leu Pro Ser Phe Phe Gln Trp Leu His Lys Arg Leu Glu Thr Ser Val
            690                 695                 700

Leu Tyr Val Ser Asp Pro His Cys Pro Pro Asp Leu Asp Ala His Ile
705                 710                 715                 720

Pro Leu Tyr Lys Val Pro Asn Asp Gln Ile Phe Ile Lys Tyr Pro Met
            725                 730                 735

Gly Gly Ile Glu Gly Tyr Cys Gln Lys Leu Trp Thr Ile Ser Thr Ile
            740                 745                 750

Pro Tyr Leu Tyr Leu Ala Ala Tyr Glu Ser Gly Val Arg Ile Ala Ser
            755                 760                 765

Leu Val Gln Gly Asp Asn Gln Thr Ile Ala Val Thr Lys Arg Val Pro
            770                 775                 780

Ser Thr Trp Pro Tyr Asn Leu Lys Lys Arg Glu Ala Ala Arg Val Thr
785                 790                 795                 800

Arg Asp Tyr Phe Val Ile Leu Arg Gln Arg Leu His Asp Ile Gly His
            805                 810                 815

His Leu Lys Ala Asn Glu Thr Ile Val Ser Ser His Phe Phe Val Tyr
            820                 825                 830

Ser Lys Gly Ile Tyr Tyr Asp Gly Leu Leu Val Ser Gln Ser Leu Lys
            835                 840                 845

Ser Ile Ala Arg Cys Val Phe Trp Ser Glu Thr Ile Val Asp Glu Thr
            850                 855                 860

Arg Ala Ala Cys Ser Asn Ile Ala Thr Thr Met Ala Lys Ser Ile Glu
865                 870                 875                 880

Arg Gly Tyr Asp Arg Tyr Leu Ala Tyr Ser Leu Asn Val Leu Lys Val
            885                 890                 895

Ile Gln Gln Ile Leu Ile Ser Leu Gly Phe Thr Ile Asn Ser Thr Met
            900                 905                 910

Thr Arg Asp Val Val Ile Pro Leu Leu Thr Asn Asn Asp Leu Leu Ile
            915                 920                 925

Arg Met Ala Leu Leu Pro Ala Pro Ile Gly Gly Met Asn Tyr Leu Asn

```
             930             935             940
Met Ser Arg Leu Phe Val Arg Asn Ile Gly Asp Pro Val Thr Ser Ser
945                 950             955                 960

Ile Ala Asp Leu Lys Arg Met Ile Leu Ala Ser Leu Met Pro Glu Glu
            965             970             975

Thr Leu His Gln Val Met Thr Gln Gln Pro Gly Asp Ser Ser Phe Leu
        980             985             990

Asp Trp Ala Ser Asp Pro Tyr Ser Ala Asn Leu Val Cys Val Gln Ser
    995             1000            1005

Ile Thr Arg Leu Leu Lys Asn Ile Thr Ala Arg Phe Val Leu Ile
    1010            1015            1020

His Ser Pro Asn Pro Met Leu Lys Gly Leu Phe His Asp Asp Ser
    1025            1030            1035

Lys Glu Asp Glu Gly Leu Ala Ala Phe Leu Met Asp Arg His
    1040            1045            1050

Ile Ile Val Pro Arg Ala Ala His Glu Ile Leu Asp His Ser Val
    1055            1060            1065

Thr Gly Ala Arg Glu Ser Ile Ala Gly Met Leu Asp Thr Thr Lys
    1070            1075            1080

Gly Leu Ile Arg Ala Ser Met Arg Lys Gly Gly Leu Thr Ser Arg
    1085            1090            1095

Val Ile Thr Arg Leu Ser Asn Tyr Asp Tyr Glu Gln Phe Arg Ala
    1100            1105            1110

Gly Met Val Leu Leu Thr Gly Arg Lys Arg Asn Val Leu Ile Asp
    1115            1120            1125

Lys Glu Ser Cys Ser Val Gln Leu Ala Arg Ala Leu Arg Ser His
    1130            1135            1140

Met Trp Ala Arg Leu Ala Arg Gly Arg Pro Ile Tyr Gly Leu Glu
    1145            1150            1155

Val Pro Asp Val Leu Glu Ser Met Arg Gly His Leu Ile Arg Arg
    1160            1165            1170

His Glu Thr Cys Val Ile Cys Glu Cys Gly Ser Val Asn Tyr Gly
    1175            1180            1185

Trp Phe Phe Val Pro Ser Gly Cys Gln Leu Asp Asp Ile Asp Lys
    1190            1195            1200

Glu Thr Ser Ser Leu Arg Val Pro Tyr Ile Gly Ser Thr Thr Asp
    1205            1210            1215

Glu Arg Thr Asp Met Lys Leu Ala Phe Val Arg Ala Pro Ser Arg
    1220            1225            1230

Ser Leu Arg Ser Ala Val Arg Ile Ala Thr Val Tyr Ser Trp Ala
    1235            1240            1245

Tyr Gly Asp Asp Asp Ser Ser Trp Asn Glu Ala Trp Leu Leu Ala
    1250            1255            1260

Arg Gln Arg Ala Asn Val Ser Leu Glu Glu Leu Arg Val Ile Thr
    1265            1270            1275

Pro Ile Ser Thr Ser Thr Asn Leu Ala His Arg Leu Arg Asp Arg
    1280            1285            1290

Ser Thr Gln Val Lys Tyr Ser Gly Thr Ser Leu Val Arg Val Ala
    1295            1300            1305

Arg Tyr Thr Thr Ile Ser Asn Asp Asn Leu Ser Phe Val Ile Ser
    1310            1315            1320

Asp Lys Lys Val Asp Thr Asn Phe Ile Tyr Gln Gln Gly Met Leu
    1325            1330            1335
```

```
Leu Gly Leu Gly Val Leu Glu Thr Leu Phe Arg Leu Glu Lys Asp
    1340            1345                1350

Thr Gly Ser Ser Asn Thr Val Leu His Leu His Val Glu Thr Asp
    1355            1360                1365

Cys Cys Val Ile Pro Met Ile Asp His Pro Arg Ile Pro Ser Ser
    1370            1375                1380

Arg Lys Leu Glu Leu Arg Ala Glu Leu Cys Thr Asn Pro Leu Ile
    1385            1390                1395

Tyr Asp Asn Ala Pro Leu Ile Asp Arg Asp Ala Thr Arg Leu Tyr
    1400            1405                1410

Thr Gln Ser His Arg Arg His Leu Val Glu Phe Val Thr Trp Ser
    1415            1420                1425

Thr Pro Gln Leu Tyr His Ile Leu Ala Lys Ser Thr Ala Leu Ser
    1430            1435                1440

Met Ile Asp Leu Val Thr Lys Phe Glu Lys Asp His Met Asn Glu
    1445            1450                1455

Ile Ser Ala Leu Ile Gly Asp Asp Ile Asn Ser Phe Ile Thr
    1460            1465                1470

Glu Phe Leu Leu Ile Glu Pro Arg Leu Phe Thr Ile Tyr Leu Gly
    1475            1480                1485

Gln Cys Ala Ala Ile Asn Trp Ala Phe Asp Val His Tyr His Arg
    1490            1495                1500

Pro Ser Gly Lys Tyr Gln Met Gly Glu Leu Leu Ser Ser Phe Leu
    1505            1510                1515

Ser Arg Met Ser Lys Gly Val Phe Lys Val Leu Val Asn Ala Leu
    1520            1525                1530

Ser His Pro Lys Ile Tyr Lys Lys Phe Trp His Cys Gly Ile Ile
    1535            1540                1545

Glu Pro Ile His Gly Pro Ser Leu Asp Ala Gln Asn Leu His Thr
    1550            1555                1560

Thr Val Cys Asn Met Val Tyr Thr Cys Tyr Met Thr Tyr Leu Asp
    1565            1570                1575

Leu Leu Leu Asn Glu Glu Leu Glu Glu Phe Thr Phe Leu Leu Cys
    1580            1585                1590

Glu Ser Asp Glu Asp Val Val Pro Asp Arg Phe Asp Asn Ile Gln
    1595            1600                1605

Ala Lys His Leu Cys Val Leu Ala Asp Leu Tyr Cys Gln Pro Gly
    1610            1615                1620

Thr Cys Pro Pro Ile Arg Gly Leu Arg Pro Val Glu Lys Cys Ala
    1625            1630                1635

Val Leu Thr Asp His Ile Lys Ala Glu Ala Met Leu Ser Pro Ala
    1640            1645                1650

Gly Ser Ser Trp Asn Ile Asn Pro Ile Ile Val Asp His Tyr Ser
    1655            1660                1665

Cys Ser Leu Thr Tyr Leu Arg Arg Gly Ser Ile Lys Gln Ile Arg
    1670            1675                1680

Leu Arg Val Asp Pro Gly Phe Ile Phe Asp Ala Leu Ala Glu Val
    1685            1690                1695

Asn Val Ser Gln Pro Lys Ile Gly Ser Asn Asn Ile Ser Asn Met
    1700            1705                1710

Ser Ile Lys Ala Phe Arg Pro Pro His Asp Asp Val Ala Lys Leu
    1715            1720                1725

Leu Lys Asp Ile Asn Thr Ser Lys His Asn Leu Pro Ile Ser Gly
    1730            1735                1740
```

-continued

Gly Asn Leu Ala Asn Tyr Glu Ile His Ala Phe Arg Arg Ile Gly
    1745                1750                1755

Leu Asn Ser Ser Ala Cys Tyr Lys Ala Val Glu Ile Ser Thr Leu
    1760                1765                1770

Ile Arg Arg Cys Leu Glu Pro Gly Glu Asp Gly Leu Phe Leu Gly
    1775                1780                1785

Glu Gly Ser Gly Ser Met Leu Ile Thr Tyr Lys Glu Ile Leu Lys
    1790                1795                1800

Leu Asn Lys Cys Phe Tyr Asn Ser Gly Val Ser Ala Asn Ser Arg
    1805                1810                1815

Ser Gly Gln Arg Glu Leu Ala Pro Tyr Pro Ser Glu Val Gly Leu
    1820                1825                1830

Val Glu His Arg Met Gly Val Gly Asn Ile Val Lys Val Leu Phe
    1835                1840                1845

Asn Gly Arg Pro Glu Val Thr Trp Val Gly Ser Val Asp Cys Phe
    1850                1855                1860

Asn Phe Ile Val Ser Asn Ile Pro Thr Ser Ser Val Gly Phe Ile
    1865                1870                1875

His Ser Asp Ile Glu Thr Leu Pro Asp Lys Asp Thr Ile Glu Lys
    1880                1885                1890

Leu Glu Glu Leu Ala Ala Ile Leu Ser Met Ala Leu Leu Leu Gly
    1895                1900                1905

Lys Ile Gly Ser Ile Leu Val Ile Lys Leu Met Pro Phe Ser Gly
    1910                1915                1920

Asp Phe Val Gln Gly Phe Ile Ser Tyr Val Gly Ser His Tyr Arg
    1925                1930                1935

Glu Val Asn Leu Val Tyr Pro Arg Tyr Ser Asn Phe Ile Ser Thr
    1940                1945                1950

Glu Ser Tyr Leu Val Met Thr Asp Leu Lys Ala Asn Arg Leu Met
    1955                1960                1965

Asn Pro Glu Lys Ile Lys Gln Gln Ile Ile Glu Ser Ser Val Arg
    1970                1975                1980

Thr Ser Pro Gly Leu Ile Gly His Ile Leu Ser Ile Lys Gln Leu
    1985                1990                1995

Ser Cys Ile Gln Ala Ile Val Gly Asp Ala Val Ser Arg Gly Asp
    2000                2005                2010

Ile Asn Pro Thr Leu Lys Lys Leu Thr Pro Ile Glu Gln Val Leu
    2015                2020                2025

Ile Asn Cys Gly Leu Ala Ile Asn Gly Pro Lys Leu Cys Lys Glu
    2030                2035                2040

Leu Ile His His Asp Val Ala Ser Gly Gln Asp Gly Leu Leu Asn
    2045                2050                2055

Ser Ile Leu Ile Leu Tyr Arg Glu Leu Ala Arg Phe Lys Asp Asn
    2060                2065                2070

Gln Arg Ser Gln Gln Gly Met Phe His Ala Tyr Pro Val Leu Val
    2075                2080                2085

Ser Ser Arg Gln Arg Glu Leu Ile Ser Arg Ile Thr Arg Lys Phe
    2090                2095                2100

Trp Gly His Ile Leu Leu Tyr Ser Gly Asn Lys Lys Leu Ile Asn
    2105                2110                2115

Lys Phe Ile Gln Asn Leu Lys Ser Gly Tyr Leu Ile Leu Asp Leu
    2120                2125                2130

His Gln Asn Ile Phe Val Lys Asn Leu Ser Lys Ser Glu Lys Gln

Ile Ile Met Thr Gly Gly Leu Lys Arg Glu Trp Val Phe Lys Val
2150                    2155                    2160

Thr Val Lys Glu Thr Lys Glu Trp Tyr Lys Leu Val Gly Tyr Ser
2165                    2170                    2175

Ala Leu Ile Lys Asp
2180

<210> SEQ ID NO 18
<211> LENGTH: 18967
<212> TYPE: DNA
<213> ORGANISM: Artificial
<220> FEATURE:
<223> OTHER INFORMATION: pTM-MVSchw plasmid

<400> SEQUENCE: 18

| | | |
|---|---|---|
| gcggccgcta atacgactca ctatagggcc aactttgttt ggtctgatga gtccgtgagg | 60 |
| acgaaacccg gagtcccggg tcaccaaaca agttgggta aggatagttc aatcaatgat | 120 |
| catcttctag tgcacttagg attcaagatc ctattatcag gacaagagc aggattaggg | 180 |
| atatccgaga tggccacact tttaaggagc ttagcattgt tcaaaagaaa caaggacaaa | 240 |
| ccacccatta catcaggatc cggtggagcc atcagaggaa tcaaacacat tattatagta | 300 |
| ccaatccctg gagattcctc aattaccact cgatccagac ttctggaccg ttggtgagg | 360 |
| ttaattggaa acccggatgt gagcgggccc aaactaacag gggcactaat aggtatatta | 420 |
| tccttatttg tggagtctcc aggtcaattg attcagagga tcaccgatga ccctgacgtt | 480 |
| agcataaggc tgttagaggt tgtccagagt gaccagtcac aatctggcct taccttcgca | 540 |
| tcaagaggta ccaacatgga ggatgaggcg gaccaatact tttcacatga tgatccaatt | 600 |
| agtagtgatc aatccaggtt cggatggttc gggaacaagg aaatctcaga tattgaagtg | 660 |
| caagaccctg agggattcaa catgattctg ggtaccatcc tagcccaaat ttgggtcttg | 720 |
| ctcgcaaagg cggttacggc cccagacacg gcagctgatt cggagctaag aaggtggata | 780 |
| aagtacaccc aacaaagaag ggtagttggt gaatttagat tggagagaaa atggttggat | 840 |
| gtggtgagga acaggattgc cgaggacctc ccttacgcc gattcatggt cgctctaatc | 900 |
| ctggatatca agaacacc cggaaacaaa cccaggattg ctgaaatgat atgtgacatt | 960 |
| gatacatata tcgtagaggc aggattagcc agttttatcc tgactattaa gtttgggata | 1020 |
| gaaactatgt atcctgctct tggactgcat gaatttgctg tgagttatc cacacttgag | 1080 |
| tccttgatga acctttacca gcaaatgggg gaaactgcac cctacatggt aatcctggag | 1140 |
| aactcaattc agaacaagtt cagtgcagga tcatacccc tgctctggag ctatgccatg | 1200 |
| ggagtaggag tggaacttga aaactccatg ggaggtttga ctttggccg atcttacttt | 1260 |
| gatccagcat attttagatt agggcaagag atggtaagga ggtcagctgg aaaggtcagt | 1320 |
| tccacattgg catctgaact cggtatcact gccgaggatg caaggcttgt tcagagatt | 1380 |
| gcaatgcata ctactgagga caagatcagt agagcggttg gacccagaca agcccaagta | 1440 |
| tcatttctac acggtgatca aagtgagaat gagctaccga gattgggggg caaggaagat | 1500 |
| aggagggtca aacagagtcg aggagaagcc agggagagct acagagaaac cgggccagc | 1560 |
| agagcaagtg atgcgagagc tgcccatctt ccaaccggca caccctaga cattgacact | 1620 |
| gcaacggagt ccagccaaga tccgcaggac agtcgaaggt cagctgacgc cctgcttagg | 1680 |
| ctgcaagcca tggcaggaat ctcggaagaa caaggctcag acacgacac ccctatagtg | 1740 |
| tacaatgaca gaaatcttct agactaggtg cgagaggccg agggccagaa caacatccgc | 1800 |

```
ctaccatcca tcattgttat aaaaaactta ggaaccaggt ccacacagcc gccagcccat    1860
caaccatcca ctcccacgat tggagccaat ggcagaagag caggcacgcc atgtcaaaaa    1920
cggactggaa tgcatccggg ctctcaaggc cgagcccatc ggctcactgg ccatcgagga    1980
agctatggca gcatggtcag aaatatcaga caacccagga caggagcgag ccacctgcag    2040
ggaagagaag gcaggcagtt cgggtctcag caaaccatgc ctctcagcaa ttggatcaac    2100
tgaaggcggt gcacctcgca tccgcggtca gggacctgga gagagcgatg acgacgctga    2160
aactttggga atccccccaa gaaatctcca ggcatcaagc actgggttac agtgttatta    2220
cgtttatgat cacagcggtg aagcggttaa gggaatccaa gatgctgact ctatcatggt    2280
tcaatcaggc cttgatggtg atagcaccct ctcaggagga acaatgaat ctgaaaacag    2340 cgatgtggat attggcgaac ctgataccga gggatatgct atcactgacc ggggatctgc    2400
tcccatctct atggggttca ggcttctga tgttgaaact gcagaaggag gggagatcca    2460
cgagctcctg agactccaat ccagaggcaa caactttccg aagcttggga aaactctcaa    2520
tgttcctccg cccccggacc ccggtagggc cagcacttcc gggacaccca ttaaaaaggg    2580
cacagacgcg agattagcct catttggaac ggagatcgcg tctttattga caggtggtgc    2640
aacccaatgt gctcgaaagt caccctcgga accatcaggg ccaggtgcac ctgcggggaa    2700
tgtccccgag tgtgtgagca atgccgcact gatacaggag tggacacccg aatctggtac    2760
cacaatctcc ccgagatccc agaataatga agaaggggga gactattatg atgatgagct    2820
gttctctgat gtccaagata ttaaaacagc cttggccaaa atacacgagg ataatcagaa    2880
gataatctcc aagctagaat cactgctgtt attgaaggga gaagttgagt caattaagaa    2940
gcagatcaac aggcaaaata tcagcatatc caccctggaa ggacacctct caagcatcat    3000
gatcgccatt cctggacttg ggaaggatcc caacgacccc actgcagatg tcgaaatcaa    3060
tcccgacttg aaacccatca taggcagaga ttcaggccga gcactggccg aagttctcaa    3120
gaaacccgtt gccagccgac aactccaagg aatgacaaat ggacggacca gttccagagg    3180
acagctgctg aaggaatttc agctaaagcc gatcgggaaa aagatgagct cagccgtcgg    3240
gtttgttcct gacaccggcc ctgcatcacg cagtgtaatc cgctccatta taaaatccag    3300
ccggctagag gaggatcgga agcgttacct gatgactctc cttgatgata tcaaaggagc    3360
caatgatctt gccaagttcc accagatgct gatgaagata ataatgaagt agctacagct    3420
caacttacct gccaacccca tgccagtcga cccaactagt acaacctaaa tccattataa    3480
aaaacttagg agcaaagtga ttgcctccca aggtccacaa tgacagagac ctacgacttc    3540
gacaagtcgg catgggacat caaagggtcg atcgctccga tacaacccac cacctacagt    3600
gatggcaggc tggtgcccca ggtcagagtc atagatcctg gtctaggcga caggaaggat    3660
gaatgcttta tgtacatgtt tctgctgggg gttgttgagg acagcgattc cctagggcct    3720
ccaatcgggc gagcatttgg gttcctgccc ttaggtgttg gcagatccac agcaaagccc    3780
gaaaaactcc tcaaagaggc cactgagctt gacatagttg ttagacgtac agcagggctc    3840
aatgaaaaac tggtgttcta caacaacacc ccactaactc tcctcacacc ttggagaaag    3900
gtcctaacaa cagggagtgt cttcaacgca accaagtgt gcaatgcggt taatctgata    3960
ccgctcgata ccccgcagag gttccgtgtt gtttatatga gcatcacccg tctttcggat    4020
aacgggtatt acaccgttcc tagaagaatg ctggaattca gatcggtcaa tgcagtggcc    4080
ttcaacctgc tggtgaccct taggattgac aaggcgatag gccctgggaa gatcatcgac    4140
aatacagagc aacttcctga ggcaacattt atggtccaca tcgggaactt caggagaaag    4200
```

```
aagagtgaag tctactctgc cgattattgc aaaatgaaaa tcgaaaagat gggcctggtt    4260
tttgcacttg gtgggatagg gggcaccagt cttcacatta gaagcacagg caaaatgagc    4320
aagactctcc atgcacaact cgggttcaag aagaccttat gttacccgct gatggatatc    4380
aatgaagacc ttaatcgatt actctggagg agcagatgca agatagtaag aatccaggca    4440
gttttgcagc catcagttcc tcaagaattc cgcatttacg acgacgtgat cataaatgat    4500
gaccaaggac tattcaaagt tctgtagacc gtagtgccca gcaatgcccg aaaacgaccc    4560
ccctcacaat gacagccaga aggcccggac aaaaaagccc cctccgaaag actccacgga    4620
ccaagcgaga ggccagccag cagccgacgg caagcgcgaa caccaggcgg ccccagcaca    4680
gaacagccct gacacaaggc caccaccagc caccccaatc tgcatcctcc tcgtgggacc    4740
cccgaggacc aaccccccaag gctgcccccg atccaaacca ccaaccgcat ccccaccacc    4800
cccgggaaag aaaccccccag caattggaag gcccctcccc ctcttcctca acacaagaac    4860
tccacaaccg aaccgcacaa gcgaccgagg tgacccaacc gcaggcatcc gactccctag    4920
acagatcctc tctccccggc aaactaaaca aaacttaggg ccaaggaaca tacacaccca    4980
acagaaccca gaccccggcc cacggcgccg cgccccccaac cccgacaac cagagggagc    5040 ccccaaccaa tcccgccggc tcccccggtg cccacaggca gggacaccaa ccccgaaca    5100 gacccagcac ccaaccatcg acaatccaag acgggggggc cccccaaaa aaggccccc    5160 aggggccgac agccagcacc gcgaggaagc ccacccaccc cacacacgac cacggcaacc    5220
aaaccagaac ccagaccacc ctgggccacc agctcccaga ctcggccatc accccgcaga    5280
aaggaaaggc cacaacccgc gcaccccagc cccgatccgg cggggagcca cccaacccga    5340
accagcaccc aagagcgatc cccgaaggac ccccgaaccg caaaggacat cagtatccca    5400
cagcctctcc aagtcccccg gtctcctcct cttctcgaag ggaccaaaag atcaatccac    5460
cacacccgac gacactcaac tccccacccc taaaggagac accgggaatc ccagaatcaa    5520
gactcatcca atgtccatca tgggtctcaa ggtgaacgtc tctgccatat tcatggcagt    5580
actgttaact ctccaaacac ccaccggtca aatccattgg ggcaatctct ctaagatagg    5640
ggtggtagga ataggaagtg caagctacaa agttatgact cgttccagcc atcaatcatt    5700
agtcataaaa ttaatgccca atataactct cctcaataac tgcacgaggg tagagattgc    5760
agaatacagg agactactga gaacagtttt ggaaccaatt agagatgcac ttaatgcaat    5820
gacccagaat ataagaccgg ttcagagtgt agcttcaagt aggagacaca agagatttgc    5880
gggagtagtc ctggcaggtg cggccctagg cgttgccaca gctgctcaga taacagccgg    5940
cattgcactt caccagtcca tgctgaactc tcaagccatc gacaatctga gagcgagcct    6000
ggaaactact aatcaggcaa ttgagacaat cagacaagca gggcaggaga tgatattggc    6060
tgttcagggt gtccaagact acatcaataa tgagctgata ccgtctatga accaactatc    6120
ttgtgattta atcggccaga agctcgggct caaattgctc agatactata cagaaatcct    6180
gtcattattt ggccccagtt tacgggaccc catatctgcg gagatatcta tccaggcttt    6240
gagctatgcg cttggaggag acatcaataa ggtgttagaa aagctcggat acagtggagg    6300
tgatttactg ggcatcttag agagcggagg aataaaggcc cggataactc acgtcgacac    6360
agagtcctac ttcattgtcc tcagtatagc ctatccgacg ctgtccgaga ttaagggggt    6420
gattgtccac cggctagagg gggtctcgta aacataggc tctcaagagt ggtataccac    6480
tgtgcccaag tatgttgcaa cccaagggta ccttatctcg aattttgatg agtcatcgtg    6540
tactttcatg ccagaggggga ctgtgtgcag ccaaaatgcc ttgtacccga tgagtcctct    6600
```

```
gctccaagaa tgcctccggg ggtacaccaa gtcctgtgct cgtacactcg tatccgggtc   6660
ttttgggaac cggttcattt tatcacaagg gaacctaata gccaattgtg catcaatcct   6720
ttgcaagtgt tacacaacag gaacgatcat taatcaagac cctgacaaga tcctaacata   6780
cattgctgcc gatcactgcc cggtagtcga ggtgaacggc gtgaccatcc aagtcgggag   6840
caggaggtat ccagacgctg tgtacttgca cagaattgac ctcggtcctc ccatatcatt   6900
ggagaggttg gacgtaggga caaatctggg gaatgcaatt gctaagttgg aggatgccaa   6960
ggaattgttg gagtcatcgg accagatatt gaggagtatg aaaggtttat cgagcactag   7020
catagtctac atcctgattg cagtgtgtct tggagggttg atagggatcc ccgctttaat   7080
atgttgctgc aggggcgtt gtaacaaaaa gggagaacaa gttggtatgt caagaccagg   7140
cctaaagcct gatcttacgg gaacatcaaa atcctatgta aggtcgctct gatcctctac   7200
aactcttgaa acacaaatgt cccacaagtc tcctcttcgt catcaagcaa ccaccgcacc   7260
cagcatcaag cccacctgaa attatctccg gcttccctct ggccgaacaa tatcggtagt   7320
taatcaaaac ttagggtgca agatcatcca caatgtcacc acaacgagac cggataaatg   7380
ccttctacaa agataacccc catcccaagg gaagtaggat agtcattaac agagaacatc   7440
ttatgattga tagaccttat gttttgctgg ctgttctgtt tgtcatgttt ctgagcttga   7500
tcgggttgct agccattgca ggcattagac ttcatcgggc agccatctac accgcagaga   7560
tccataaaag cctcagcacc aatctagatg taactaactc aatcgagcat caggtcaagg   7620
acgtgctgac accactcttc aaaatcatcg gtgatgaagt gggcctgagg acacctcaga   7680
gattcactga cctagtgaaa ttaatctctg acaagattaa attccttaat ccggataggg   7740
agtacgactt cagagatctc acttggtgta tcaacccgcc agagagaatc aaattggatt   7800
atgatcaata ctgtgcagat gtggctgctg aagagctcat gaatgcattg gtgaactcaa   7860
ctctactgga gaccagaaca accaatcagt tcctagctgt ctcaaaggga aactgctcag   7920
ggcccactac aatcagaggt caattctcaa acatgtcgct gtccctgtta gacttgtatt   7980
taggtcgagg ttacaatgtg tcatctatag tcactatgac atcccaggga atgtatgggg   8040
gaacttacct agtggaaaag cctaatctga gcagcaaaag gtcagagttg tcacaactga   8100
gcatgtaccg agtgttgaa gtaggtgtta tcagaaatcc gggtttgggg gctccggtgt   8160
tccatatgac aaactatctt gagcaaccag tcagtaatga tctcagcaac tgtatggtgg   8220
ctttggggga gctcaaactc gcagcccttt gtcacgggga agattctatc acaattccct   8280
atcagggatc agggaaaggt gtcagcttcc agctcgtcaa gctaggtgtc tggaaatccc   8340
caaccgacat gcaatcctgg gtccccttat caacgatga tccagtgata gacaggcttt   8400
acctctcatc tcacagaggt gttatcgctg acaatcaagc aaaatgggct gtcccgacaa   8460
cacgaacaga tgacaagttg cgaatggaga catgcttcca acaggcgtgt aagggtaaaa   8520
tccaagcact ctgcgagaat cccgagtggg caccattgaa ggataacagg attccttcat   8580
acggggtctt gtctgttgat ctgagtctga cagttgagct taaaatcaaa attgcttcgg   8640
gattcgggcc attgatcaca cacggttcag ggatggacct atacaaatcc aaccacaaca   8700
atgtgtattg gctgactatc ccgccaatga gaaacctagc cttaggtgta atcaacacat   8760
tggagtggat accgagattc aaggttagtc cctacctctt cactgtccca attaaggaag   8820
caggcgaaga ctgccatgcc ccaacatacc tacctgcgga ggtggatggt gatgtcaaac   8880
tcagttccaa tctggtgatt ctacctggtc aagatctcca atatgttttg gcaacctacg   8940
atacttccag ggttgaacat gctgtggttt attacgttta cagcccaagc cgctcattt   9000
```

```
cttactttta tccttttagg ttgcctataa aggggtccc catcgaatta caagtggaat    9060
gcttcacatg ggaccaaaaa ctctggtgcc gtcacttctg tgtgcttgcg gactcagaat    9120
ctggtggaca tatcactcac tctgggatgg tgggcatggg agtcagctgc acagtcaccc    9180
gggaagatgg aaccaatcgc agatagggct gctagtgaac caatcacatg atgtcaccca    9240
gacatcaggc ataccacta gtgtgaaata gacatcagaa ttaagaaaaa cgtagggtcc    9300
aagtggttcc ccgttatgga ctcgctatct gtcaaccaga tcttataccc tgaagttcac    9360
ctagatagcc cgatagttac caataagata gtagccatcc tggagtatgc tcgagtccct    9420
cacgcttaca gcctggagga ccctacactg tgtcagaaca tcaagcaccg cctaaaaaac    9480
ggattttcca accaaatgat tataaacaat gtggaagttg gaatgtcat caagtccaag    9540
cttaggagtt atccggccca ctctcatatt ccatatccaa attgtaatca ggatttattt    9600
aacatagaag acaaagagtc aacgaggaag atccgtgaac tcctcaaaaa ggggaattcg    9660
ctgtactcca aagtcagtga taaggttttc caatgcttaa gggacactaa ctcacggctt    9720
ggcctaggct ccgaattgag ggaggacatc aaggagaaag ttattaactt gggagtttac    9780
atgcacagct cccagtggtt tgagcccttt ctgttttggt ttacagtcaa gactgagatg    9840
aggtcagtga ttaaatcaca aacccatact tgccatagga ggagacacac acctgtattc    9900
ttcactggta gttcagttga gttgctaatc tctcgtgacc ttgttgctat aatcagtaaa    9960
gagtctcaac atgtatatta cctgacattt gaactggttt tgatgtattg tgatgtcata    10020
gaggggaggt taatgacaga gaccgctatg actattgatg ctaggtatac agagcttcta    10080
ggaagagtca gatacatgtg gaaactgata gatggtttct tccctgcact cgggaatcca    10140
acttatcaaa ttgtagccat gctggagcct ctttcacttg cttacctgca gctgagggat    10200
ataacagtag aactcagagg tgcttttcctt aaccactgct ttactgaaat acatgatgtt    10260
cttgaccaaa acgggttttc tgatgaaggt acttatcatg agttaactga agctctagat    10320
tacattttca taactgatga catacatctg acaggggaga ttttctcatt tttcagaagt    10380
ttcggccacc ccagacttga agcagtaacg gctgctgaaa atgttaggaa atacatgaat    10440
cagcctaaag tcattgtgta tgagactctg atgaaaggtc atgccatatt ttgtggaatc    10500
ataatcaacg gctatcgtga caggcacgga ggcagttggc accgctgac cctccccctg    10560
catgctgcag acacaatccg gaatgctcaa gcttcaggtg aagggttaac acatgagcag    10620
tgcgttgata actggaaatc ttttgctgga gtgaaatttg gctgctttat gcctcttagc    10680
ctggatagtg atctgacaat gtacctaaag gacaaggcac ttgctgctct ccaaagggaa    10740
tgggattcag tttacccgaa agagttcctg cgttacgacc ctcccaaggg aaccgggtca    10800
cggaggcttg tagatgtttt ccttaatgat tcgagctttg acccatatga tgtgataatg    10860
tatgttgtaa gtggagctta cctccatgac cctgagttca acctgtctta cagcctgaaa    10920
gaaaaggaga tcaaggaaac aggtagactt tttgctaaaa tgacttacaa aatgagggca    10980
tgccaagtga ttgctgaaaa tctaatctca aacggattg gcaaatattt taaggacaat    11040
gggatggcca aggatgagca cgatttgact aaggcactcc acactctagc tgtctcagga    11100
gtccccaaag atctcaagaa aagtcacagg gggggccag tcttaaaaac ctactcccga    11160
agcccagtcc acacaagtac caggaacgtg agagcagcaa aagggtttat agggttccct    11220
caagtaattc ggcaggacca agacactgat catccggaga atatggaagc ttacgagaca    11280
gtcagtgcat ttatcacgac tgatctcaag aagtactgcc ttaattggag atatgagacc    11340
atcagcttgt ttgcacagag gctaaatgag atttacggat tgcctcatt tttccagtgg    11400
```

```
ctgcataaga ggcttgagac ctctgtcctg tatgtaagtg accctcattg ccccccgac      11460
cttgacgccc atatcccgtt atataaagtc cccaatgatc aaatcttcat taagtaccct      11520
atgggaggta tagaagggta ttgtcagaag ctgtggacca tcagcaccat tccctatcta      11580
tacctggctg cttatgagag cggagtaagg attgcttcgt tagtgcaagg ggacaatcag      11640
accatagccg taacaaaaag ggtacccagc acatggccct acaaccttaa gaaacgggaa      11700
gctgctagag taactagaga ttactttgta attcttaggc aaaggctaca tgatattggc      11760
catcacctca aggcaaatga gacaattgtt tcatcacatt tttttgtcta ttcaaaagga      11820
atatattatg atgggctact tgtgtcccaa tcactcaaga gcatcgcaag atgtgtattc      11880
tggtcagaga ctatagttga tgaaacaagg gcagcatgca gtaatattgc tacaacaatg      11940
gctaaaagca tcgagagagg ttatgaccgt taccttgcat attccctgaa cgtcctaaaa      12000
gtgatacagc aaattctgat ctctcttggc ttcacaatca attcaaccat gacccgggat      12060
gtagtcatac ccctcctcac aaacaacgac ctcttaataa ggatggcact gttgcccgct      12120
cctattgggg ggatgaatta tctgaatatg agcaggctgt ttgtcagaaa catcggtgat      12180
ccagtaacat catcaattgc tgatctcaag agaatgattc tcgcctcact aatgcctgaa      12240
gagaccctcc atcaagtaat gacacaacaa ccggggact cttcattcct agactgggct      12300
agcgacccct actcagcaaa tcttgtatgt gtccagagca tcactagact cctcaagaac      12360
ataactgcaa ggtttgtcct gatccatagt ccaaacccaa tgttaaaagg attattccat      12420
gatgacagta aagaagagga cgagggactg gcggcattcc tcatggacag gcatattata      12480
gtacctaggg cagctcatga aatcctggat catagtgtca caggggcaag agagtctatt      12540
gcaggcatgc tggataccac aaaaggcttg attcgagcca gcatgaggaa gggggggtta      12600
acctctcgag tgataaccag attgtccaat tatgactatg aacaattcag agcagggatg      12660
gtgctattga caggaagaaa gagaaatgtc ctcattgaca aagagtcatg ttcagtgcag      12720
ctggcgagag ctctaagaag ccatatgtgg gcgaggctag ctcgaggacg gcctatttac      12780
ggccttgagg tccctgatgt actagaatct atgcgaggcc accttattcg gcgtcatgag      12840
acatgtgtca tctgcgagtg tggatcagtc aactacggat ggttttttgt cccctcgggt      12900
tgccaactgg atgatattga caaggaaaca tcatccttga gagtcccata tattggttct      12960
accactgatg agagaacaga catgaagctt gccttcgtaa gagccccaag tcgatccttg      13020
cgatctgctg ttagaatagc aacagtgtac tcatgggctt acggtgatga tgatagctct      13080
tggaacgaag cctggttgtt ggctaggcaa agggccaatg tgagcctgga ggagctaagg      13140
gtgatcactc ccatctcaac ttcgactaat ttagcgcata ggttgaggga tcgtagcact      13200
caagtgaaat actcaggtac atcccttgtc cgagtggcga ggtataccac aatctccaac      13260
gacaatctct catttgtcat atcagataag aaggttgata ctaactttat ataccaacaa      13320
ggaatgcttc tagggttggg tgttttagaa acattgtttc gactcgagaa agataccgga      13380
tcatctaaca cggtattaca tcttcacgtc gaaacagatt gttgcgtgat cccgatgata      13440
gatcatccca ggatacccag ctcccgcaag ctagagctga gggcagagct atgtaccaac      13500
ccattgatat atgataatgc acctttaatt gacagagatg caacaaggct atacacccag      13560
agccatagga ggcaccttgt ggaatttgtt acatggtcca cccccaact atatcacatt      13620
ttagctaagt ccacagcact atctatgatt gacctggtaa caaaatttga gaaggaccat      13680
atgaatgaaa tttcagctct cataggggat gacgatatca atagtttcat aactgagttt      13740
ctgctcatag agccaagatt attcactatc tacttgggcc agtgtgcggc catcaattgg      13800
```

```
gcatttgatg tacattatca tagaccatca gggaaatatc agatgggtga gctgttgtca   13860 tcgttcctttt ctagaatgag caaaggagtg tttaaggtgc ttgtcaatgc tctaagccac   13920
ccaaagatct acaagaaatt ctggcattgt ggtattatag agcctatcca tggtccttca   13980
cttgatgctc aaaacttgca cacaactgtg tgcaacatgg tttacacatg ctatatgacc   14040
tacctcgacc tgttgttgaa tgaagagtta aagagttca catttctctt gtgtgaaagc   14100
gacgaggatg tagtaccgga cagattcgac aacatccagg caaaacactt atgtgttctg   14160
gcagatttgt actgtcaacc agggacctgc ccaccaattc gaggtctaag accggtagag   14220
aaatgtgcag ttctaaccga ccatatcaag gcagaggcta tgttatctcc agcaggatct   14280
tcgtggaaca taaatccaat tattgtagac cattactcat gctctctgac ttatctccgg   14340
cgaggatcga tcaaacagat aagattgaga gttgatccag gattcatttt cgacgccctc   14400
gctgaggtaa atgtcagtca gccaaagatc ggcagcaaca acatctcaaa tatgagcatc   14460
aaggctttca gaccccaca cgatgatgtt gcaaaattgc tcaaagatat caacacaagc   14520
aagcacaatc ttcccatttc aggggggcaat ctcgccaatt atgaaatcca tgctttccgc   14580
agaatcgggt tgaactcatc tgcttgctac aaagctgttg agatatcaac attaattagg   14640
agatgccttg agccaggga ggacggcttg ttcttgggtg agggatcggg ttctatgttg   14700
atcacttata aagagatact taaactaaac aagtgcttct ataatagtgg ggtttccgcc   14760
aattctagat ctggtcaaag ggaattagca ccctatccct ccgaagttgg ccttgtcgaa   14820
cacagaatgg gagtaggtaa tattgtcaaa gtgctcttta acgggaggcc cgaagtcacg   14880
tgggtaggca gtgtagattg cttcaatttc atagttagta atatccctac ctctagtgtg   14940
gggtttatcc attcagatat agagaccttg cctgacaaag atactataga gaagctagag   15000
gaattggcag ccatcttatc gatggctctg ctcctgggca aaataggatc aatactggtg   15060
attaagctta tgccttttcag cggggatttt gttcagggat ttataagtta tgtagggtct   15120
cattatagag aagtgaacct tgtataccct agatacagca acttcatctc tactgaatct   15180
tatttggtta tgacagatct caaggctaac cggctaatga atcctgaaaa gattaagcag   15240
cagataattg aatcatctgt gaggacttca cctggactta taggtcacat cctatccatt   15300
aagcaactaa gctgcataca agcaattgtg ggagacgcag ttagtagagg tgatatcaat   15360
cctactctga aaaacttac acctatagag caggtgctga tcaattgcgg gttggcaatt   15420
aacggaccta agctgtgcaa agaattgatc caccatgatg ttgcctcagg gcaagatgga   15480
ttgcttaatt ctatactcat cctctacagg gagttggcaa gattcaaaga caaccaaaga   15540
agtcaacaag ggatgttcca cgcttacccc gtattggtaa gtagcaggca acgagaactt   15600
atatctagga tcacccgcaa attctggggg cacattcttc tttactccgg gaacaaaaag   15660
ttgataaata gtttatcca gaatctcaag tccggctatc tgatactaga cttacaccag   15720
aatatcttcg ttaagaatct atccaagtca gagaaacaga ttattatgac gggggggtttg   15780 aaacgtgagt gggtttttaa ggtaacagtc aaggagacca agaatggta taagttagtc   15840 ggatacagtg ccctgattaa ggactaattg gttgaactcc ggaaccctaa tcctgccta    15900 ggtggttagg cattatttgc aatatattaa agaaaactttt gaaaatacga agtttctatt   15960
cccagctttg tctggtggcc ggcatggtcc cagcctcctc gctggcgccg gctgggcaac   16020
attccgaggg gaccgtcccc tcggtaatgg cgaatgggac gcggccgatc cggctgctaa   16080 caaagccccga aaggaagctg agttggctgc tgccaccgct gagcaataac tagcataacc   16140
ccttggggcc tctaaacggg tcttgaggg ttttttgctg aaaggaggaa ctatatccgg   16200
```

```
atgcggccgc gggccctatg gtacccagct tttgttccct ttagtgaggg ttaattccga   16260
gcttggcgta atcatggtca tagctgtttc ctgtgtgaaa ttgttatccg ctcacaattc   16320
cacacaacat aggagccgga agcataaagt gtaaagcctg gggtgcctaa tgagtgaggt   16380
aactcacatt aattgcgttg cgctcactgc ccgctttcca gtcgggaaac ctgtcgtgcc   16440
agctgcatta atgaatcggc caacgcgcgg ggagaggcgg tttgcgtatt gggcgctctt   16500
ccgcttcctc gctcactgac tcgctgcgct cggtcgttcg gctgcggcga gcggtatcag   16560
ctcactcaaa ggcggtaata cggttatcca cagaatcagg ggataacgca ggaaagaaca   16620
tgtgagcaaa aggccagcaa aaggccagga accgtaaaaa ggccgcgttg ctggcgtttt   16680
tccataggct cggcccccct gacgagcatc acaaaaatcg acgctcaagt cagaggtggc   16740
gaaacccgac aggactataa agataccagg cgttccccc tggaagctcc ctcgtgcgct   16800
ctcctgttcc gaccctgccg cttaccggat acctgtccgc ctttctccct tcgggaagcg   16860
tggcgctttc tcaatgctca cgctgtaggt atctcagttc ggtgtaggtc gttcgctcca   16920
agctgggctg tgtgcacgaa ccccccgttc agcccgaccg ctgcgcctta ccggtaact    16980 atcgtcttga gtccaacccg gtaagacacg acttatcgcc actggcagca gccactggta   17040
acaggattag cagagcgagg tatgtaggcg gtgctacaga gttcttgaag tggtggccta   17100
actacggcta cactagaagg acagtatttg gtatctgcgc tctgctgaag ccagttacct   17160
tcggaaaaag agttggtagc tcttgatccg gcaaacaaac caccgctggt agcggtggtt   17220
tttttgtttg caagcagcag attacgcgca gaaaaaaagg atctcaagaa gatcctttga   17280
tcttttctac ggggtctgac gctcagtgga acgaaaactc acgttaaggg attttggtca   17340
tgagattatc aaaaaggatc ttcacctaga tccttttaaa ttaaaaatga agttttaaat   17400
caatctaaag tatatatgag taaacttggt ctgacagtta ccaatgctta atcagtgagg   17460
cacctatctc agcgatctgt ctatttcgtt catccatagt tgcctgactg cccgtcgtgt   17520
agataactac gatacgggag ggcttaccat ctggccccag tgctgcaatg ataccgcgag   17580
acccacgctc accggctcca gatttatcag caataaacca gccagccgga agggccgagc   17640
gcagaagtgg tcctgcaact ttatccgcct ccatccagtc tattaattgt tgccgggaag   17700
ctagagtaag tagttcgcca gttaatagtt tgcgcaacgt tgttgccatt gctacaggca   17760
tcgtggtgtc acgctcgtcg tttggtatgg cttcattcag ctccggttcc caacgatcaa   17820
ggcgagttac atgatccccc atgttgtgaa aaaaagcggt tagctccttc ggtcctccga   17880
tcgttgtcag aagtaagttg gccgcagtgt tatcactcat gcttatggca gcactgcata   17940
attctcttac tgtcatgcca tccgtaagat gcttttctgt gactggtgag tactcaacca   18000
agtcattctg agaatagtgt atgcggcgac cgagttgctc ttgcccggcg tcaatacggg   18060
ataataccgc gccacatagc agaactttaa aagtgctcat cattggaaaa cgttcttcgg   18120
ggcgaaaact ctcaaggatc ttaccgctgt tgagatccag ttcgatgtaa cccactcgtg   18180
cacccaactg atcttcagca tcttttactt tcaccagcgt ttctgggtga gcaaaaacag   18240
gaaggcaaaa tgccgcaaaa aagggaataa gggcgacacg gaaatgttga atactcatac   18300
tcttcctttt tcaatattat tgaagcattt atcagggtta ttgtctcatg agcggataca   18360
tatttgaatg tatttagaaa aataaacaaa taggggttcc gcgcacattt ccccgaaaag   18420
tgccacctga aattgtaaac gttaatattt tgttaaaatt cgcgttaaat tttgttaaa    18480 tcagctcatt ttttaaccaa taggccgaaa tcggcaaaat cccttataaa tcaaagaat    18540 agaccgagat agggttgagt gttgttccag tttggaacaa gagtccacta ttaaagaacg   18600
```

| | |
|---|---|
| tggactccaa cgtcaaaggg cgaaaaaccg tctatcaggg cgatggccca ctacgtgaac | 18660 |
| catcacccta atcaagtttt tgggggtcga ggtgccgtaa agcactaaat cggaaccctaa | 18720 |
| aagggagccc ccgatttaga gcttgacggg gaaagccggc gaacgtggcg agaaaggaag | 18780 |
| ggaagaaagc gaaaggagcg ggcgctaggg cgctggcaag tgtagcggtc acgctgcgcg | 18840 |
| taaccaccac acccgccgcg cttaatgcgc cgctacaggg cgcgtcccat tcgccattca | 18900 |
| ggctgcgcaa ctgttgggaa gggcgatcgg tgcgggcctc ttcgctatta cgccagccac | 18960 |
| cgcggtg | 18967 |

<210> SEQ ID NO 19
<211> LENGTH: 12082
<212> TYPE: DNA
<213> ORGANISM: Artificial
<220> FEATURE:
<223> OTHER INFORMATION: pEMC-LSchw plasmid

<400> SEQUENCE: 19

| | |
|---|---|
| aagcttttgc gatcaataaa tggatcacaa ccagtatctc ttaacgatgt tcttcgcaga | 60 |
| tgatgattca ttttttaagt atttggctag tcaagatgat gaatcttcat tatctgatat | 120 |
| attgcaaatc actcaatatc tagactttct gttattatta ttgatccaat caaaaaataa | 180 |
| attagaagcc gtgggtcatt gttatgaatc tctttcagag gaatacagac aattgacaaa | 240 |
| attcacagac tttcaagatt ttaaaaaact gtttaacaag gtccctattg ttacagatgg | 300 |
| aagggtcaaa cttaataaag gatatttgtt cgactttgtg attagtttga tgcgattcaa | 360 |
| aaaagaatcc tctctagcta ccaccgcaat agatcctgtt agatacatag atcctcgtcg | 420 |
| caatatcgca ttttctaacg tgatggatat attaaagtcg aataaagtga acaataatta | 480 |
| attctttatt gtcatcatga acggcggaca tattcagttg ataatcggcc ccatgttttc | 540 |
| aggtaaaagt acagaattaa ttagacgagt tagacgttat caaatagctc aatataaatg | 600 |
| cgtgactata aaatattcta acgataatag atacggaacg ggactatgga cgcatgataa | 660 |
| gaataatttt gaagcattgg aagcaactaa actatgtgat gtcttggaat caattacaga | 720 |
| tttctccgtg ataggtatcg atgaaggaca gttcttttcca gacattgttg aattgatctc | 780 |
| gatcccgcga aattaatacg actcactata gggagaccac aacggtttcc ctctagcggg | 840 |
| atcaattccg cccctctccc tcccccccc ctaacgttac tggccgaagc cgcttggaat | 900 |
| aaggccggtg tgcgttttgtc tatatgttat tttccaccat attgccgtct tttggcaatg | 960 |
| tgagggcccg gaaacctggc cctgtcttct tgacgagcat tcctaggggt ctttcccctc | 1020 |
| tcgccaaagg aatgcaaggt ctgttgaatg tcgtgaagga agcagttcct ctggaagctt | 1080 |
| cttgaagaca acaacgtct gtagcgaccc tttgcaggca gcggaacccc ccacctggcg | 1140 |
| acaggtgcct ctgcggccaa aagccacgtg tataagatac acctgcaaag gcggcacaac | 1200 |
| cccagtgcca cgttgtgagt tggatagttg tggaaagagt caaatggctc tcctcaagcg | 1260 |
| tattcaacaa ggggctgaag gatgcccaga aggtacccca ttgtatggga tctgatctgg | 1320 |
| ggcctcggtg cacatgcttt acatgtgttt agtcgaggtt aaaaaacgtc tagggcccc | 1380 |
| gaaccacggg gacgtggttt tcctttgaaa aacacgataa taccatggac tcgctatctg | 1440 |
| tcaaccagat cttatacct gaagttcacc tagatagccc gatagttacc aataagatag | 1500 |
| tagccatcct ggagtatgct cgagtccctc acgcttacag cctggaggac cctacactgt | 1560 |
| gtcagaacat caagcaccgc ctaaaaaacg gattttccaa ccaaatgatt ataaacaatg | 1620 |
| tggaagttgg gaatgtcatc aagtccaagc ttaggagtta tccggcccac tctcatattc | 1680 |

```
catatccaaa ttgtaatcag gatttattta acatagaaga caaagagtca acgaggaaga    1740
tccgtgaact cctcaaaaag gggaattcgc tgtactccaa agtcagtgat aaggttttcc    1800
aatgcttaag ggacactaac tcacggcttg gcctaggctc cgaattgagg gaggacatca    1860
aggagaaagt tattaacttg ggagtttaca tgcacagctc ccagtggttt gagccctttc    1920
tgttttggtt tacagtcaag actgagatga ggtcagtgat taaatcacaa acccatactt    1980
gccataggag gagacacaca cctgtattct tcactggtag ttcagttgag ttgctaatct    2040
ctcgtgacct tgttgctata atcagtaaag agtctcaaca tgtatattac ctgacatttg    2100
aactggtttt gatgtattgt gatgtcatag aggggaggtt aatgacagag accgctatga    2160
ctattgatgc taggtataca gagcttctag gaagagtcag atacatgtgg aaactgatag    2220
atggtttctt ccctgcactc gggaatccaa cttatcaaat tgtagccatg ctggagcctc    2280
tttcacttgc ttacctgcag ctgagggata taacagtaga actcagaggt gctttcctta    2340
accactgctt tactgaaata catgatgttc ttgaccaaaa cgggttttct gatgaaggta    2400
cttatcatga gttaactgaa gctctagatt acattttcat aactgatgac atacatctga    2460
caggggagat tttctcatt ttcagaagtt tcggccaccc cagacttgaa gcagtaacgg    2520
ctgctgaaaa tgttaggaaa tacatgaatc agcctaaagt cattgtgtat gagactctga    2580
tgaaaggtca tgccatattt tgtggaatca taatcaacgg ctatcgtgac aggcacggag    2640
gcagttggcc accgctgacc ctcccctgc atgctgcaga cacaatccgg aatgctcaag    2700
cttcaggtga aggagttaaca catgagcagt gcgttgataa ctggaaatct tttgctggag    2760
tgaaatttgg ctgctttatg cctcttagcc tggatagtga tctgacaatg tacctaaagg    2820
acaaggcact tgctgctctc caaagggaat gggattcagt ttacccgaaa gagttcctgc    2880
gttacgaccc tcccaaggga accgggtcac ggaggcttgt agatgttttc cttaatgatt    2940
cgagctttga cccatatgat gtgataatgt atgttgtaag tggagcttac ctccatgacc    3000
ctgagttcaa cctgtcttac agcctgaaag aaaaggagat caaggaaaca ggtagacttt    3060
ttgctaaaat gacttacaaa atgagggcat gccaagtgat tgctgaaaat ctaatctcaa    3120
acgggattgg caaatatttt aaggacaatg ggatggccaa ggatgagcac gatttgacta    3180
aggcactcca cactctagct gtctcaggag tccccaaaga tctcaaagaa agtcacaggg    3240
gggggccagt cttaaaaacc tactcccgaa gcccagtcca cacaagtacc aggaacgtga    3300
gagcagcaaa agggtttata gggttccctc aagtaattcg gcaggaccaa gacactgatc    3360
atccggagaa tatggaagct tacgagacag tcagtgcatt tatcacgact gatctcaaga    3420
agtactgcct taattggaga tatgagacca tcagcttgtt tgcacagagg ctaaatgaga    3480
tttacggatt gccctcattt ttccagtggc tgcataagag gcttgagacc tctgtcctgt    3540
atgtaagtga ccctcattgc cccccgacc ttgacgccca tcccgtta tataaagtcc    3600 ccaatgatca aatcttcatt aagtacccta tgggaggtat agaagggtat tgtcagaagc    3660
tgtggaccat cagcaccatt ccctatctat acctggctgc ttatgagagc ggagtaagga    3720
ttgcttcgtt agtgcaaggg gacaatcaga ccatagccgt aacaaaaagg gtacccagca    3780
catggcccta caaccttaag aaacgggaag ctgctagagt aactagagat tactttgtaa    3840
ttcttaggca aaggctacat gatattggcc atcacctcaa ggcaaatgag acaattgttt    3900
catcacattt ttttgtctat tcaaaaggaa tatattatga tgggctactt gtgtcccaat    3960
cactcaagag catcgcaaga tgtgtattct ggtcagagac tatagttgat gaaacaaggg    4020
cagcatgcag taatattgct acaacaatgg ctaaaagcat cgagagaggt tatgaccgtt    4080
```

```
accttgcata ttccctgaac gtcctaaaag tgatacagca aattctgatc tctcttggct    4140
tcacaatcaa ttcaaccatg acccgggatg tagtcatacc cctcctcaca aacaacgacc    4200
tcttaataag gatggcactg ttgcccgctc ctattggggg gatgaattat ctgaatatga    4260
gcaggctgtt tgtcagaaac atcggtgatc cagtaacatc atcaattgct gatctcaaga    4320
gaatgattct cgcctcacta atgcctgaag agaccctcca tcaagtaatg acacaacaac    4380
cgggggactc ttcattccta gactgggcta gcgaccctta ctcagcaaat cttgtatgtg    4440
tccagagcat cactagactc ctcaagaaca taactgcaag gtttgtcctg atccatagtc    4500
caaacccaat gttaaaagga ttattccatg atgacagtaa agaagaggac gagggactgg    4560
cggcattcct catggacagg catattatag tacctagggc agctcatgaa atcctggatc    4620
atagtgtcac aggggcaaga gagtctattg caggcatgct ggataccaca aaaggcttga    4680
ttcgagccag catgaggaag ggggggttaa cctctcgagt gataaccaga ttgtccaatt    4740
atgactatga acaattcaga gcaggatgg tgctattgac aggaagaaag agaaatgtcc    4800
tcattgacaa agagtcatgt tcagtgcagc tggcgagagc tctaagaagc catatgtggg    4860
cgaggctagc tcgaggacgg cctatttacg gccttgaggt ccctgatgta ctagaatcta    4920
tgcgaggcca ccttattcgg cgtcatgaga catgtgtcat ctgcgagtgt ggatcagtca    4980
actacggatg gttttttgtc ccctcgggtt gccaactgga tgatattgac aaggaaacat    5040
catccttgag agtcccatat attggttcta ccactgatga gagaacagac atgaagcttg    5100
ccttcgtaag agccccaagt cgatccttgc gatctgctgt tagaatagca acagtgtact    5160
catgggctta cggtgatgat gatagctctt ggaacgaagc ctggttgttg gctaggcaaa    5220
gggccaatgt gagcctggag gagctaaggg tgatcactcc catctcaact tcgactaatt    5280
tagcgcatag gttgagggat cgtagcactc aagtgaaata ctcaggtaca tcccttgtcc    5340
gagtggcgag gtataccaca atctccaacg acaatctctc atttgtcata tcagataaga    5400
aggttgatac taactttata taccaacaag gaatgcttct agggttgggt gttttagaaa    5460
cattgtttcg actcgagaaa gataccggat catctaacac ggtattacat cttcacgtcg    5520
aaacagattg ttgcgtgatc ccgatgatag atcatcccag gatacccagc tcccgcaagc    5580
tagagctgag ggcagagcta tgtaccaacc cattgatata tgataatgca cctttaattg    5640
acagagatgc aacaaggcta tacacccaga gccataggag gcaccttgtg gaatttgtta    5700
catggtccac accccaacta tatcacattt tagctaagtc cacagcacta tctatgattg    5760
acctggtaac aaaatttgag aaggaccata tgaatgaaat ttcagctctc ataggggatg    5820
acgatatcaa tagtttcata actgagtttc tgctcataga gccaagatta ttcactatct    5880
acttgggcca gtgtgcggcc atcaattggg catttgatgt acattatcat agaccatcag    5940
ggaaatatca gatgggtgag ctgttgtcat cgttcctttc tagaatgagc aaaggagtgt    6000
ttaaggtgct tgtcaatgct ctaagccacc caaagatcta caagaaattc tggcattgtg    6060
gtattataga gcctatccat ggtccttcac ttgatgctca aaacttgcac acaactgtgt    6120
gcaacatggt ttacacatgc tatatgacct acctcgacct gttgttgaat gaagagttag    6180
aagagttcac attctctctg tgtgaaagcg acgaggatgt agtaccggac agattcgaca    6240
acatccaggc aaaacactta tgtgttctgg cagatttgta ctgtcaacca gggacctgcc    6300
caccaattcg aggtctaaga ccggtagaga aatgtgcagt tctaaccgac catatcaagg    6360
cagaggctat gttatctcca gcaggatctt cgtggaacat aaatccaatt attgtagacc    6420
attactcatg ctctctgact tatctccggc gaggatcgat caaacagata agattgagag    6480
```

```
ttgatccagg attcattttc gacgccctcg ctgaggtaaa tgtcagtcag ccaaagatcg    6540
gcagcaacaa catctcaaat atgagcatca aggctttcag acccccacac gatgatgttg    6600
caaaattgct caaagatatc aacacaagca agcacaatct tcccatttca gggggcaatc    6660
tcgccaatta tgaaatccat gctttccgca gaatcgggtt gaactcatct gcttgctaca    6720
aagctgttga gatatcaaca ttaattagga gatgccttga gccaggggag gacggcttgt    6780
tcttgggtga gggatcgggt tctatgttga tcacttataa agagatactt aaactaaaca    6840
agtgcttcta taatagtggg gtttccgcca attctagatc tggtcaaagg gaattagcac    6900
cctatccctc cgaagttggc cttgtcgaac acagaatggg agtaggtaat attgtcaaag    6960
tgctctttaa cgggaggccc gaagtcacgt gggtaggcag tgtagattgc ttcaatttca    7020
tagttagtaa tatccctacc tctagtgtgg ggtttatcca ttcagatata gagaccttgc    7080
ctgacaaaga tactatagag aagctagagg aattggcagc catcttatcg atggctctgc    7140
tcctgggcaa aataggatca atactggtga ttaagcttat gcctttcagc ggggattttg    7200
ttcagggatt tataagttat gtagggtctc attatagaga agtgaacctt gtatacccta    7260
gatacagcaa cttcatctct actgaatctt atttggttat gacagatctc aaggctaacc    7320
ggctaatgaa tcctgaaaag attaagcagc agataattga atcatctgtg aggacttcac    7380
ctggacttat aggtcacatc ctatccatta agcaactaag ctgcatacaa gcaattgtgg    7440
gagacgcagt tagtagaggt gatatcaatc ctactctgaa aaaacttaca cctatagagc    7500
aggtgctgat caattgcggg ttggcaatta acggacctaa gctgtgcaaa gaattgatcc    7560
accatgatgt tgcctcaggg caagatggat tgcttaattc tatactcatc ctctacaggg    7620
agttggcaag attcaaagac aaccaaagaa gtcaacaagg gatgttccac gcttaccccg    7680
tattggtaag tagcaggcaa cgagaactta tatctaggat caccgcaaa ttctggggc    7740 acattcttct ttactccggg aacaaaaagt tgataaataa gtttatccag aatctcaagt    7800
ccggctatct gatactagac ttacaccaga atatcttcgt taagaatcta tccaagtcag    7860
agaaacagat tattatgacg gggggtttga acgtgagtg ggttttttaag gtaacagtca    7920 aggagaccaa agaatggtat aagttagtcg gatacagtgc cctgattaag gactaattgg    7980
ttgaactccg gaaccctaat cctgccctag gtggttaggc attatttacc tcgagggggc    8040
cggatccact agttctagaa aaaaaaaaaa aaaaaaaaaa aaaaaaaaaa aaaaaaaaaa    8100
aaaaaaaaaa aaaaaaaaaa acgtcgcgca ggtgacaatg tcgagctagc tatgaattcc    8160
ccggggagct cactagtgga tccctgcagc tcgagaggcc taattaatta agtcgacgat    8220
ccggctgcta acaaagcccg aaaggaagct gagttggctg ctgccaccgc tgagcaataa    8280
ctagcataac cccttggggc ctctaaacgg gtcttgaggg gttttttgct gaaaggagga    8340
actatatccg gatcgagatc aattctgtga gcgtatggca aacgaaggaa aaatagttat    8400
agtagccgca ctcgatggga catttcaacg taaaccgttt aataatattt tgaatcttat    8460
tccattatct gaaatggtgg taaaactaac tgctgtgtgt atgaaatgct ttaaggaggc    8520
ttccttttct aaacgattgg gtgaggaaac cgagatagaa ataataggag gtaatgatat    8580
gtatcaatcg gtgtgtagaa agtgttacat cgactcataa tattatattt tttatctaaa    8640
aaactaaaaa taaacattga ttaaatttta atataatact taaaaatgga tgttgtgtcg    8700
ttagataaac cgtttatgta ttttgaggaa attgataatg agttagatta cgaaccagaa    8760
agtgcaaatg aggtcgcaaa aaaactgccg tatcaaggac agttaaaact attactagga    8820
gaattatttt ttcttagtaa gttacagcga cacggtatat tagatggtgc caccgtagtg    8880
```

```
tatataggat ctgctcccgg tacacatata cgttatttga gagatcattt ctataattta    8940
ggagtgatca tcaaatggat gctaattgac ggccgccatc atgatcctat tttaaatgga    9000
ttgcgtgatg tgactctagt gactcggttc gttgatgagg aatatctacg atccatcaaa    9060
aaacaactgc atccttctaa gattatttta atttctgatg tgagatccaa acgaggagga    9120
aatgaaccta gtacggcgga tttactaagt aattacgctc tacaaaatgt catgattagt    9180 atttttaaacc ccgtggcgtc tagtcttaaa tggagatgcc cgtttccaga tcaatggatc    9240
aaggactttt atatcccaca cggtaataaa atgttacaac cttttgctcc ttcatattca    9300
gggccgtcgt tttacaacgt cgtgactggg aaaaccctgg cgttacccaa cttaatcgcc    9360
ttgcagcaca tccccctttc gccagctggc gtaatagcga agaggcccgc accgatcgcc    9420
cttcccaaca gttgcgcagc ctgaatgcg aatggcgcga cgcgccctgt agcggcgcat    9480
taagcgcggc gggtgtggtg gttacgcgca gcgtgaccgc tacacttgcc agcgccctag    9540
cgcccgctcc tttcgctttc ttcccttcct ttctcgccac gttcgccggc tttccccgtc    9600
aagctctaaa tcggggctc cctttagggt tccgatttag tgctttacgg cacctcgacc    9660
ccaaaaaact tgattagggt gatggttcac gtagtgggcc atcgccctga tagacggttt    9720
ttcgcccttt gacgttggag tccacgttct ttaatagtgg actcttgttc caaactggaa    9780
caacactcaa ccctatctcg gtctattctt ttgatttata agggattttg ccgatttcgg    9840
cctattggtt aaaaaatgag ctgatttaac aaaaatttaa cgcgaatttt aacaaaatat    9900
taacgtttac aatttcccag gtggcacttt tcggggaaat gtgcgcggaa cccctatttg    9960 tttattttc taaatacatt caaatatgta tccgctcatg agacaataac cctgataaat   10020
gcttcaataa tattgaaaaa ggaagagtat gagtattcaa catttccgtg tcgcccttat   10080 tcccttttt gcggcatttt gccttcctgt ttttgctcac ccagaaacgc tggtgaaagt   10140
aaaagatgct gaagatcagt tgggtgcacg agtgggttac atcgaactgg atctcaacag   10200
cggtaagatc cttgagagtt ttcgccccga agaacgtttt ccaatgatga gcacttttaa   10260
agttctgcta tgtggcgcgg tattatcccg tattgacgcc gggcaagagc aactcggtcg   10320
ccgcatacac tattctcaga atgacttggt tgagtactca ccagtcacag aaaagcatct   10380 tacgatggc atgacagtaa gagaattatg cagtgctgcc ataaccatga gtgataacac   10440
tgcggccaac ttacttctga caacgatcgg aggaccgaag gagctaaccg cttttttgca   10500
caacatgggg gatcatgtaa ctcgccttga tcgttgggaa ccggagctga atgaagccat   10560
accaaacgac gagcgtgaca ccacgatgcc tgtagcaatg gcaacaacgt tgcgcaaact   10620
attaactggc gaactactta ctctagcttc ccggcaacaa ttaatagact ggatggaggc   10680
ggataaagtt gcaggaccac ttctgcgctc ggcccttccg gctggctggt ttattgctga   10740
taaatctgga gccggtgagc gtgggtctcg cggtatcatt gcagcactgg ggccagatgg   10800
taagccctcc cgtatcgtag ttatctacac gacgggagt caggcaacta tggatgaacg   10860
aaatagacag atcgctgaga taggtgcctc actgattaag cattggtaac tgtcagacca   10920
agtttactca tatatacttt agattgattt aaaacttcat ttttaattta aaaggatcta   10980
ggtgaagatc ctttttgata atctcatgac caaaatccct taacgtgagt tttcgttcca   11040
ctgagcgtca gaccccgtag aaaagatcaa aggatcttct tgagatcctt ttttctgcg   11100 cgtaatctgc tgcttgcaaa caaaaaaacc accgctacca gcggtggttt gtttgccgga   11160
tcaagagcta ccaactcttt ttccgaaggt aactggcttc agcagagcgc agataccaaa   11220
tactgtcctt ctagtgtagc cgtagttagg ccaccacttc aagaactctg tagcaccgcc   11280
```

```
tacatacctc gctctgctaa tcctgttacc agtggctgct gccagtggcg ataagtcgtg   11340
tcttaccggg ttggactcaa gacgatagtt accggataag gcgcagcggt cgggctgaac   11400 gggggggttcg tgcacacagc ccagcttgga gcgaacgacc tacaccgaac tgagatacct   11460
acagcgtgag ctatgagaaa gcgccacgct tcccgaaggg agaaaggcgg acaggtatcc   11520
ggtaagcggc agggtcggaa caggagagcg cacgagggag cttccagggg gaaacgcctg   11580
gtatctttat agtcctgtcg ggtttcgcca cctctgactt gagcgtcgat ttttgtgatg   11640
ctcgtcaggg gggcggagcc tatgaaaaaa cgccagcaac gcggcctttt tacggttcct   11700
ggccttttgc tggccttttg ctcacatgtt ctttcctgcg ttatcccctg attctgtgga   11760
taaccgtatt accgcctttg agtgagctga taccgctcgc cgcagccgaa cgaccgagcg   11820
cagcgagtca gtgagcgagg aagcggaaga gcgcccaata cgcaaaccgc ctctccccgc   11880
gcgttggccg attcattaat gcagctggca cgacaggttt cccgactgga aagcgggcag   11940
tgagcgcaac gcaattaatg tgagttagct cactcattag gcaccccagg ctttacactt   12000
tatgcttccg gctcgtatgt tgtgtggaat tgtgagcgga taacaatttc acacaggaaa   12060
cagctatgac catgattacg cc                                            12082

<210> SEQ ID NO 20
<211> LENGTH: 61
<212> TYPE: DNA
<213> ORGANISM: Artificial
<220> FEATURE:
<223> OTHER INFORMATION: AttB1-T7Pol primer

<400> SEQUENCE: 20
ggggacaagt ttgtacaaaa aagcaggctc caccatggaa ttctctgaca tcgaactggc   60
t                                                                   61

<210> SEQ ID NO 21
<211> LENGTH: 64
<212> TYPE: DNA
<213> ORGANISM: Artificial
<220> FEATURE:
<223> OTHER INFORMATION: AttB2-retourT7Pol primer

<400> SEQUENCE: 21
ggggaccact ttgtacaaga aagctgggtt atcacgcgaa cgcgaagtcc gactctaaga   60
tgtc                                                                64

<210> SEQ ID NO 22
<211> LENGTH: 61
<212> TYPE: DNA
<213> ORGANISM: Artificial
<220> FEATURE:
<223> OTHER INFORMATION: AttBI-SV40nls primer

<400> SEQUENCE: 22
ggggacaagt ttgtacaaaa aagcaggctc caccatggca ccaaaaaaga agagaaaggt   60
a                                                                   61

<210> SEQ ID NO 23
<211> LENGTH: 58
<212> TYPE: DNA
<213> ORGANISM: Artificial
<220> FEATURE:
<223> OTHER INFORMATION: AttB1-N primer

<400> SEQUENCE: 23
```

```
ggggacaagt tgtacaaaa aagcaggctc catggccaca cttttaagga gcttagca        58

<210> SEQ ID NO 24
<211> LENGTH: 60
<212> TYPE: DNA
<213> ORGANISM: Artificial
<220> FEATURE:
<223> OTHER INFORMATION: AttB2-N primer

<400> SEQUENCE: 24
gggaccactt tgtacaagaa agctgggtgt gtactagtct agaagatttc tgtcattgta    60

<210> SEQ ID NO 25
<211> LENGTH: 55
<212> TYPE: DNA
<213> ORGANISM: Artificial
<220> FEATURE:
<223> OTHER INFORMATION: AttB1-P primer

<400> SEQUENCE: 25
ggggacaagt tgtacaaaa aagcaggctc catggcagaa gagcaggcac gccat          55

<210> SEQ ID NO 26
<211> LENGTH: 68
<212> TYPE: DNA
<213> ORGANISM: Artificial
<220> FEATURE:
<223> OTHER INFORMATION: AttB2-P primer

<400> SEQUENCE: 26
ggggaccact tgtacaaga aagctgggtg ttactacttc attattatct tcatcagcat     60
ctggtgga                                                             68
```